(12) United States Patent
Meng et al.

(10) Patent No.: US 8,946,270 B2
(45) Date of Patent: Feb. 3, 2015

(54) AMIDO-PYRIDYL ETHER COMPOUNDS AND COMPOSITIONS AND THEIR USE AGAINST PARASITES

(75) Inventors: Charles Q. Meng, Grayson, GA (US); Clare Louise Murray, Chapel Hill, NC (US); Itta Bluhn-Chertudi, Durham, NC (US); Mustapha Soukri, Raleigh, NC (US); Mary George Johnson, Durham, NC (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 14/127,248

(22) PCT Filed: Jun. 27, 2012

(86) PCT No.: PCT/US2012/044476
§ 371 (c)(1),
(2), (4) Date: Feb. 4, 2014

(87) PCT Pub. No.: WO2013/003505
PCT Pub. Date: Jan. 3, 2013

(65) Prior Publication Data
US 2014/0179746 A1    Jun. 26, 2014

Related U.S. Application Data

(60) Provisional application No. 61/501,492, filed on Jun. 27, 2011.

(51) Int. Cl.
*A01N 43/40* (2006.01)
*C07D 213/18* (2006.01)
*C07D 405/12* (2006.01)

(52) U.S. Cl.
CPC .............. *A01N 43/40* (2013.01); *C07D 213/18* (2013.01); *C07D 405/12* (2013.01)
USPC .......................................... 514/354; 546/323

(58) Field of Classification Search
None
See application file for complete search history.

(56) References Cited

U.S. PATENT DOCUMENTS 7,964,735 B2 *    6/2011    Yanagi et al. ................. 546/316

FOREIGN PATENT DOCUMENTS

| EP | 2151437 | 2/2010 |
|---|---|---|
| WO | WO 2007/008963 | 1/2007 |
| WO | WO 2010/151797 | 12/2010 |
| WO | WO 2011/101229 | 8/2011 |

* cited by examiner

*Primary Examiner* — Janet L Andres
*Assistant Examiner* — Timothy R Rozof
(74) *Attorney, Agent, or Firm* — Judy Jarecki-Black; John Ezcurra; Merial Limited

(57) ABSTRACT

The subject matter disclosed herein is directed to amido-pyridyl ether compounds of formula I:

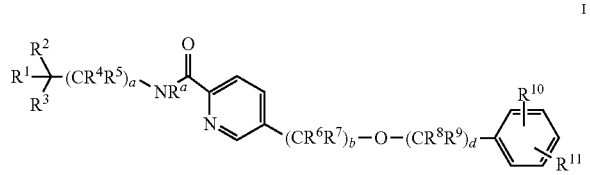

wherein, $R^1$, $R^2$, $R^3$, $R^4$, $R^5$, $R^6$, $R^7$, $R^8$, $R^9$, $R^{10}$, $R^{11}$, $R^a$, a, b and d are as described herein, compositions comprising the compounds of formula I, methods for their preparation and methods for their uses against parasites.

28 Claims, No Drawings

AMIDO-PYRIDYL ETHER COMPOUNDS AND COMPOSITIONS AND THEIR USE AGAINST PARASITES

CROSS REFERENCE TO RELATED APPLICATIONS

This application is a national stage application of International Application No. PCT/US2012/044476 filed Jun. 27, 2012, which claims the benefit of priority to U.S. Provisional Application No. 61/501,492 filed Jun. 27, 2011, which is incorporated herein by reference in its entirety.

FIELD OF THE INVENTION

The subject matter disclosed herein is directed to 2-amido-pyridyl ether compounds of formula I:

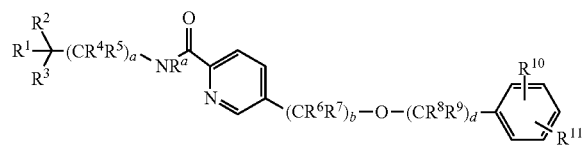

wherein, $R^1$, $R^2$, $R^3$, $R^4$, $R^5$, $R^6$, $R^7$, $R^8$, $R^9$, $R^{10}$, $R^{11}$, $R^a$, a, b and d are as described herein, compositions comprising the compounds of formula I, methods for their preparation and methods for their uses against parasites.

BACKGROUND

Animals such as mammals and birds are often susceptible to parasite infestations. These parasites may be ectoparasites, such as insects, and endoparasites such as filariae and worms. Domesticated animal, such as cats and dogs, are often infested with one or more of the following ectoparasites: cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dermatobia* sp., *Coclyomia* sp., and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents, agents which cause diseases in both humans and animal. Major diseases which are caused by ticks include borrelioses (Lyme disease caused by *Borrelia burgdorferi*), babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is a tick genus *Boophilus*, especially those of the species microplus (cattle tick), decoloratus and anulatus. Ticks, such as *Boophilus microplus*, are particularly difficult to control because they live in the pasture where the farm animals graze. Other important parasites of cattle and sheep are listed as follows in order of decreasing importance: myiases such as *Dermatobia hominis* (known as Berne in Brazil) and *Cochlyomia hominivorax* (greenbottle); sheep myiases such as *Lucilia sericata, Lucilia cuprina* (known as blowfly strike in Australia, New Zealand and South Africa). These are flies whose larva constitutes the animal parasite; flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

Animals and humans also suffer from endoparasitical infections including, for example, helminthiasis which is most frequently caused by a group of parasitic worms described as nematodes or roundworms. These parasites cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

Many insecticides exist in the art for treating parasites. These insecticides vary in their effectiveness against a particular parasite as well as their cost. However the results of these insecticides are not always satisfactory because of, for example, the development of resistance by the parasite to the therapeutic agent, as is the case, for example, with carbamates, organophosphorus compounds and pyrethroids. Thus, there is a need in the art for more effective antiparasitic formulation treatment and protection of animal, e.g. mammals, fish and birds for a wide range of parasites. Moreover, there is a need in the art for an antiparasitic formulation which is easy to use on any type of domestic animal, irrespective of its size and the nature of its coat, and which does not need to be sprinkled over the entire body of the mammal, fish or bird. What is needed are compounds that are effective against a range pests, particularly for controlling endoparasites or ectoparasites in or on animals.

BRIEF SUMMARY

The present disclosure is based, in part, on unexpected results that compounds of formula I have efficacy against a range of pests including ectoparasites or endoparasites or both.

In an embodiment, the subject matter disclosed herein is directed to compounds of formula I.

In an embodiment, the subject matter disclosed herein is directed to solid state forms of the compounds of the invention which consists of crystalline forms including single crystals, nanocrystals, co-crystals, molecular complexes, hydrates, anhydrates, solvates, desolvates, clathrates and inclusion complexes and non-crystalline forms including non-crystalline glass and non-crystalline amorphous forms.

In an embodiment, the subject matter disclosed herein is directed to pesticidal compositions comprising a compound of formula I.

In an embodiment, the subject matter disclosed herein is directed methods of treating a pest infestation by contacting the site of infestation or its surroundings with a compound of formula I or a composition thereof.

In an embodiment, the subject matter disclosed herein is directed to preventing or protecting an area from pest infestation by contacting the site in need of prevention or protection or its surroundings with a compound of formula I or a composition thereof.

In an embodiment, the subject matter disclosed herein is directed to a method of preventing or protecting an animal from pest or its habitat from pest infestation by contacting the animal or its habitat with a compound of formula I or a composition thereof.

In an embodiment, the subject matter disclosed herein is directed to methods of preparing the compounds and compositions disclosed herein.

DETAILED DESCRIPTION

The 2-Amido-pyridyl ether compounds and compositions thereof disclosed herein have been found to have activity against pests, particularly endoparasites or ectoparasites or both. The compounds of formula I disclosed herein are useful against pests directly or can be used in the areas that pests infest or are likely to infest. The compounds are also useful for applying to animals to treat or prevent parasite infestations or infections. This includes methods for preventing and/or treating a parasitic infestation or infection in an animal, and the use of the compounds in treating a parasitic infestation or infection in an animal or the use in the manufacture of a medicament for treating a parasitic infestation or infection in an animal.

I. Definitions

The compounds of the invention are intended to encompass racemic mixtures, specific stereoisomers and tautomeric forms of the compound. Another aspect of the invention is a salt form of the compound of the invention.

The term "subject" or "animal" as used herein includes warm-blooded and cold-blooded animals such as mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

As referred to in this disclosure, the term "pest" or "parasite" includes arthropods, gastropods and nematodes. The term "arthropod" includes insects, mites, spiders, scorpions, centipedes, millipedes; pill bugs and symphylans. The term "gastropod" includes snails, slugs and other Stylommatophora. The term "helminths;" includes worms in the phyla of Nemathelminthes, Platyhelminthes and Acanthocephala such as: round worms, heartworms, and phytophagous nematodes (Nematoda), flukes (Trematoda), tape worms (Cestoda) and thorny-headed worms. Also specifically included are endoparasites and ectoparasites.

For the purposes of this application, unless otherwise stated in the specification, the following chemical terms have the terminology cited below:

(1) Alkyl refers to both straight, branched carbon chains and cyclic hydrocarbon groups; references to individual alkyl groups are specific for the straight chain (e.g. butyl=n-butyl).

In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-4 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyls, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Third Edition, 1999, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10 or 2-8. In yet another embodiment of alkenyl, the number of carbon atoms is 2-4. Other ranges of carbon-carbon double bonds and carbon numbers are also contemplated depending on the location of the alkenyl moiety on the molecule;

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl- 1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10 or 2-8. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl. Arylo refers to an aryl substituted at two adjacent sites.

(5) Alkoxy refers to —O-alkyl, wherein alkyl is as defined in (1);

(6) Alkoxycarbonyl refers to —C(═O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(9) Heterocycle, heterocyclic or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a 2-amidopyridyl ether compound as disclosed herein or another active in combination with one or more 2-amidopyridyl ether compounds.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

II. Compounds

In an embodiment, the subject matter disclosed herein is directed to a compound of Formula I:

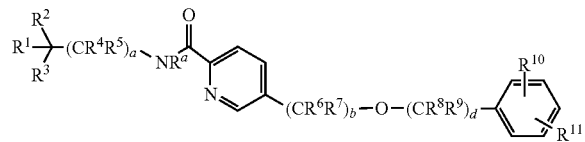

wherein, $R^a$ is selected from the group consisting of hydrogen, alkyl, alkoxyalkyl, alkylcarbonyl, haloalkylcarbonyl, alkoxycarbonyl, haloalkoxycarbonyl, alkylthiocarbonyl, haloalkyl, alkylthio, haloalkylthio, alkoxy, haloalkoxyalkyl, alkoxycarbonyl and haloalkoxycarbonyl;

$R^1$ is hydrogen or alkyl;

$R^2$ and $R^3$ are each independently selected from the group consisting of hydrogen, hydroxy, amino, alkyl, haloalkyl, alkoxyalkyl, alkenyl, alkynyl, alkylthio, alkylamino, dialkylamino, aminoalkyl, alkylaminoalkyl, dialkylaminoalkyl, and cyano, or $R^2$ and $R^3$ taken together with the carbon to which both are bound form a substituted or unsubstituted 3- to 7-member cyclic, heterocyclic or heteroaromatic ring, wherein the substituents may each be independent of one another cyano, nitro, halogen, alkyl, haloalkyl, alkylthio, haloalkylthio, alkoxy, haloalkoxy, amino, alkylamino, and dialkylamino;

a is an integer from zero to four, b is an integer from zero to four, d is an integer from zero to four, $R^4, R^5, R^6, R^7, R^8$ and $R^9$ are each independently hydrogen, halogen, alkyl, alkenyl, hydroxyalkyl, alkylthioalkyl, haloalkyl, alkyloxyalkyl, alkylsulfinylalkyl, alkylsulfonylalkyl, alkylsulfonyloxyalkyl, nitro, alkylthio, haloalkylthio, alkoxy, haloalkoxy, amino, alkylamino, and diamino;

$R^{10}$ and $R^{11}$ are each independently selected from the group consisting of hydrogen, hydroxy, amino, cyano, nitro, halogen, thiol, alkylamino, dialkylamino, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, formyl, alkylcarbonyl, alkoxycarbonyl, sulfonyl, sulfinyl, and unsubstituted or substituted phenyl, unsubstituted or substituted benzyl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, alkoxy, haloalkoxy, amino, alkylamino, dialkylamino, alkylaminoalkoxy, dialkylaminoalkoxy, and alkylaminoalkyl, provided that, at least one of b and d is other than zero, and at least one of $R^{10}$ and $R^{11}$ is other than hydrogen.

Preferred compounds of formula I include those where:

$R^a$ is selected from the group consisting of hydrogen, $C_{1-6}$ alkyl, $C_{1-6}$ alkoxy($C_{1-6}$)alkyl, $C_{1-6}$ alkylcarbonyl, halo($C_{1-6}$)alkylcarbonyl, $C_{1-6}$ alkoxycarbonyl, halo($C_{1-6}$)alkoxycarbonyl, $C_{1-6}$ alkylthiocarbonyl, halo($C_{1-6}$)alkyl, $C_{1-6}$ alkylthio, halo($C_{1-6}$)alkylthio, $C_{1-6}$ alkoxy, halo($C_{1-6}$)alkoxy($C_{1-6}$)alkyl, $C_{1-6}$ alkoxycarbonyl and halo($C_{1-6}$)alkoxycarbonyl;

$R^1$ is hydrogen or $C_{1-6}$ alkyl;

$R^2$ and $R^3$ are each independently selected from the group consisting of hydrogen, hydroxy, amino, $C_{1-6}$ alkyl, halo($C_{1-6}$)alkyl, alkoxy($C_{1-6}$)alkyl, $C_{1-6}$ alkenyl, $C_{1-6}$ alkynyl, $C_{1-6}$ alkylthio, $C_{1-6}$ alkylamino, di($C_{1-6}$ alkyl)amino, aminoalkyl, alkylaminoalkyl, dialkylaminoalkyl, and cyano, or $R^2$ and $R^3$ taken together with the carbon to which both are bound form a substituted or unsubstituted 3- to 7-member cyclic, heterocyclic or heteroaromatic ring, wherein the substituents may each be independent of one another cyano, nitro, halogen, $C_{1-6}$ alkyl, halo($C_{1-6}$)alkyl, $C_{1-6}$ alkylthio, halo($C_{1-6}$)alkylthio, $C_{1-6}$ alkoxy, halo($C_{1-6}$)alkoxy, amino, $C_{1-6}$ alkylamino, and di($C_{1-6}$ alkyl)amino;

a is an integer from zero to four, b is an integer from zero to four, d is an integer from zero to four, $R^4, R^5, R^6, R^7, R^8$ and $R^9$ are each independently hydrogen, halogen, $C_{1-6}$ alkyl, $C_{1-6}$ alkenyl, hydroxy($C_{1-6}$)alkyl, $C_{1-6}$ alkylthio($C_{1-6}$)alkyl, halo($C_{1-6}$)alkyl, $C_{1-6}$ alkyloxy($C_{1-6}$)alkyl, $C_{1-6}$ alkylsulfinyl($C_{1-6}$)alkyl, $C_{1-6}$ alkylsulfonyl($C_{1-6}$)alkyl, $C_{1-6}$ alkylsulfonyloxy($C_{1-6}$)alkyl, nitro, $C_{1-6}$ alkylthio, halo($C_{1-6}$)alkylthio, $C_{1-6}$ alkoxy, halo($C_{1-6}$)alkoxy, amino, alkylamino, and di($C_{1-6}$ alkyl)amino;

$R^{10}$ and $R^{11}$ are each independently selected from the group consisting of hydrogen, hydroxy, amino, cyano, nitro, halogen, thiol, alkylamino, dialkylamino, $C_{1-6}$ alkyl, $C_{1-6}$ alkenyl, $C_{1-6}$ alkynyl, $C_{3-7}$cycloalkyl, hydroxy($C_{1-6}$)alkyl, halo ($C_{1-6}$)alkyl, $C_{1-6}$ alkylthio, halo($C_{1-6}$)alkylthio, arylthio, $C_{1-6}$ alkoxy, phenoxy, alkoxy($C_{1-6}$)alkoxy, $C_{3-7}$cyclo($C_{1-6}$)alkyloxy, halo($C_{1-6}$)alkoxy, formyl, alkylcarbonyl, alkoxycarbonyl, sulfonyl, sulfinyl, and unsubstituted or substituted phenyl, unsubstituted or substituted benzyl, unsubstituted or substituted arylthio, unsubstituted or substituted aryloxy, or unsubstituted or substituted heteroaryl, wherein the substituents, independent of one another, may be one or more of cyano, nitro, halogen, $C_{1-6}$ alkyl, halo($C_{1-6}$)alkyl, $C_{1-6}$ alkylthio, halo($C_{1-6}$)alkylthio, $C_{1-6}$ alkoxy, halo($C_{1-6}$)alkoxy, amino, alkylamino, di($C_{1-6}$ alkyl)amino, $C_{1-6}$ alkylamino ($C_{1-6}$)alkoxy, $C_{1-6}$ dialkylamino($C_{1-6}$)alkoxy, and $C_{1-6}$ alkylamino($C_{1-6}$)alkyl, provided that,
at least one of b and d is other than zero, and
at least one of $R^{10}$ and $R^{11}$ is other than hydrogen.

Combinations of substituents and/or variables the various embodiments described herein are permissible only if such combinations result in stable compounds.

Preferred compounds of formula I include those where b is one and d is zero, b is two and d is zero, b is one and d is one, b is zero and d is one, or b is zero and d is two. In these preferred compounds, it is more preferable that a is one or two.

Preferred compounds of formula I include any compound of formula I where a is one or two. Also preferred are compounds where a is zero, provided that when $R^{10}$ and $R^{11}$ are both selected from the group consisting of chloro and methyl, then:
i) d is other than zero, or
ii) $R^a$ is other than $C_{1-6}$ alkyl, or
iii) $R^2$ and $R^3$ when taken together with the carbon to which both are bound form a ring other than cyclopentyl or cyclohexyl.

Preferred compounds of formula I include those where $R^{10}$ and $R^{11}$ are each independently selected from the group consisting of hydrogen, halogen, branched or straight-chain $C_{1-6}$ alkyl, $C_{1-6}$ alkenyl, $C_{1-6}$ alkynyl, hydroxy($C_{1-6}$)alkyl, halo($C_{1-6}$)alkyl, $C_{1-6}$ alkoxy, halo($C_{1-6}$)alkoxy and unsubstituted or substituted phenyl, wherein the substituents, independent of one another, may be one or more of halogen, $C_{1-6}$ alkyl, halo($C_{1-6}$)alkyl, $C_{1-6}$ alkoxy, or halo($C_{1-6}$)alkoxy. More preferably, $R^{10}$ and $R^{11}$ are each independently selected from the group consisting of hydrogen, bromo, chloro, fluoro, methyl, ethyl, trifluoromethyl and trifluoromethoxy.

Preferred compounds of formula I include those where a is one, $R^4$ and $R^5$ are both hydrogen, b is zero, one or two, and d is zero, one or two. In these preferred compounds, it is also preferred that b is one or two, d is zero, and $R^6$ and $R^7$ in each instance are both hydrogen. In these preferred compounds, it is also preferred that d is one or two, b is zero, and $R^8$ and $R^9$ in each instance are both hydrogen. In these preferred compounds, it is also preferred that b is one or two, $R^6$ and $R^7$ in each instance are both hydrogen, d is one or two, and $R^8$ and $R^9$ in each instance are both hydrogen.

Preferred compounds of formula I include those where $R^1$ is hydrogen or methyl, $R^2$ and $R^3$ are each independently selected from the group consisting of hydrogen, $C_{1-6}$ alkenyl, cyano, $C_{1-6}$ alkyl, $C_{1-6}$ alkoxy, amino, $C_{1-6}$ alkylamino, di($C_{1-6}$ alkyl)amino and $C_{1-6}$ alkylthio, or $R^2$ and $R^3$ taken together with the carbon to which both are bound form a substituted or unsubstituted 3- to 7-member cyclic, heterocyclic or heteroaromatic ring. In these preferred compounds, it is also preferred that $R^2$ and $R^3$ are each independently selected from the group consisting of hydrogen, $C_{1-6}$ alkenyl, $C_{1-6}$ alkyl and $C_{1-6}$ alkylthio. In these preferred compounds, it is preferable that $R^2$ and $R^3$ taken together with the carbon to which both are bound form a substituted or unsubstituted 3- to 7-member cyclic, heterocyclic or pyridine. More preferably, $R^2$ and $R^3$ taken together with the carbon to which both are bound form a substituted or unsubstituted pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, 2-pyrrolinyl, 3-pyrrolinyl, 2H-pyranyl, 4H-pyranyl, dioxanyl, 1,3-dioxolanyl, dithianyl, dithiolanyl and dihydrothienyl. Most preferably, $R^2$ and $R^3$ taken together with the carbon to which both are bound form a substituted or unsubstituted cyclopropyl or 4-morpholinyl.

Preferred compounds of formula I include those where $R^a$ is hydrogen.

Preferred compounds of formula I include those where $R^1$ is hydrogen or methyl.

Preferred compounds of formula I include those where $R^2$ and $R^3$ are each independently selected from the group consisting of hydrogen, $C_{1-6}$ alkenyl, cyano, $C_{1-6}$ alkyl, $C_{1-6}$ alkoxy, amino, $C_{1-6}$ alkylamino, di($C_{1-6}$alkyl)amino and $C_{1-6}$ alkylthio, or $R^2$ and $R^3$ taken together with the carbon to which both are bound form a substituted or unsubstituted 3- to 7-member cyclic, heterocyclic or heteroaromatic ring. When $R^2$ and $R^3$ are taken together with the carbon to which both are bound, preferred rings are substituted or unsubstituted pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, 2-pyrrolinyl, 3-pyrrolinyl, 2H-pyranyl, 4H-pyranyl, dioxanyl, 1,3-dioxolanyl, dithianyl, dithiolanyl and dihydrothienyl. Preferred compounds include those where $R^2$ and $R^3$ taken together with the carbon to which both are bound form a substituted or unsubstituted cyclopropyl or 4-morpholinyl. Preferred compounds include those where $R^2$ and $R^3$ are each independently selected from the group consisting of hydrogen, $C_{1-6}$ alkenyl, $C_{1-6}$ alkyl and $C_{1-6}$ alkylthio.

Preferred compounds of formula I include the following:

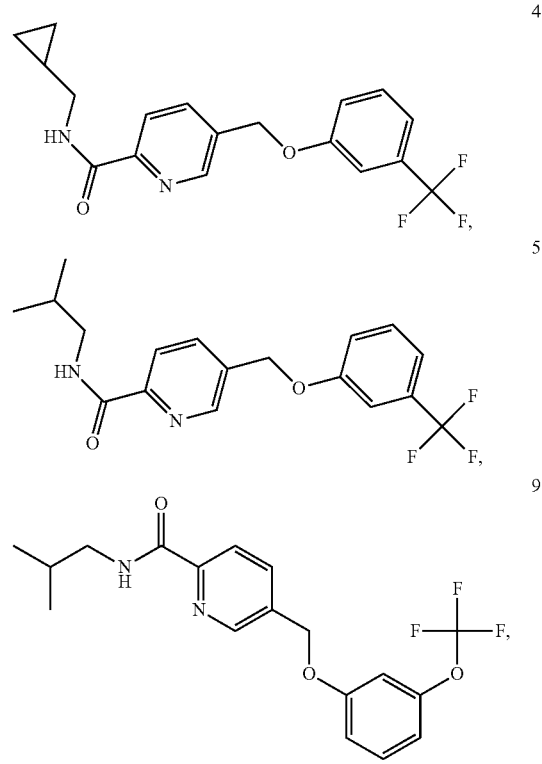

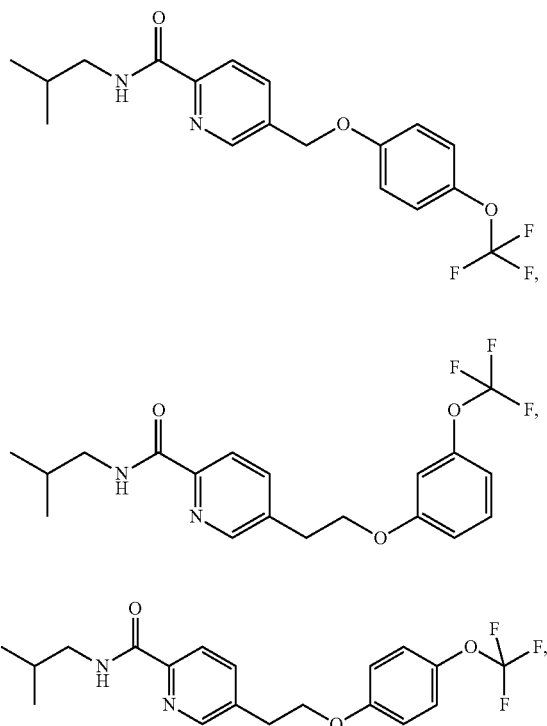
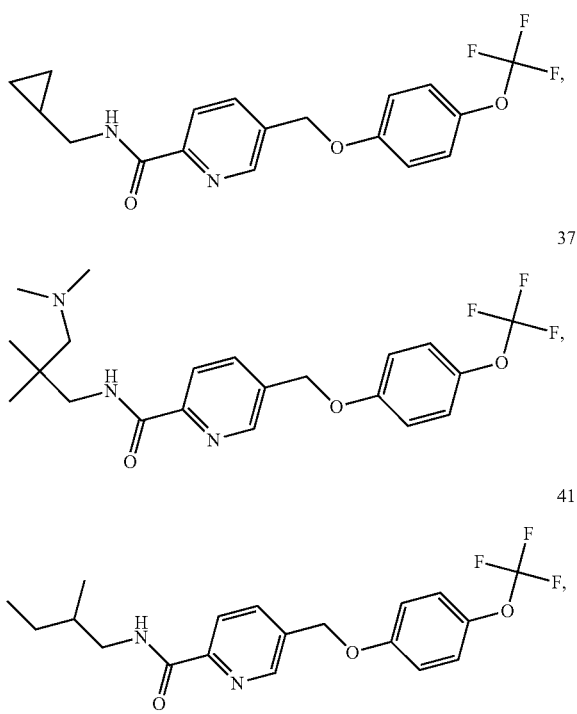

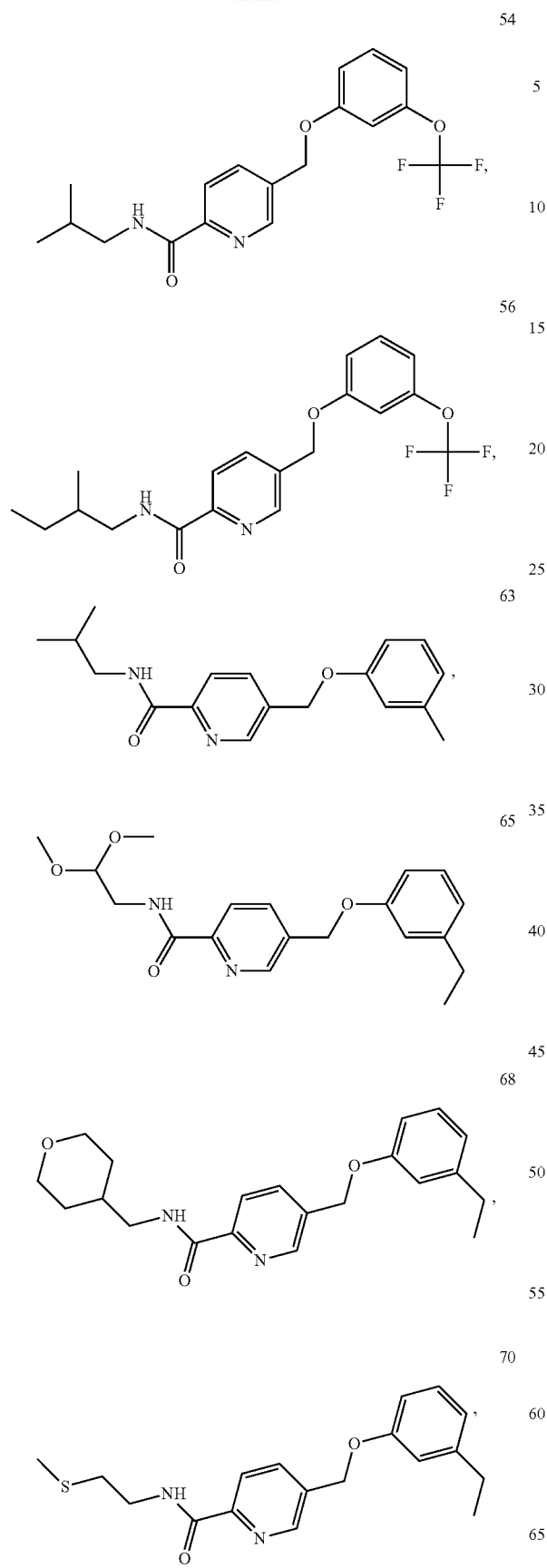

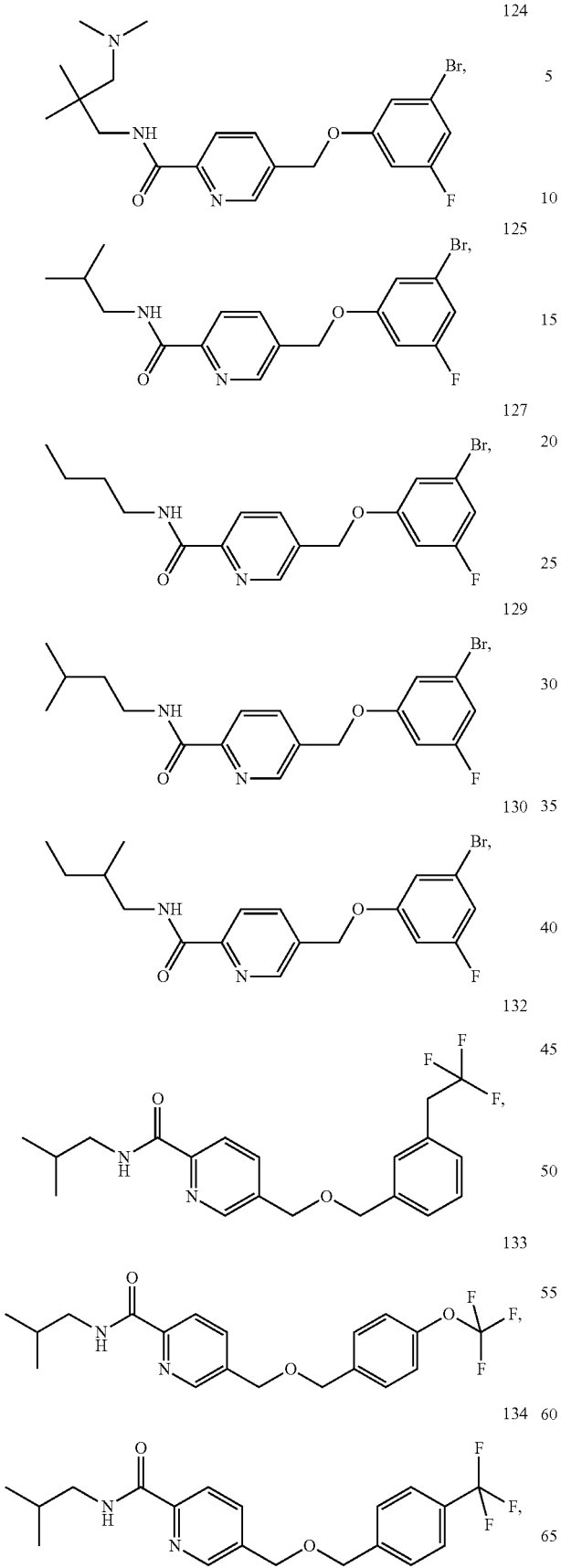
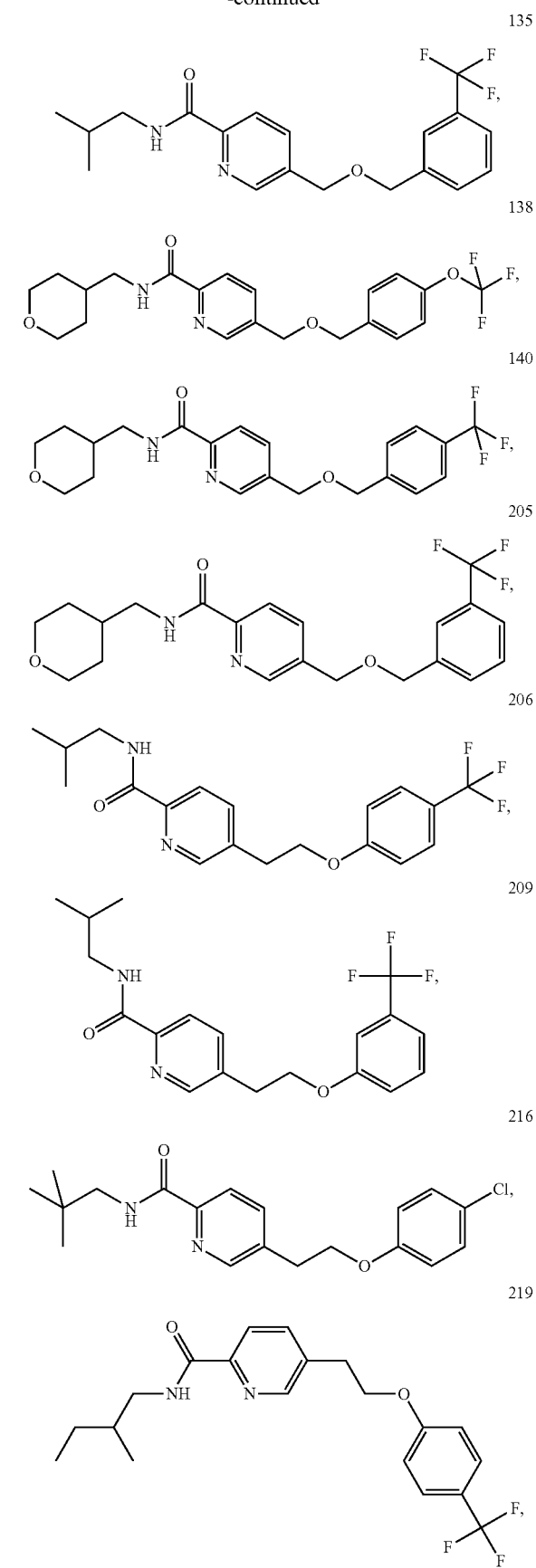

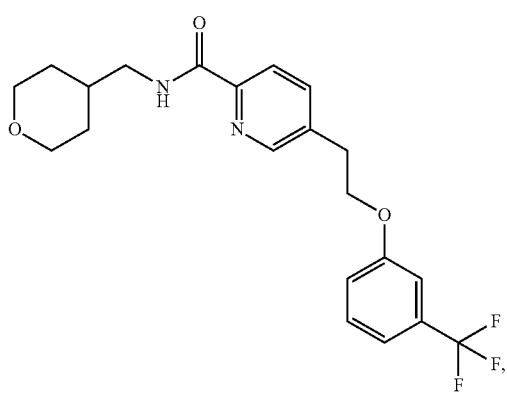
220
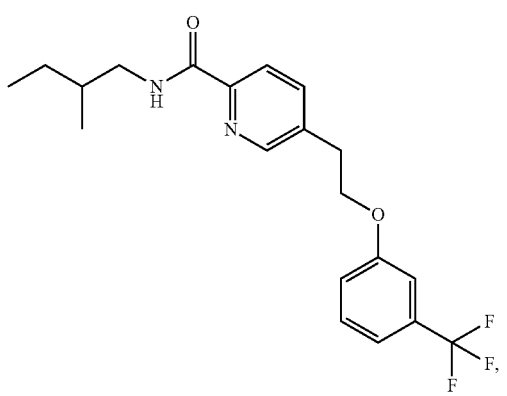
221
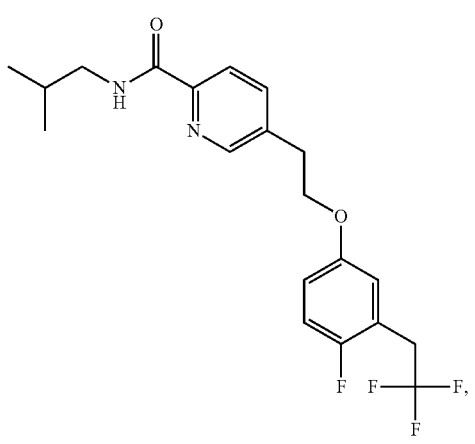
222
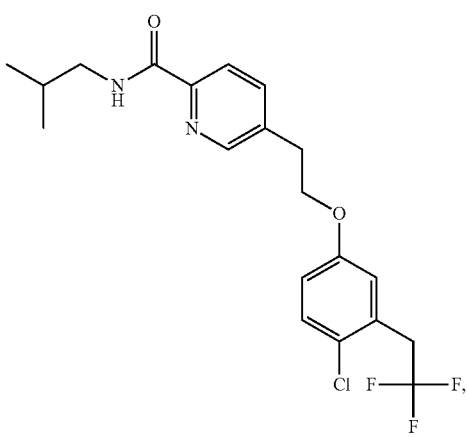
223
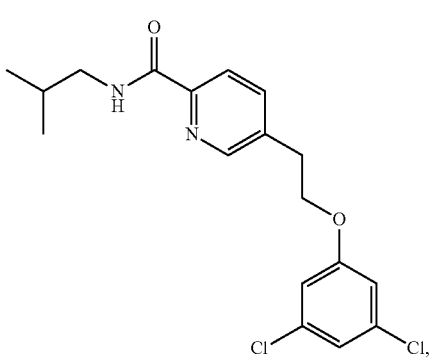
225
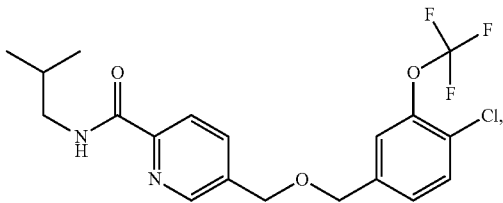
227
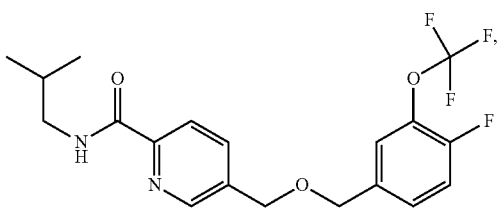
228
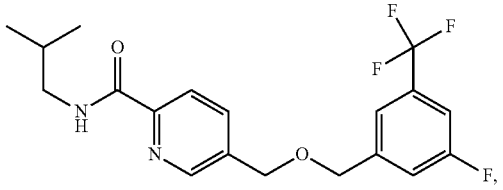
229

232
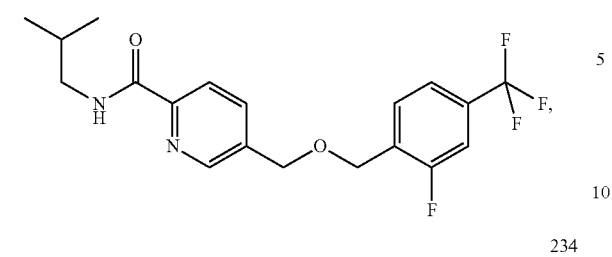
234
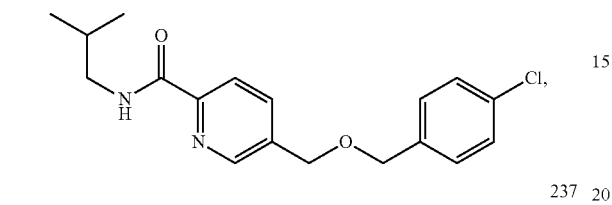
237
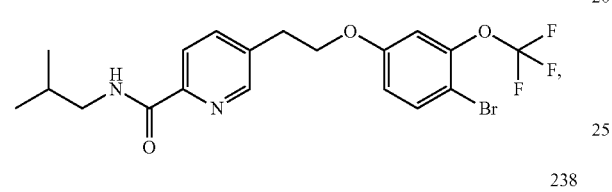
238
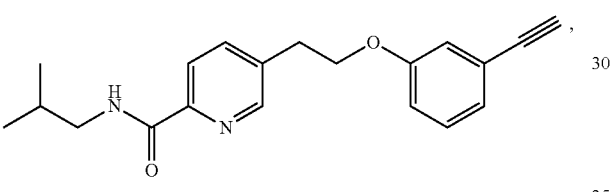
240
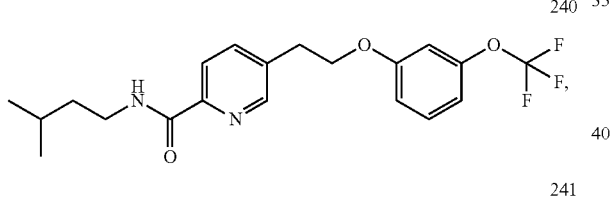
241
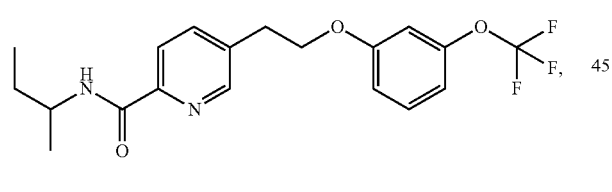
242
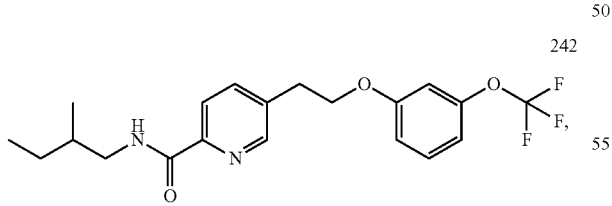
243
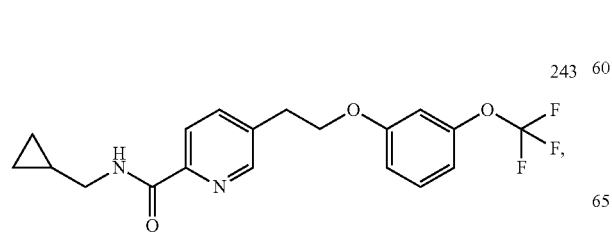
256
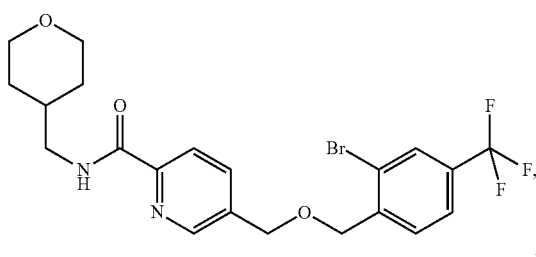
257
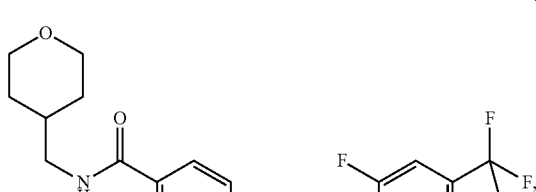
258
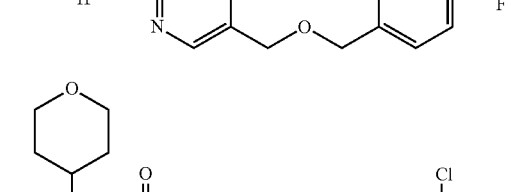
259
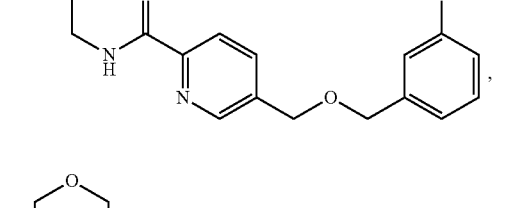
260
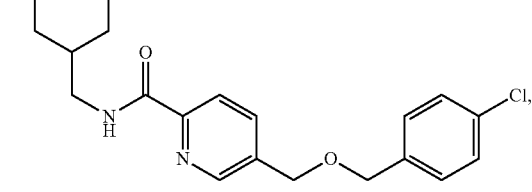
263
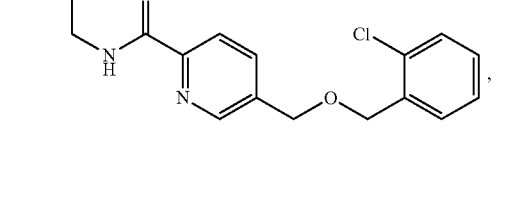
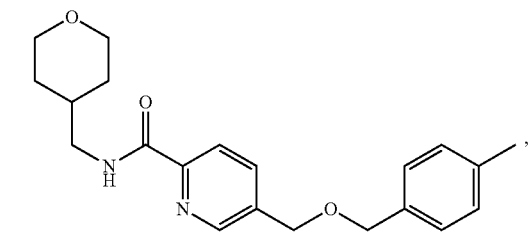

-continued

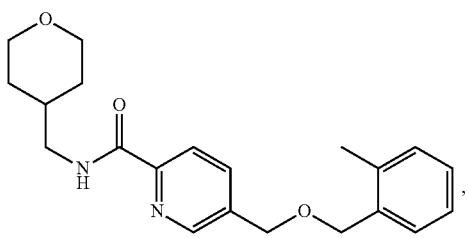
264

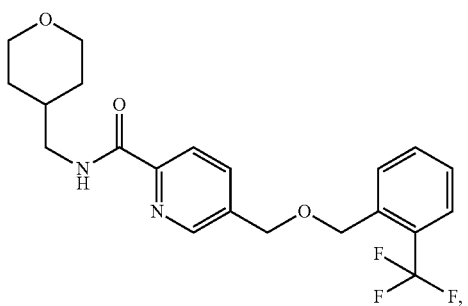
266

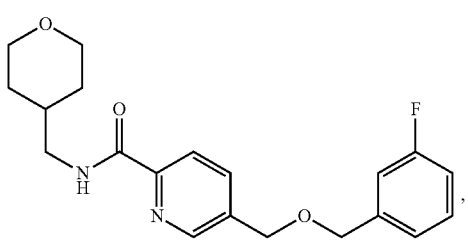
268

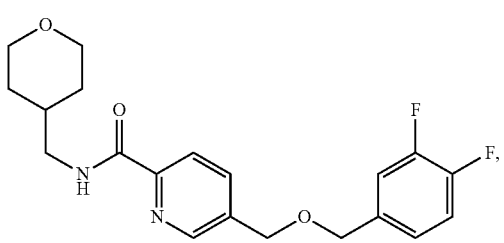
270

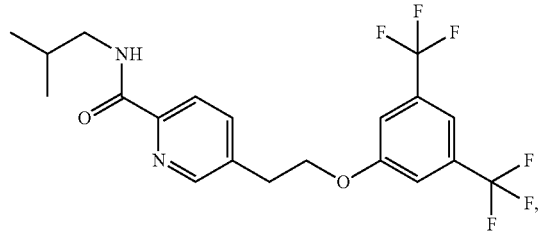
275

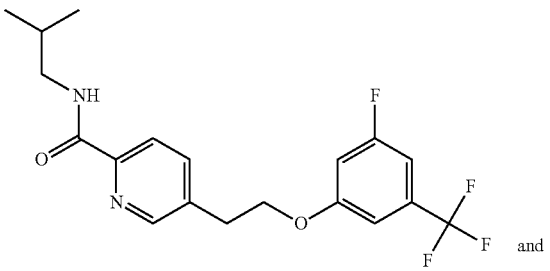
278 and

-continued

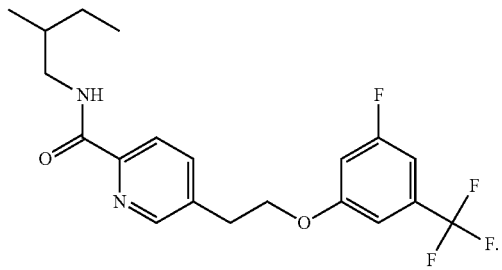
279

Other useful compounds of formula I are described elsewhere herein.

III. Compositions

Various methods of formulating antiparasitical formulations are known in the art. These include oral formulations, baits, dietary supplements, powders, shampoos, concentrated solution, suspension, microemulsion, emulsion, oral drench formulation, chewable formulation, transdermal or transmucosal patch or liquid, gel or paste, solution for inhalation and injectable formulation. Formulations for localized topical applications of antiparasitical formulations are also known in the art, such as ready-to-use solutions, pour-on solutions, spot-on formulations, paste formulations, shampoos, powders, etc. are well known in the art.

The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition may be in a form suitable for oral use, for example, as baits (see, e.g., U.S. Pat. No. 4,564,631), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat.

Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin.

Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyinylpyrrolidone, gum tragacanth and gum acacia; dispersing or wetting agents may be a naturally-ocurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment, the composition can be in paste form. Examples of embodiments in a paste form include but are not limited to those described in U.S. Pat. Nos. 6,787,342 and 7,001,889 (each of which are incorporated herein by reference). The paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing at least one 2-amido-pyridyl ether compound(s) described herein into the carrier by mixing;

(b) adding the fumed silica to the carrier above, and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste. The above steps are illustrative, but not limiting. For example, step (a) can be the last step.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (POLYSORBATE 80 or TWEEN 80), and polyoxamers (e.g., PLURONIC L 81); an absorbent selected from the group consisting of magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, a spot-on or pour-on composition, can allow for the inventive compound to be absorbed through the skin to achieve systemic levels, distributed through the sebaceous glands or on the surface of the skin achieving levels throughout the haircoat. When the compound is distributed through the sebaceous glands, they can act as a reservoir, whereby there can be a long-lasting effect (up to several months) effect. Spot-on formulations are typically applied in a localized region which refers to an area other than the entire animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. One embodiment of the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the 2-amido-pyridyl ether compound(s) and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment, the composition can be in ready-to-use solution form as is described in U.S. Pat. No. 6,395,765, incorporated herein by reference. These formulations may be in the form of spot-on or pour-on formulations to be applied to a localized area on an animal. In addition to the 2-amido-pyridyl ether compound(s), the ready-to-use solution can contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a the test in which 0.3 ml of a solution comprising 10% (w/v) of the 2-amido-pyridyl ether compound(s) in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

In one embodiment, the organic solvent has a dielectric constant of a range selected from the group consisting of between about 2 to about 35, about 10 to about 35 or about 20 to about 30. In other embodiments, the solvent will have a dielectric constant of between about 2 and about 20, or between about 2 and about 10. The content of this organic solvent in the overall composition representing the complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, this co-solvent may be present in the composition in a organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsufoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. Other mixtures of crystallization inhibitors are also contemplated, including mixtures of two or more, three or more, four or more or even five or more, of the individual crystallization inhibitors described herein. These agents will be selected from the compounds mentioned above as crystallization inhibitors, or equivalent compounds.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80. In yet another embodiment, the crystallization inhibitor comprises a polyoxyethylenated derivatives of castor oil, including polyoxyethylenated hydrogenated castor oil derivatives. In still another embodiment, the crystallization inhibitor comprises a polyethylene glycol.

In another embodiment, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal.

In another embodiment, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

In one embodiment, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of the 2-amido-pyridyl ether compound(s) present. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment, the 2-amido-pyridyl ether compound(s) is present in the formulation at a concentration of about 0.05% to about 50% weight/volume. In other embodiments, the 2-amido-pyridyl ether compound(s) may be present in the formulation at a concentration of about 0.1% to about 30%, about 0.5% to about 20% (w/v) or about 1% to about 10% (w/v). In another embodiment, the 2-amido-pyridyl ether compound(s) is present in the formulation as a concentration from about 0.1 to 2% weight/volume. In yet another embodiment, the 2-amido-pyridyl ether compound(s) is present in the formulation as a concentration from about 0.25 to about 1.5% weight/volume. In still another embodiment, the 2-amido-pyridyl ether compound(s) is present in the formulation as a concentration about 1% weight/volume.

In a particular advantageous embodiment of the invention, the dose of the 2-amido-pyridyl ether compound(s) is about 0.1 mg/kg to about 100 mg/kg. In other embodiments, the dose of the 2-amido-pyridyl ether compound(s) is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the 2-amido-pyridyl ether compound(s) is about 0.1 mg/kg to 5 mg/kg, 0.1 mg/kg to about 3 mg/kg, or about 0.1 mg/kg to 1.5 mg/kg. In still other embodiments, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

The compounds of formula I or their salts can be employed as such or in the form of their preparations (formulations) as combinations with other active substances, such as, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzo-thiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones.

Other fungicides that may optionally be admixed may also be from the classes of compounds described in U.S. Pat. Nos. 7,001,903 and 7,420,062.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl (thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluoroxypyr and picloram; quinoline carboxylic acid; phthalamate semicarbazone; qrylaminopropionic acid; qrylaminopropionic acid; organoarsenical.

Other herbicides that may optionally be admixed are compounds described in U.S. Pat. Nos. 7,432,226, 7,012,041, and 7,365,082.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, each incorporated herein by reference, the literature known to the person skilled in the art, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

The compounds of formula I can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula I, also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula I are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula I in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula I onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula I.

The concentration of compounds of formula I in wettable powders is, for example, about 10 to about 90% by weight, the remainder to 100% by weight being composed of customary formulation components. In the case of emulsifiable concentrates, the concentration of compounds of formula I can amount to ranges selected from the group consisting of about 1% to about 90% and about 5% to about 80% by weight. Formulations in the form of dusts usually comprise in the range selected from the group consisting of about 1% to about 30% by weight of compounds of formula I and about 5% to about 20% by weight of compounds of formula I. For sprayable solutions comprise a range selected from the group consisting of about 0.05% to about 80% by weight of compounds of formula I and about 2% to about 50% by weight of compounds of formula I. In the case of water-dispersible granules, the content of compounds of formula I depends partly on whether the compounds of formula I are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula I mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Additional pharmaceutically or veterinarily active ingredients may also be added to the compositions of the invention. In some embodiments, the additional active agents may be one or more parasiticidal compounds including acaricides, anthelmintics, endectocides and insecticides. Anti-parasitic agents can include both ectoparasiticisal and endoparasiticidal agents.

Veterinary pharmaceutical agents that may be included in the compositions of the invention are well-known in the art (see e.g. *Plumb' Veterinary Drug Handbook*, 5th Edition, ed. Donald C. Plumb, Blackwell Publishing, (2005) or *The Merck Veterinary Manual*, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, camitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment, arylpyrazole compounds such as phenylpyrazoles (e.g. fipronil, pyriprole), may be suitable for combination with the aryloazol-2-yl cyanoethylamino compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131—each assigned to Merial, Ltd., Duluth, Ga.

In another embodiment, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582, 5,962,499, 6,221,894 and 6,399,786. The composition can include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181.

In another embodiment, the compositions may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment, the compositions may advantageously include at least one compound of formula I in combination with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In another embodiment, the compositions may be combined with cyclo-depsipeptide anthelmintic compounds including emodepside (see Willson et al., *Parasitology*, January 2003, 126 (Pt 1):79-86).

In some embodiments, the compositions may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, santonin and kainic acid.

In other embodiments, the compositions may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and meniclopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions including, but not limited to, arecoline in various salt forms, bunamidine, niclosamide, nitroscanate, paromomycin and paromomycin II.

In yet other embodiments, the compositions may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, carbaryl, promacyl, propoxur, allethrin, cyhalothrin, cypermethrin, deltamethrin, fenvalerate, flucythrinate, permethrin, phenothrin, pyrethrins, resmethrin, amitraz, benzyl benzoate, carbon disulfide, crotamiton, diflubenzuron, diphenylamine, disulfuram, isobornyl thiocyanato acetate, methoprene, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio) ethanol (MGK-874).

In another embodiment of the invention, one or more macrocyclic lactones, which act as an acaricide, anthelmintic agent and insecticide, can be added to the compositions of the invention. The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of macrocyclic lactones with other active agents are described in U.S. Pat. Nos. 6,426,333; 6,482,425; 6,962,713 and 6,998, 131—each assigned to Merial, Ltd., Duluth, Ga., all incorporated herein by reference.

The macrocyclic lactone compounds are known in the art and can be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., "Macrocyclic Lactones in Antiparasitic Therapy", 2002, by J Vercruysse and R S Rew published by CABI Publishing or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structures of the avermectins and milbemycins are closely related, e.g., by sharing a complex 16-membered macrocyclic lactone ring; milbemycins lack the glycosidic moiety of the avermectins. The natural products avermectins are disclosed in U.S. Pat. No. 4,310, 519 to Albers-Schonberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. No. 5,077, 308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920, 148 and EP 0 667 054.

In another embodiment, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798, 837; U.S. Pat. No. 4,751,225, EP 0 179 022 or U.K. 2 140 010 as well as U.S. Pat. Nos. 6,096,329 and 6,685,954 (both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

A parasiticidal agent that can be combined with at least one compound of formula I to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined at least one compound of formula I to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular parasitic infection/infestation. For ectoparasites, active agents that can be combined also include but are not limited to pyrethoids, organophosphates and neonicotinoids such as imidacloprid, as well as compounds such as metaflumizone, amitraz and ryanodine receptor antagonists.

Where appropriate the anthelmintic, parasiticidal and insecticial agent may also be selected from the group of compounds described above as suitable for agrochemical use.

In general, at least one compound of formula I is included in a dose of between about 0.1 µg and about 500 mg. In some embodiments, the additional active agent may be present in a dose of about 1 mg to about 500 mg, about 1 mg to about 300 mg, or about 1 mg to about 100 mg. In other embodiments, the additional active agent may be present in a dose of about 1 mg to about 50 mg or about 1 mg to about 20 mg. In other embodiment of the invention, the additional active agent is included in a dose of about 1 µg to about 10 mg.

In another embodiment, the additional active agent is included in a dose of about 5 g/kg to about 50 mg/kg. In other embodiments, the additional active agent may be included in a dose of about 5 µg/kg to about 30 mg/kg, about 5 µg/kg to about 20 mg/kg or about 5 µg/kg to about 10 mg/kg. In still other embodiments, the additional active agent may be included in a dose of about 10 µg/kg to about 1 mg/kg or about 50 µg/kg to about 500 µg/kg of weight of the animal. In yet another embodiment, the additional active agent is included in a dose between about 0.1 mg/kg to about 10 mg/kg of weight of animal. In still another embodiment, the additional active agent is included in a dose between about 0.5 mg/kg to 50 mg/kg.

The proportions, by weight, of the at least one compound of formula I and the additional active agent are for example between about 5/1 and about 10,000/1. However, one of ordinary skill in the art would be able to select the appropriate ratio of 2-amido-pyridyl ether compound(s) and the additional active agent for the intended host and use thereof.

The subject matter disclosed herein is also directed to a treated seed comprising a compound of formula I in an amount of from about 0.0001 to 1% by weight of the seed before treatment.

IV. Methods of Use

In another embodiment, the subject matter described herein is directed to a method of treating endoparasitic infestation or infection in an animal, comprising administering an effective amount of at least one 2-amido-pyridyl ether compound(s) as described herein to an animal or subject in need thereof. The compounds of the invention have been shown to have excellent efficacy against endoparasites, ectoparasites or both.

In one embodiment, the compounds and compositions of the invention may be used for treating endoparasiticidal infection or infestation by helminth species including, but is not limited to, *Anaplocephala (Anoplocephala), Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, and combinations thereof.

In a preferred embodiment, the helminth is *Haemonchus contortus, Ostertagia circumcincta, Trichostrongylus axei, Trichostrongylus colubriformis, Cooperia curticei, Nematodirus battus* and combinations thereof.

In another embodiment, the subject matter disclosed herein is directed toward a method of treating ectoparasitic infestation or infection in an animal in need thereof which comprises administering an effective amount of the compound of the invention to the animal in need thereof. In an embodiment, the ectoparasite is an arthropod. Preferably, the arthropod is selected from the group consisting of houseflies (*Musca domestica*), *Musca hervei*, *Musca bezzi*, *Haematobia irritans*, *Simulium iwatens*, *Culicoides oxystoma*, *Tabanus chrysurus*, common mosquito (*Culex pipiens*), *Aedes albopictus*; lice pests (Anoplura), cattle lice (*Haematopinus eurysternus*), sheep lice (*Damalinia ovis*); tick pests (Acarina), *Haemaphysalis longiconis*, *Boophilus microplus*; fleas (Siphonaptera), cat fleas (*Ctenocephalides felis*), dog fleas (*Ctenocephalides canis*) and oriental rat flea (*Xenopsylla cheopis*).

In one embodiment, the infection or infestation is caused by fleas, ticks, mites, mosquitoes, flies, lice, blowfly, fly larvae and combinations thereof. Preferably, the pest or parasite is selected from the group consisting of flies, including hornfly and stable fly, fleas, ticks and mosquitos.

In one embodiment, the subject matter disclosed herein is directed to a method for treating an ectoparasitic infestation or infection in an animal, comprising administering an effective amount of at least one 2-amido-pyridyl ether compound(s) as described herein in combination with a second active ingredient to an animal.

In one embodiment, the parasite is an ectoparasite or an endoparasite or a combination thereof.

The methods include contacting a pest or parasite with at least one 2-amido-pyridyl ether compound as described herein. The methods also include contacting the areas and vicinities where the pests or parasites infest or reside. In a prophylactic treatment, the methods include contacting the areas or vicinities susceptible to pest or parasitic infestation or residence.

The subject of the present invention is also a process for the elimination of parasites in mammals and birds, especially dogs and cats, using a composition according to the present invention.

In one embodiment of the invention, direct pour-on skin formulation according to the present invention can obtain long-lasting and broad-spectrum efficacy when the solution is applied to the animal's back, preferably along the line of the back at one or more points.

According to an embodiment for administering direct pour-on formulations, the process consists in applying the solution to the animals in pasture and/or before they arrive in pasture, the application preferably being repeated every month, preferably every two months.

According to another embodiment for administering direct pour-on formulation, the process consists in applying the solution to livestock animals before they arrive in the "Feed Lot", it being possible for this application to be the final one before the animals are slaughtered.

This method can serve to cleanse the skin and the hairs of the animals by eliminating the parasites which are present thereon, as well as their residues and dejections. The result of this is that the animals are no longer stressed by the parasites and their bites, this having positive consequences, for example on their growth and on the use of their food ration.

In another embodiment, application of spot-on formulation can also obtain long-lasting and broad-spectrum efficacy when the solution is applied to the mammal or bird.

Administration of the spot-on formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case. For example, it is preferable for the treatment according to the invention to be carried out monthly on dogs and on cats.

The administration of spot-on formulations also provides for a method for cleaning the coats and the skin of animals by removal of the parasites which are present and of their waste and excreta. The animals treated thus exhibit a coat which is more pleasing to the eye and more pleasant to the touch.

In an embodiment, the present subject matter is directed to a method for protecting a seed from a pest comprising contacting the seed with a biologically effective amount of a compound of formula I.

V. Articles of Manufacture

In an embodiment, the present subject matter is directed to a device for controlling a pest comprising a bait composition containing at least one 2-amido-pyridyl ether compound and a housing adapted to receive the bait composition, wherein the housing has at least one opening sized to permit the pest to pass through an opening that allows the pest access to the bait composition from a location outside the housing, and wherein the housing is further adapted to be placed in or near a locus of potential or known activity for the pest.

VI. Examples

A. Methods of Preparing Compounds of Formula I

The compounds of formula I may be prepared according to the processes described herein or by the application or adaptation of known methods (i.e. methods heretofore used or described in the chemical literature).

All temperatures are given in degrees Centigrade; room temperature means 20 to 25° C. Reagents were purchased from commercial sources or prepared following literature procedures. Proton and fluorine magnetic resonance (respectively 1H NMR and 19F NMR) spectra were recorded on a Varian INOVA NMR spectrometer [400 MHz (1H) and 377 MHz (19F)], Bruker NMR spectrometer [400 MHz (1H) and 377 MHz (19F)] and Bruker NMR spectrometer [300 MHz (1H)]. All spectra were determined in the solvents indicated. Chemical shifts are reported in ppm downfield of tetramethylsilane (TMS), referenced to the residual proton peak of the respective solvent peak for 1H NMR. LC-MS spectra were obtained using: Shimadzu SP-20A 2010EV using a Shimpack XR-ODS 2.2 micron C18 50×3.0 mm column and a linear gradient from 10% acetonitrile with 0.1% formic acid in water with 0.1% formic acid to 100% acetonitrile with 0.1% formic acid over 2 minutes; 100% acetonitrile with 0.1% formic acid was held for 1 minute. Waters Acquity HPLC system using an Ascentis® Express C18 HPLC Column, 75×2.1 mm, 2.7 u. Column temperature was held at 40° C. Solvent A: 10 mMol Ammonium Acetate in 5% Acetonitrile/Water with 0.1% v/v Acetic acid. Solvent B: Acetonitrile. Method ran from 0% B to 100% B over 0.7 min holding at 100% B for 0.15 min then returning to initial conditions for 0.15 min at a flow rate of 1.5 mL/min. Agilent 1200SL LC equipped with a 6130 single quadrupole mass spectrometer and SofTa (Westminster, Colo.) 300s ELSD using a Shimadzu Shim-pack XR-ODS, 3.0×30 mm, 2.2 μm, was used at a temperature of 50° C. and at a flow rate of 1.5 mL/min, 2 μL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B).

Schemes 1-5 depict synthetic routes to yield carboxylic acid and ester containing derivatives via 5-(bromoethyl)-2-chloropyridine. The derivatives are useful for preparing compounds of formula I.

Example 1

Synthesis of Compound I-4

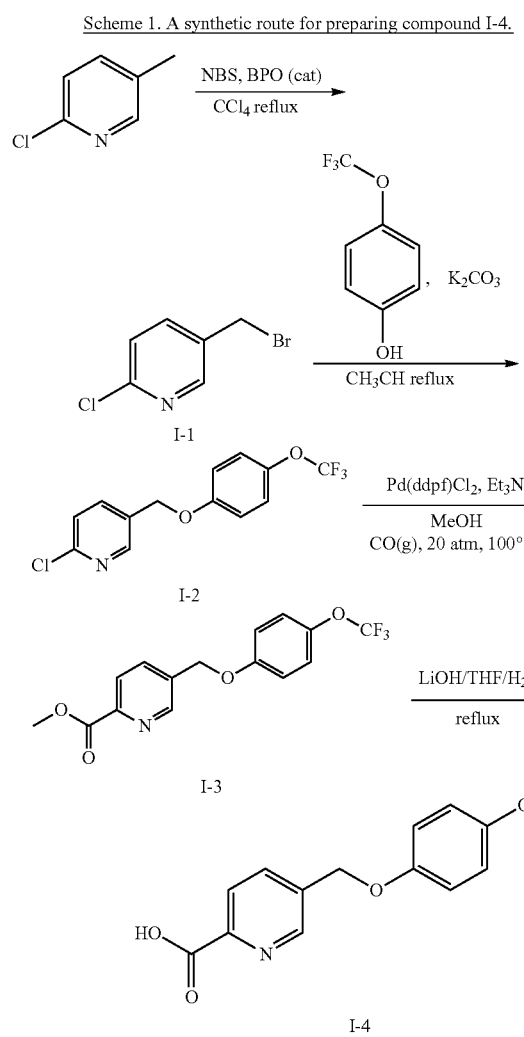

Scheme 1. A synthetic route for preparing compound I-4.

Example 2

Synthesis of Compound I-1

Into a 1000-mL round-bottom flask, was placed 2-chloro-5-methylpyridine (44 g, 344.83 mmol, 1.00 equiv), perchloromethane (500 mL), 1-bromopyrrolidine-2,5-dione (60 g, 337.08 mmol, 0.98 equiv), and benzoic peroxyanhydride (1 g). The resulting solution was heated to reflux for overnight. The solids were removed by filteration. The filtrate was concentrated under vacuum. The residue was applied onto a silica gel column with ethyl acetate/petroleum ether (1:20). This resulted in 22 g (31%) of 5-(bromomethyl)-2-chloropyridine as a white solid.

LC-MS: (ES, m/z): 208 [M+H]+

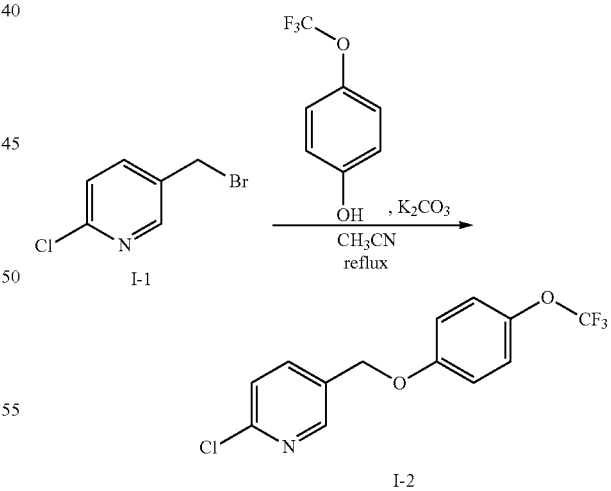

Scheme 2. A synthetic route for preparing compound I-1.

Example 3

Synthesis of Compound I-2

Into a 1000-mL round-bottom flask, was placed 5-(bromomethyl)-2-chloropyridine (22 g, 106.54 mmol, 1.00 equiv), 4-(trifluoromethoxy)phenol (22 g, 123.53 mmol, 1.16 equiv), acetonitrile (300 mL), and potassium carbonate (22 g, 159.19 mmol, 1.49 equiv). The resulting solution was heated at reflux overnight. The resulting mixture was concentrated under vacuum. The residue was dissolved in 300 mL of dichloromethane. The solids were removed by filtration. The filtrate was concentrated under vacuum. This resulted in 25 g (77%) of 2-chloro-5-((4-(trifluoromethoxy)phenoxy)methyl)pyridine as a light yellow solid.

LC-MS: (ES, m/z): 304 [M+H]+

Scheme 3. A synthetic route for preparing compound I-2.

Example 4

Synthesis of Compound I-3

Into a 1000-mL pressure tank reactor, was placed 2-chloro-5-((4-(trifluoromethoxy)phenoxy)methyl)pyridine (25 g, 82.32 mmol, 1.00 equiv), methanol (300 mL), triethylamine (16.7 g, 165.02 mmol, 2.00 equiv), and Pd(dppf)Cl₂ (2 g). To the above CO (g) was introduced at 20 atm pressure. The resulting solution was stirred for 1 hr overnight at 100° C. The resulting mixture was cooled and concentrated under vacuum. The residue was applied onto a silica gel column with dichloromethane/petroleum ether (1:1). This resulted in 15 g (56%) of methyl 5-((4-(trifluoromethoxy)phenoxy)methyl)picolinate as a light yellow solid LC-MS: (ES, m/z): 328 [M+H]⁺

Scheme 4. Synthetic route for preparing compound I-3.

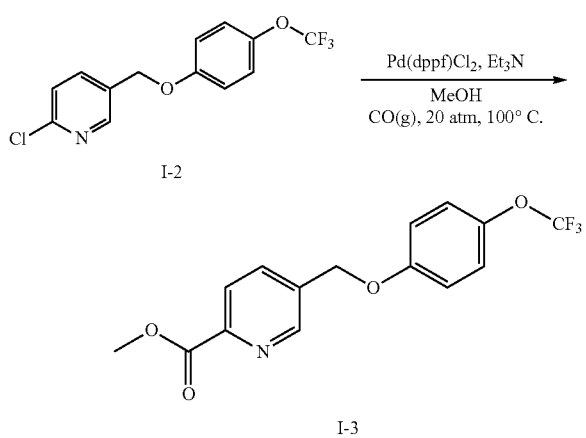

Example 5

Synthesis of I-4

Into a 500-mL round-bottom flask, was placed a solution of methyl 5-((4-(trifluoromethoxy)phenoxy)methyl)picolinate (15 g, 45.83 mmol, 1.00 equiv) in tetrahydrofuran (100 mL), and a solution of lithium hydroxide (2.2 g, 92.05 mmol, 2.01 equiv) in water (100 mL). The resulting solution was heated to reflux for 1 hr. The resulting mixture was concentrated under vacuum. The pH value of the solution was adjusted to 6 with acetic acid. The solids were collected by filtration and dried in an oven under reduced pressure. This resulted in 9.6 g (67%) of 5-((4-(trifluoromethoxy)phenoxy)methyl)picolinic acid as a white solid.

LC-MS: (ES, m/z): 314 [M+H]⁺

¹H-NMR: (400 MHz, DMSO-d6, ppm): δ5.29 (s, 2H), 7.15 (m, 2H), 7.33 (m, 2H), 8.06 (m, 2H), 8.79 (s, 1H).

19F-NMR: (376 MHz; DMSO-d6, ppm): −57.25 (s, 3F)

Scheme 5. A synthetic route for preparing compound I-4.

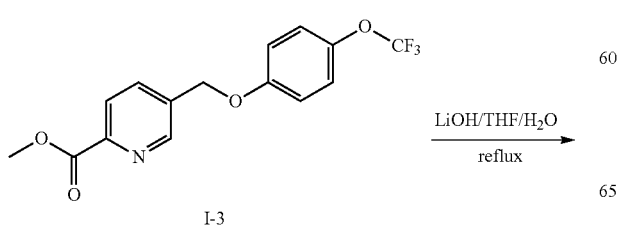

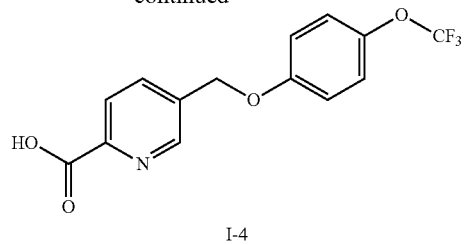

Schemes 6-19 depict synthetic routes to yield carboxylic acid and ester containing derivatives via 5-(bromoethyl)picolinate. The derivatives are useful for preparing compounds of formula I.

Example 6

Synthesis of I-548-0

Scheme 6. A synthetic route for preparing compound I-548-0.

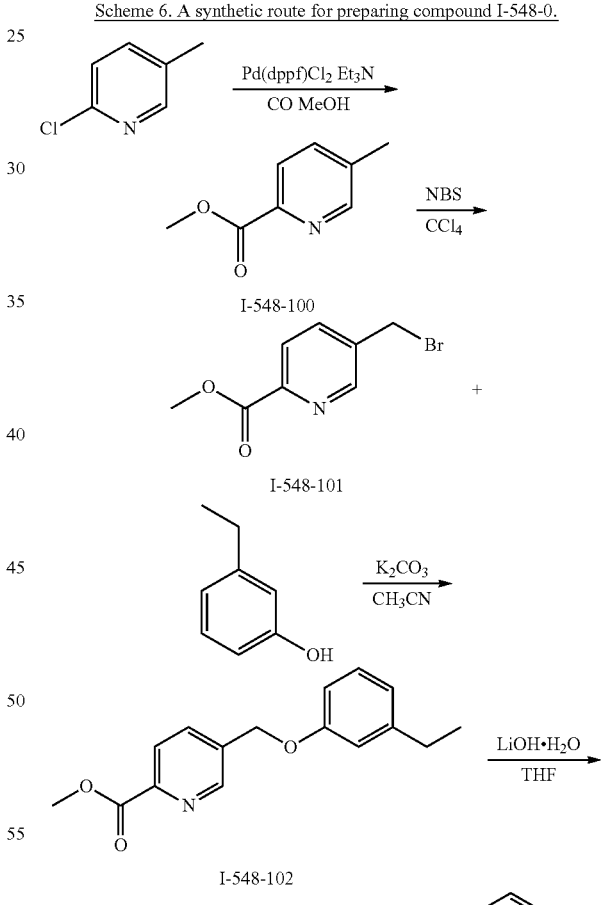

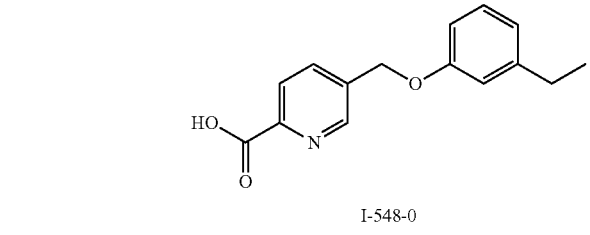

Example 7

Synthesis of I-548-100

Into a 2-L pressure tank reactor was placed a solution of 2-chloro-5-methylpyridine (100 g, 783.70 mmol, 1.00 equiv) in methanol (1000 mL), triethylamine (158.6 g, 1.57 mol, 2.00 equiv), and Pd(dppf)Cl$_2$(5 g). To the above CO (g) was introduced at 20 atm pressure and heated to reflux overnight. The resulting mixture was concentrated under vacuum. The residue was applied onto a silica gel column with ethyl acetate/petroleum ether (1:50-1:5). This resulted in 50 g (41%) of methyl 5-methylpicolinate as an off-white solid.

LC-MS: (ES, m/z): 152 [M+H]$^+$

Scheme 7. A synthetic route for preparing compound I-548-100.

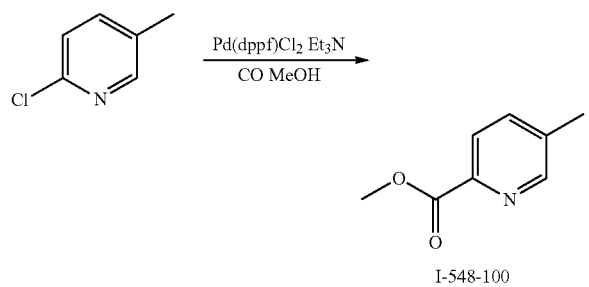

Example 8

Synthesis of I-548-101

Into a 2000-mL 4-necked round-bottom flask, was placed a solution of methyl 5-methylpicolinate (85 g, 539.68 mmol, 1.00 equiv, 96%) in CCl$_4$ (1000 mL), N-bromosuccinimide (110 g, 617.98 mmol, 1.10 equiv), and benzoyl peroxide (3.5 g, 14.45 mmol, 0.03 equiv). The resulting solution was heated to reflux overnight. The solids were removed by filtration. The filtrate was concentrated under vacuum. The residue was applied onto a silica gel column with ethyl acetate/petroleum ether (1:30-1:5). This resulted in 15 g (11%) of methyl 5-(bromomethyl)picolinate as a light-yellow solid.

LC-MS: (ES, m/z): 232 [M+H]$^+$

Scheme 8. A synthetic route for preparing compound I-548-101.

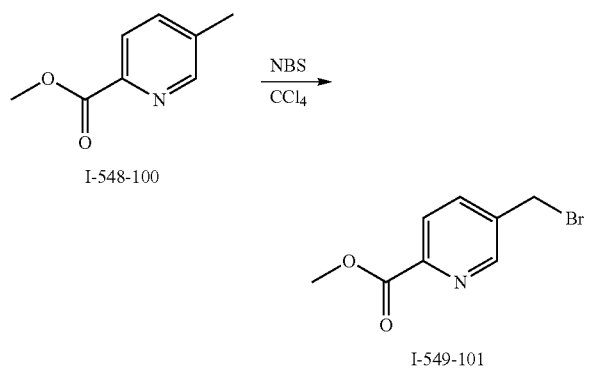

Example 9

Synthesis of I-548-102

Into a 50-mL round-bottom flask, was placed a solution of methyl 5-(bromomethyl)picolinate (500 mg, 2.09 mmol, 1.00 equiv, 96%) in acetonitrile (20 mL), 3-ethylphenol (280 mg, 2.29 mmol, 1.05 equiv), and potassium carbonate (900 mg, 6.51 mmol, 3.00 equiv). The resulting solution was stirred for 2 h at 85° C. The mixture was concentrated under vacuum. The residue was diluted with 30 mL of water and extracted with 2×20 mL of ethyl acetate and the organic layers combined and dried over anhydrous sodium sulfate and concentrated under vacuum. This resulted in 0.6 g (92%) of methyl 5-((3-ethylphenoxy)methyl)picolinate as a brown solid.

LC-MS: (ES, m/z): 272 [M+H]$^+$

Scheme 9. A synthetic route for preparing compound I-548-102.

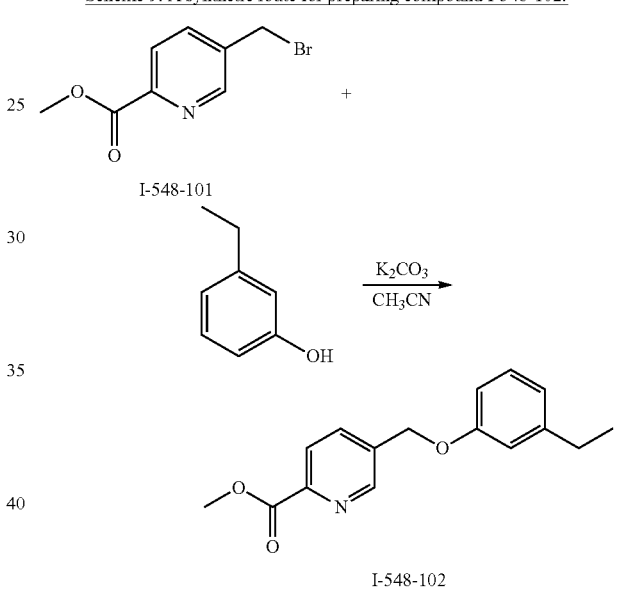

Example 10

Synthesis of I-548-0

Into a 500-mL round-bottom flask, was placed a solution of methyl 5-((3-ethylphenoxy)methyl)picolinate (8 g, 25.65 mmol, 1.00 equiv, 87%) in tetrahydrofuran/water (2:1) (200 mL) and lithium hydroxide hydrate (4.95 g, 117.86 mmol, 4.00 equiv). The resulting solution was stirred for 45 min at 40° C. The resulting mixture was concentrated under vacuum. The solids were collected by filtration. The pH value of the solid was adjusted to 6 with acetic acid. The solids were collected by filtration and dried in an oven under reduced pressure. This resulted in 4.55 g (67%) of 5-((3-ethylphenoxy)methyl)picolinic acid as a light yellow solid.

LC-MS: (ES, m/z): [M+H]$^+$ 258

1H-NMR: (400 MHz, DMSO-d6, ppm) δ 8.78 (s, 1H), 8.04 (m, 2H), 7.21 (m, 1H), 6.83 (m, 3H), 5.24 (s, 2H), 2.54 (m, 2H), 1.16 (m, 3H).

Scheme 10. A synthetic route for preparing compound I-548-0.

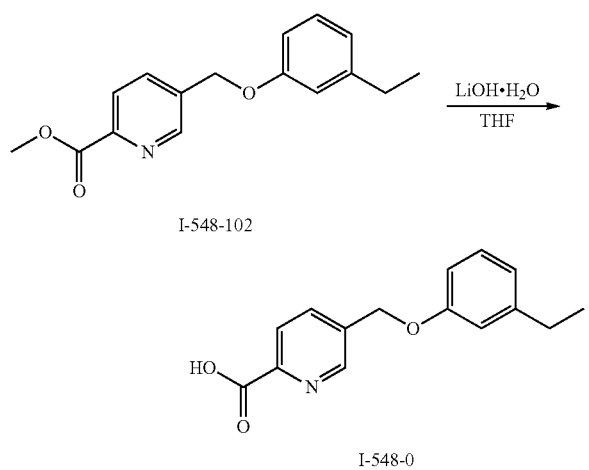

Example 11

Synthesis of I-544-0

Scheme 11. A synthetic route for preparing compound I-554-0.

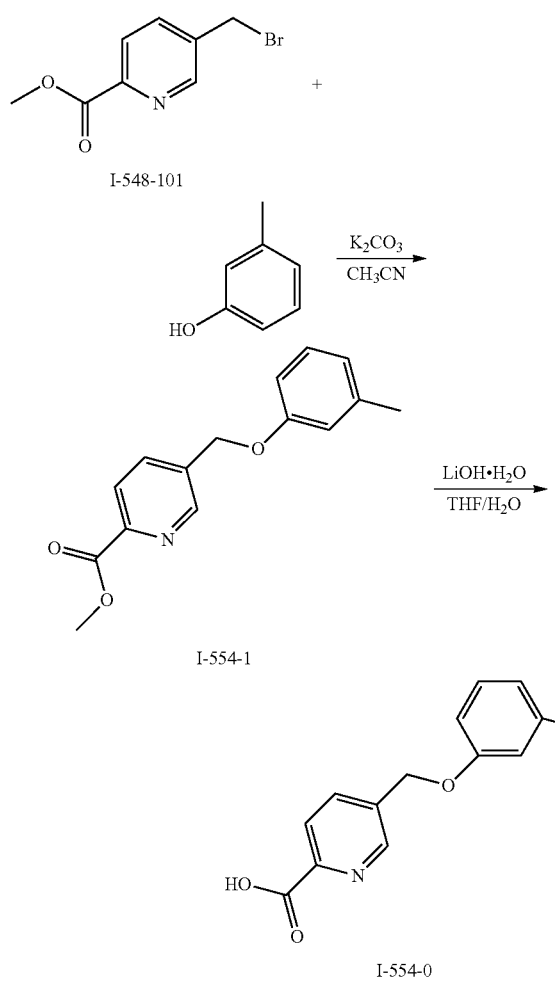

Example 12

Synthesis of I-554-1

Into a 50-mL round-bottom flask, was placed a solution of methyl 5-(bromomethyl)picolinate (500 mg, 2.17 mmol, 1.00 equiv) in $CH_3CN$ (25 mL), m-cresol (250 mg, 2.31 mmol, 1.05 equiv), and potassium carbonate (900 mg, 6.52 mmol, 3.00 equiv). The solution was heated to reflux for 2 h in an oil bath. The resulting mixture was concentrated under vacuum and diluted with 50 mL of $H_2O$. The resulting solution was extracted with 3×20 mL of ethyl acetate and the organic layers combined and dried over anhydrous sodium sulfate and concentrated under vacuum. This resulted in 0.6 g (89%) of methyl 5-(m-tolyloxymethyl)picolinate as a brown solid.

LC-MS: (ES, m/z): $[M+H]^+$ 258

Scheme 12. A synthetic route for preparing compound I-554-1.

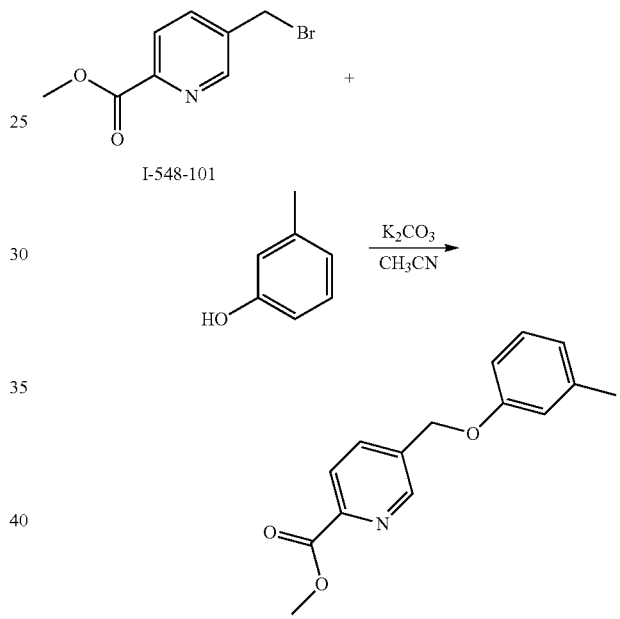

Example 13

Synthesis of I-554-0

Into a 250-mL round-bottom flask, was placed a solution of methyl 5-(m-tolyloxymethyl)picolinate (8.7 g, 33.85 mmol, 1.00 equiv) in tetrahydrofuran/$H_2O$ (50 ml/50 mL), and $LiOH.H_2O$ (5.6 g, 133.33 mmol, 4.00 equiv). The resulting solution was stirred for 30 min at 50° C. in an oil bath. The resulting mixture was concentrated under vacuum. The solids were collected by filtration. The pH value of the solid was adjusted to 2~3 with acetic acid (30%). The solids were collected by filtration and dried in an oven under reduced pressure. This resulted in 4.85 g (57%) of 5-(m-tolyloxymethyl)picolinic acid as a white solid.

LC-MS: (ES, m/z): 244 $[M+H]^+$

1H-NMR: (300 MHz, $CDCl_3$, ppm) δ 2.370 (s, 3H), 5.206 (s, 2H), 6.829 (m, 3H), 7.224 (t, 1H), 8.045 (m, 1H), 8.263 (d, 1H), 8.720 (s, 1H)

Scheme 13. A synthetic route for preparing compound I-554-0.

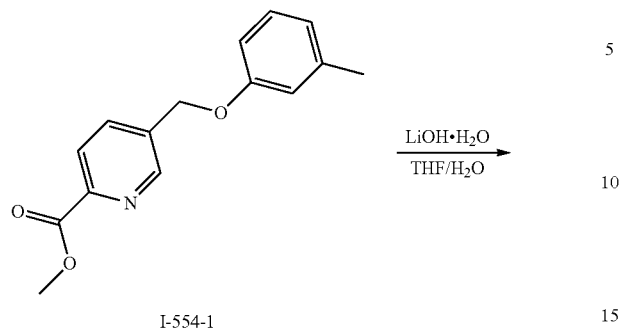

Example 14

Synthesis of I-546-0

Scheme 14. A synthetic route for preparing compound I-546-0.

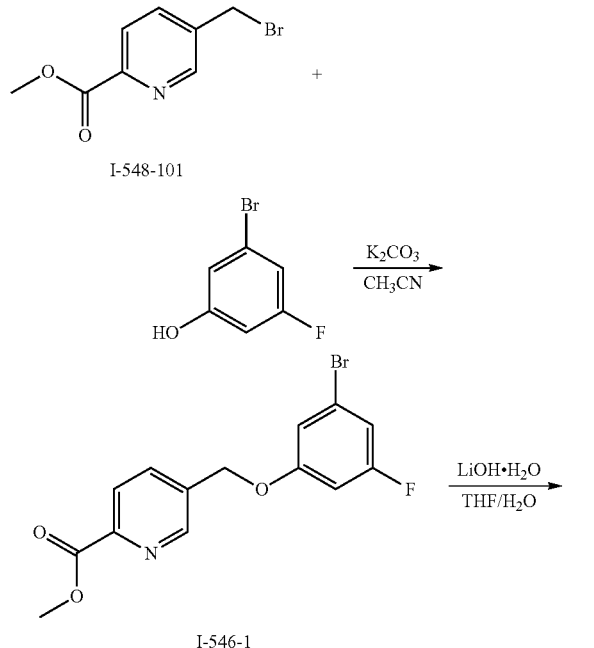

Example 15

Synthesis of I-546-1

Into a 50-mL round-bottom flask, was placed methyl 5-(bromomethyl)picolinate (500 mg, 2.17 mmol, 1.00 equiv), 3-bromo-5-fluorophenol (440 mg, 2.30 mmol, 1.06 equiv), CH$_3$CN (6 mL), and potassium carbonate (900 mg, 6.52 mmol, 3.00 equiv). The resulting solution was stirred for 60 min at 85° C. The mixture was concentrated under vacuum and the residue was diluted with 20 mL of H$_2$O. The resulting solution was extracted with 3×20 mL of ethyl acetate and the organic layers combined and dried over anhydrous sodium sulfate. The solids were filtered out. The resulting mixture was concentrated under vacuum. This resulted in 0.62 g (77%) of methyl 5-((3-bromo-5-fluorophenoxy)methyl)picolinate as a yellow solid.

LC-MS: (ES, m/z): 342 [M+H]$^+$

Scheme 15. A synthetic route for preparing compound I-546-1.

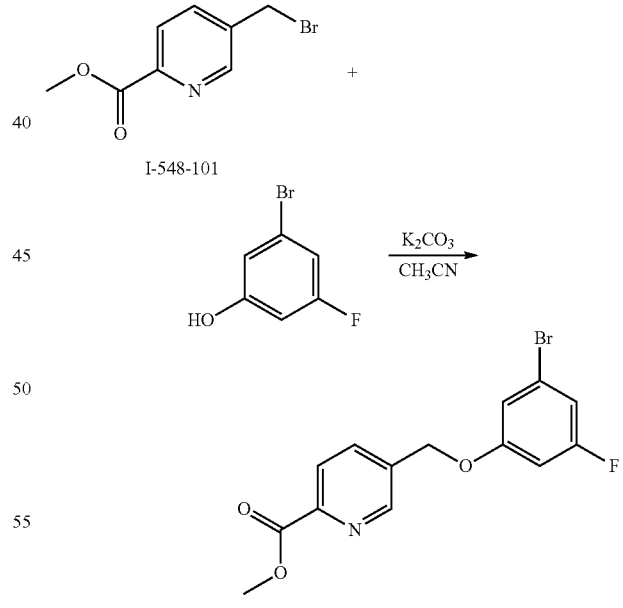

Example 16

Synthesis of I-546-0

Into a 250-mL round-bottom flask, was placed methyl 5-((3-bromo-5-fluorophenoxy)methyl)picolinate (9.2 g, 27.05 mmol, 1.00 equiv), tetrahydrofuran (100 mL), water (30 mL), and LiOH·H₂O (3.41 g, 81.19 mmol, 3.00 equiv). The resulting solution was stirred for 60 min at 45° C. The resulting mixture was concentrated under vacuum. The residue was diluted with 200 mL of H₂O. The pH value of the solution was adjusted to 5-6 with acetic acid. The solids were collected by filtration and washed with 2×100 mL of petroleum ether. The solid was dried in an oven under reduced pressure. This resulted in 7.37 g (82%) of 5-((3-bromo-5-fluorophenoxy)methyl)picolinic acid as a yellow solid.

LC-MS: (ES, m/z): 326 [M+H]⁺

1H-NMR: (300 MHz, CDCl₃, ppm) δ 5.186 (s, 2H), 6.687 (m, 1H), 6.962 (m, 2H), 8.030 (m, 1H), 8.316 (d, 1H), 8.716 (s, 1H)

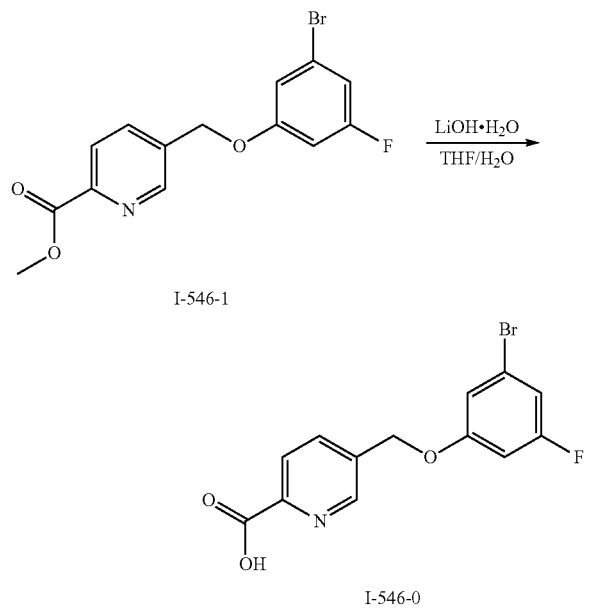

Example 17

Synthesis of I-549-0

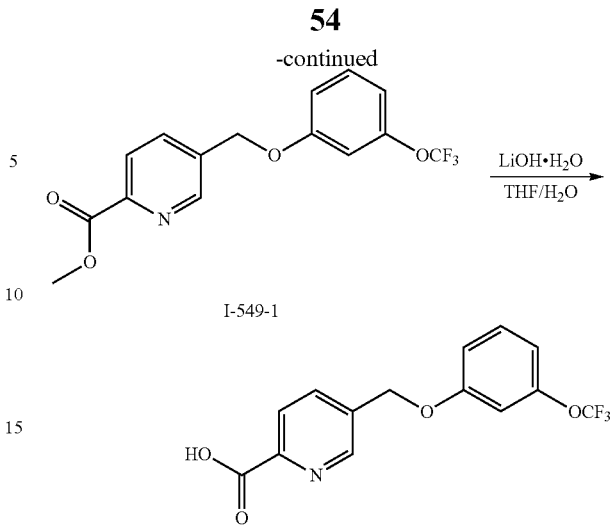

Example 18

Synthesis of I-549-1

Into a 50-mL round-bottom flask, was placed methyl 5-(bromomethyl)picolinate (500 mg, 2.17 mmol, 1.00 equiv), 3-(trifluoromethoxy)phenol (410 mg, 2.30 mmol, 1.06 equiv), CH₃CN (6 mL), and potassium carbonate (900 mg, 6.52 mmol, 3.00 equiv). The resulting solution was stirred for 30 min at 85° C. in an oil bath. The resulting mixture was concentrated under vacuum. The residue was diluted with 20 mL of H₂O and extracted with 2×20 mL of ethyl acetate and the organic layers combined and dried over anhydrous sodium sulfate. The solids were filtered out. The filtrate was concentrated under vacuum. This resulted in 0.56 g (74%) of methyl 5-((3-(trifluoromethoxy)phenoxy)methyl)picolinate as a yellow-tan solid.

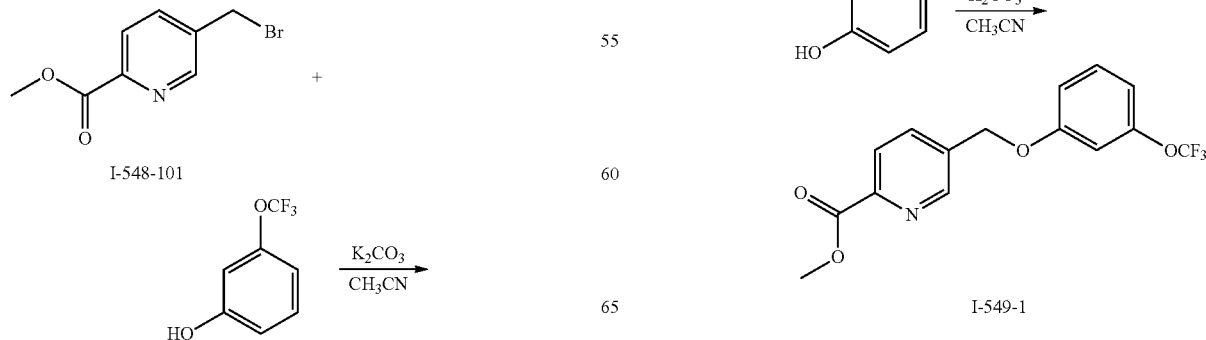

Example 19

Synthesis of I-549-0

Into a 500-mL round-bottom flask, was placed methyl 5-((3-(trifluoromethoxy)phenoxy)methyl)picolinate (8.2 g, 25.05 mmol, 1.00 equiv), tetrahydrofuran (100 mL), water (20 mL) and LiOH.H$_2$O (4.20 g, 4.00 equiv). The resulting solution was stirred for 1 h at 45° C. The reaction mixture was concentrated under vacuum. The resulting solution was diluted with 50 mL of H$_2$O. The pH value of the solution was adjusted to 5-6 with acetic acid. The solids were collected by filtration and washed with 2×100 mL of petroleum ether. The solid was dried in an oven under reduced pressure. This resulted in 7.09 g (90%) of 5-((3-(trifluoromethoxy)phenoxy)methyl)picolinic acid as a light yellow solid.

LC-MS: (ES, m/z): 314 [M+H]$^+$ $^1$H-NMR: (300 MHz, CDCl$_3$, ppm) δ 5.200 (s, 2H), 6.904 (t, 3H), 7.351 (t, 1H), 8.028 (d, 1H), 8.297 (d, 1H), 8.735 (s, 1H).

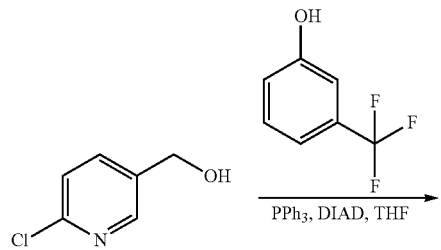

Scheme 19. A synthetic route for preparing compound I-549-0.

Schemes 20-23 depict synthetic routes to yield carboxylic acid I-475-0 and ester I-475-3 containing derivatives via 6-chloro-3-pyridinemethanol. The derivatives are useful for preparing compounds of formula I.

Example 20

Synthesis of I-475-0

Scheme 20. A synthetic route for preparing compound I-475-0.

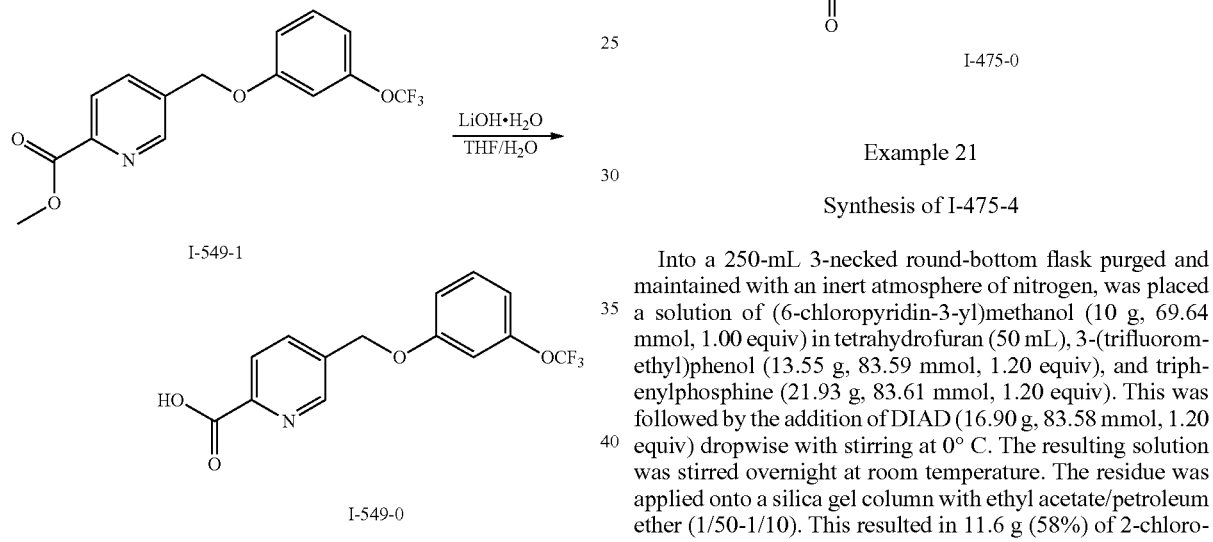

Example 21

Synthesis of I-475-4

Into a 250-mL 3-necked round-bottom flask purged and maintained with an inert atmosphere of nitrogen, was placed a solution of (6-chloropyridin-3-yl)methanol (10 g, 69.64 mmol, 1.00 equiv) in tetrahydrofuran (50 mL), 3-(trifluoromethyl)phenol (13.55 g, 83.59 mmol, 1.20 equiv), and triphenylphosphine (21.93 g, 83.61 mmol, 1.20 equiv). This was followed by the addition of DIAD (16.90 g, 83.58 mmol, 1.20 equiv) dropwise with stirring at 0° C. The resulting solution was stirred overnight at room temperature. The residue was applied onto a silica gel column with ethyl acetate/petroleum ether (1/50-1/10). This resulted in 11.6 g (58%) of 2-chloro-5-((3-(trifluoromethyl)phenoxy)methyl)pyridine as a white solid.

Scheme 21. A synthetic route for preparing compound I-475-4.

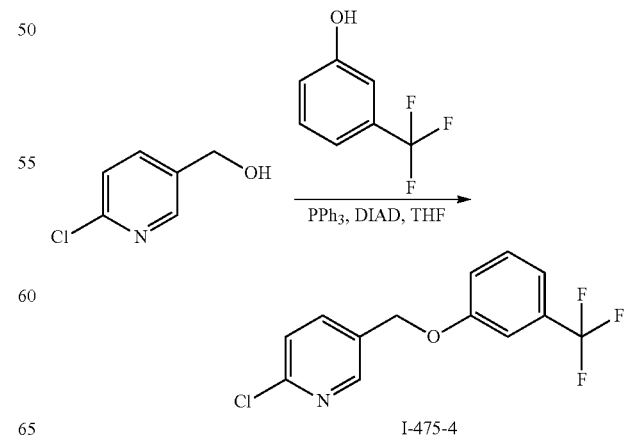

Example 22

Synthesis of I-475-3

A 250-mL autoclave vessel was charged with a solution of 2-chloro-5-((3-(trifluoromethyl)phenoxy)methyl)pyridine (8.63 g, 30.00 mmol, 1.00 equiv), Pd(dppf)Cl2 (1.30 g, 1.81 mmol, 0.06 equiv), and triethylamine (6.07 g, 60.10 mmol, 2.00 equiv) in methanol (150 mL). The vessel was purged with nitrogen three times and carbon monoxide three times. The vessel was pressurized to 20 atm with carbon monoxide and heated to 100° C. The resulting solution was stirred for 5 h. The reaction mixture was cooled. The solids were filtered out. The filtrate was concentrated under vacuum. The residue was applied onto a silica gel column with ethyl acetate/petroleum ether (1/20-1/10). This resulted in 6 g (64%) of methyl 5-((3-(trifluoromethyl)phenoxy)methyl)picolinate as a white solid.

Scheme 22. A synthetic route for preparing compound I-475-3.

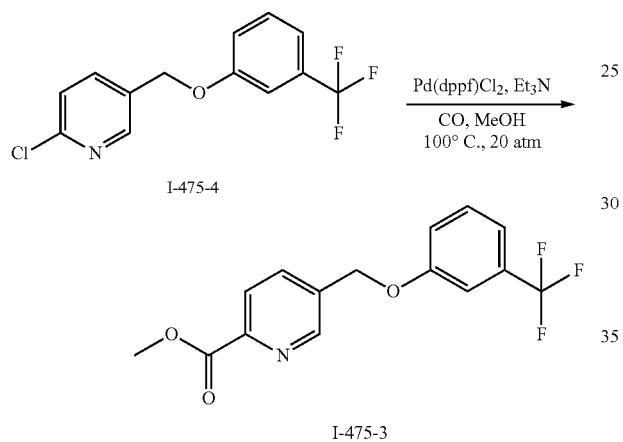

Example 23

Synthesis of I-475-0

Into a 500-mL round-bottom flask, was placed a solution of methyl 5-((3-(trifluoromethyl)phenoxy)methyl)picolinate (6.2 g, 19.92 mmol, 1.00 equiv) in tetrahydrofuran/H$_2$O (1:1) (100 mL). To this solution was added sodium hydroxide (925 mg, 23.12 mmol, 1.20 equiv). The resulting solution was stirred for 10 min at room temperature. The reaction mixture was concentrated under vacuum to remove THF. The resulting solution was extracted with 2×50 mL of ethyl acetate and the aqueous layer combined was adjusted pH value to 5-6 with hydrogen chloride aqueous (4.5 mL, 6 mol/L). White solid was formed. The suspension was stirred for 1 h further. The solids were collected by filtration. The solid was dried in an oven under reduced pressure. This resulted in 5.75 g (97%) of 5-((3-(trifluoromethyl)phenoxy)methyl)picolinic acid as a white solid.

LC-MS (ES, m/z): 298 [M+H]$^+$

1H-NMR: (400 MHz, DMSO, ppm): δ 13.36 (s, 1H), 8.82 (s, 1H), 8.11-8.06 (m, 2H), 7.59-7.55 (m, 1H), 7.39-7.33 (m, 3H), 5.37 (s, 2H)

19F-NMR: (376 MHz; DMSO-d6, ppm): −61.10 (s, 3F)

Scheme 23. A synthetic route for preparing compound I-475-0.

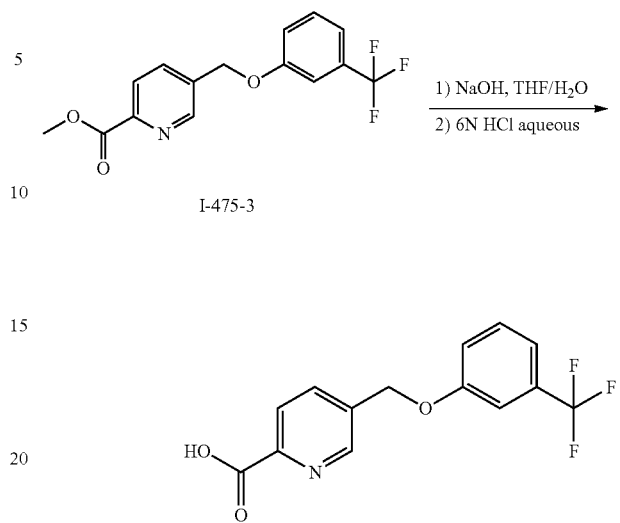

Example 24

Synthesis of Compound 125

To a solution of EDAC-HCl (1.5 eq, 0.15 mmol, 28 mg), HOBt (20 mg, 1.5 eq, 1.5 mmol), and NMM (19 uL, 1.5 eq, 0.15 mmol) were dissolved in DMF (0.5 mL) was added a solution of Ph-SN-546-0 (32 mg, 0.1 mmol) in DMF (0.5 mL). This mixture was added to a solution of isobutylamine (7.13 mg, 0.15 mmol, 1.5 eq) in DMF (0.5 mL). The reaction mixture was agitated overnight at room temperature. DMSO (500 uL) was added to the reaction mixture which was then concentrated. Additional DMSO (500 uL) was added to the reaction mixture which was then purified on a Gilson Prep HPLC system using Varian Pursuit XRs, C18, 50×21.4 mm, 10 u. Solvent A: HPLC Water, Solvent B: 10 mMol Ammonium Acetate in Methanol with 0.1% v/v Ammonium Hydroxide. Method ran from 40% B to 100% B over 5 minutes holding at 100% B for 1 minute at 28 mL/min.

Scheme 24. A synthetic route for preparing compound 125.

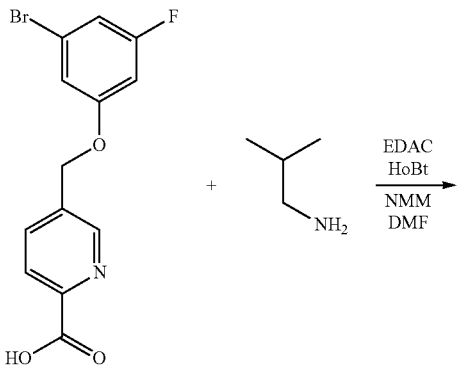

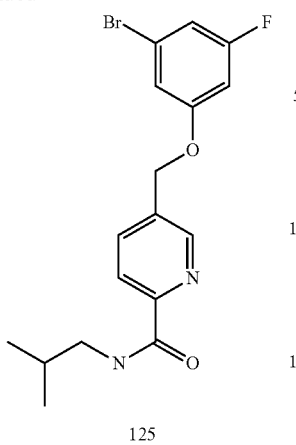
125
The above synthetic route can be used to prepare compounds of formula I. Using this route, the following compounds of formula I were prepared: 4, 5, 10, 24, 28, 33, 37, 41, 44, 47, 49, 54, 56, 63, 65, 68, 70, 73, 76, 77, 78, 124, 125, 127, 129, 130 and 132.
Example 25
Synthesis of Ethylene-Type Linker Compounds
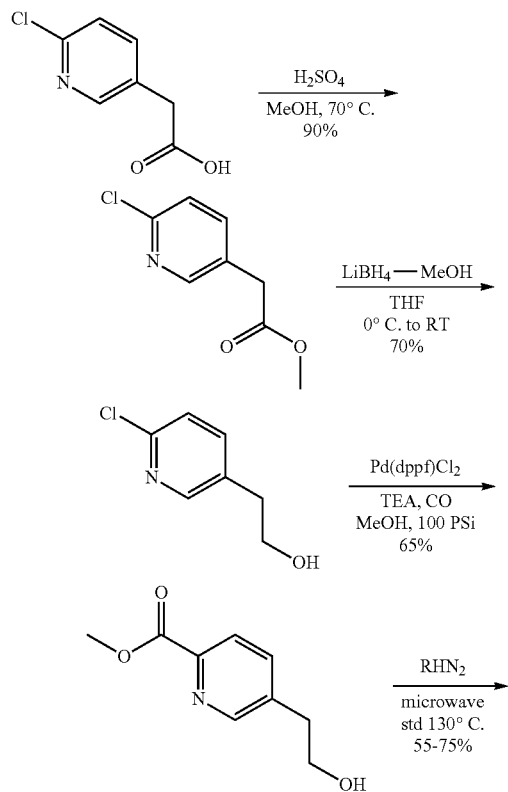
Example 26
Synthesis of Benzylic-Type Linker Compounds
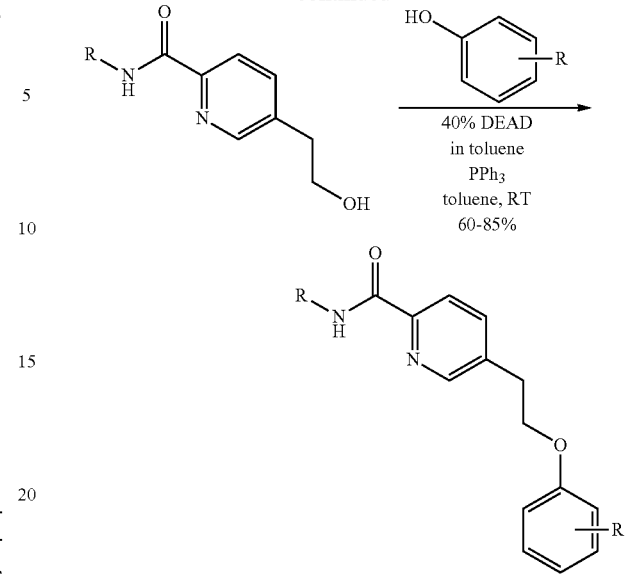
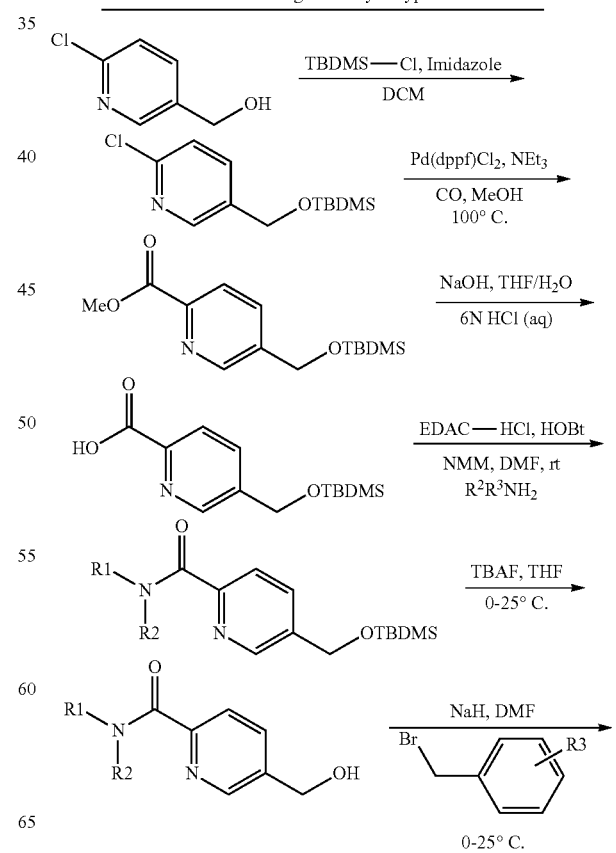

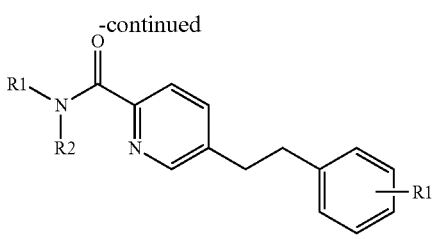

Example 27

Synthesis of 5-(2-hydroxyethyl)-2-pyridineacetic acid methyl ester (I-087)

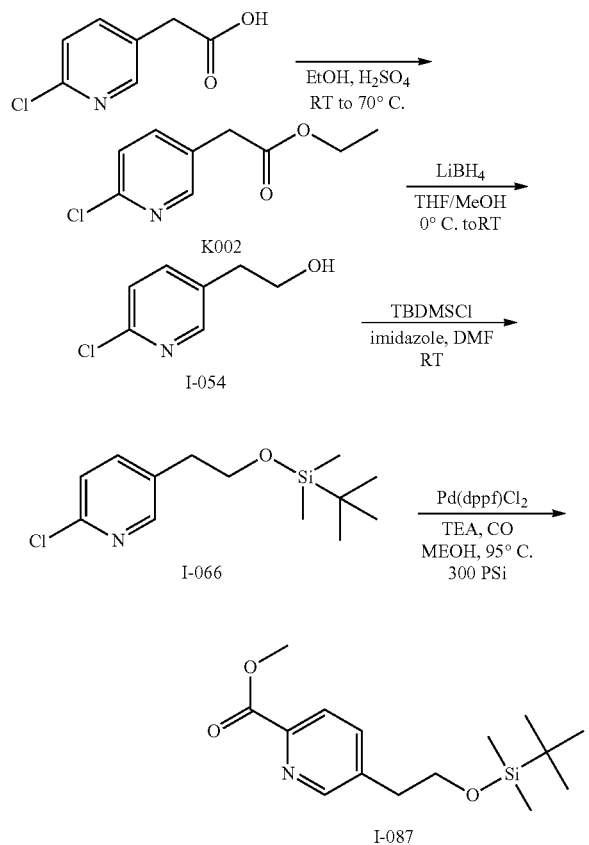

Scheme 27 depicts a synthetic route to prepare intermediate compounds useful for the preparation of compounds of formula I.

Example 28

Synthesis of K002

To a suspension of 6-chloro-2-pyridineacetic acid methyl ester (10 g, 58.2 mmol) was added conc. sulfuric acid (30 mL) and the reaction was heated to 70° C. for 4 hr. The reaction mixture was cooled to room temperature and concentrated and the resulting residue was suspended in H₂O (1 L) and pH was adjusted to pH=9 with sodium carbonate. The solution was extracted with ethyl acetate. The organics were washed with brine, dried over Na₂SO₄, filtered and concentrated to give the crude product that was purified by flash column chromatography (30% EtOAC: 70% heptanes) to give the desired product 8.58 g, 79%.

LC-MS: (ES, m/z): 186 [M+H]$^+$ $^1$H-NMR: (400 MHz, MeCN-d3, ppm): δ 3.66 (m, 5H), 7.36 (d, 1H), 7.67 (d, 1H), 8.26 (s, 1H).

Example 29

Synthesis of I-054

A solution of K002 (19.34 g, 104.17 mmol) in THF/MeOH (100 mL/10 mL) was cooled to 0° C. and LiBH4 (4.76 g, 215.64 mmol) was added. The reaction mixture was warmed to room temperature and allowed to stir overnight. To quench, the reaction was cooled to ° C. and sat. NH₄Cl solution (500 mL) was added. The pH was adjusted to pH=7 through addition of solid NH₄Cl. The aqueous mixture was extracted with ethyl acetate and the organic layer was dried with MgSO₄, filtered and concentrated. The crude material was purified by flash column chromatography to give the desired product (1.51 g, 70%) as a clear oil.

$^1$H-NMR: (400 MHz, CDCl₃, ppm): δ 2.78 (t, 2H), 3.81 (m, 2H), 7.2 (d, 1H), 7.48 (d, 1H), 8.17 (s, 1H).

Example 30

Synthesis of I-066

To a solution of I-054 (1.0 g, 6.33 mmol) in DMF (2 mL) was added imidazole (0.94 g, 13.8 mmol) and tert-butyldimethylsilyl chloride (1.25 g, 8.28 mmol). The reaction mixture was stirred at room temperature overnight and the concentrated. The resulting residue was partitioned between ethyl acetate and water and extracted. The organics were dried (MgSO₄), filtered and concentrated. The crude material was purified by flash column chromatography to give the desired compound (1.80 g, 99%) as a clear oil.

$^1$H-NMR: (400 MHz, CDCl₃, ppm): δ 0.1 (s, 6H), 0.88 (s, 9H) 2.83 (t, 2H), 3.81 (t, 2H), 7.28 (d, 1H), 7.54 (d, 1H), 8.27 (s, 1H).

Example 31

Synthesis of I-087

Into a 40-mL high pressure reactor, was placed I-066 (4.28 g, 15.79 mmol), methanol (14 mL), triethylamine (3.3 mL, 23.69 mmol), and Pd(dppf)Cl₂ (1.16 g). To the above CO (g) was introduced at 300 psi pressure. The resulting solution was stirred overnight at 96° C. The resulting mixture was cooled and filtered through a pad of Celite® and the filtrate was concentrated under vacuum. The residue was applied onto a silica gel pad with heptanes/ethyl acetate. This resulted in 4.6 g (99%) of desired product.

$^1$H-NMR: (400 MHz, CDCl₃, ppm): δ 0.1 (s, 6H), 0.89 (s, 9H) 2.93 (t, 2H), 3.89 (t, 2H), 4.05 (s, 3H), 7.73 (d, 1H), 8.10 (d, 1H), 8.65 (s, 1H).

Example 32

Synthesis of Compound 206

Scheme 28 depicts a synthetic route to prepare compound 206.

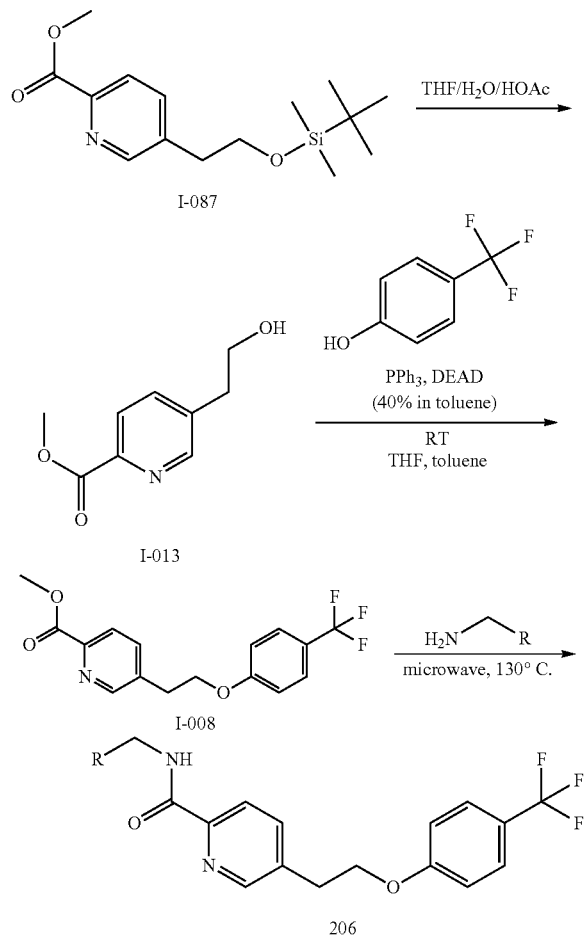

Example 33

Synthesis of I-013

A solution of I-087 (3.54 g, 12 mmol) in THF/H$_2$O/HOAc (20 mL/20 mL/60 mL) was stirred at room temperature overnight. The reaction mixture was concentrated to give the desired product 1.92 g, (91%).

$^1$H-NMR: (400 MHz, CDCl$_3$, ppm): δ 2.88 (t, 2H), 3.85 (t, 2H), 3.93 (s, 3H), 7.68 (d, 1H), 7.99 (d, 1H), 8.54 (s, 1H).

Example 34

Synthesis of I-008

A 100 mL round-bottom flask was charged with 4-trifluoromethylphenol (0.17 g, 1.05 mmol), triphenylphosphine (0.18 g, 1.05 mmol) and toluene (3 mL). A solution of I-013 (0.19 g, 1.05 mmol) in toluene/THF (2 mL/7 mL) was added and stirred for 10 mins at which time a solution of diethyl azodicarboxylate (0.53 mL of 40% (v/v) solution in toluene, 1.15 mmol) was added and the reaction mixture was stirred at room temperature overnight. The reaction mixture was concentrated and the residue purified by reverse phase HPLC using a Gilson Prep HPLC system using Varian Pursuit XRs, C18, 50×21.4 mm, 10 u. Solvent A: HPLC Water, Solvent B: Methanol. The method ran from 40% B to 100% B over 5 minutes holding at 100% B for 2 minute at 28 mL/min. The appropriate fractions were concentrated to give the desired product, 200 mg (59%).

$^1$H-NMR: (400 MHz, CDCl$_3$, ppm): δ 3.13 (t, 2H), 3.94 (s, 3H), 4.19 (t, 2H), 6.86 (d, 2H), 7.45 (d, 2H), 7.73 (d, 1H), 8.04 (d, 1H), 8.63 (s, 1H).

Example 35

Synthesis of Compound 206

A microwave vial was charged with I-008 (0.032 g, 0.1 mmol) and iso-butylamine (1 mL). The reaction mixture was heated for 3 hrs at 120° C. and 75 W. The reaction mixture was concentrated, re-dissovled in methanol (3 mL) and purified by reverse phase HPLC using a Gilson Prep HPLC system using Varian Pursuit XRs, C18, 50×21.4 mm, 10 u. Solvent A: HPLC Water, Solvent B: Methanol. The method ran from 40% B to 100% B over 5 minutes holding at 100% B for 2 minute at 28 mL/min. The appropriate fractions were concentrated to give the desired product, 27 mg (74%).

LC-MS (ES, m/z): 367 [M+H]$^+$ $^1$H-NMR: (400 MHz, CDCl$_3$, ppm): δ 0.93 (d, 6H), 1.85 (m, 1H), 3.11 (t, 2H), 3.23 (t, 2H), 4.18 (t, 2H), 6.88 (d, 2H) 7.71 (d, 2H), 8.01 (br. t, 1H), 8.42 (s, 1H).

These specific compounds of formula I, as well as other compounds of formula I, were prepared using the chemistry described above: 47, 219, 220, 221, 209, 9, 12, 13, 14, 15, 132, 133, 134, 135, 140, 205, 47, 138, 222, 225, 223, 237, 238, 240, 241, 242, 243, 275, 278, and 279.

Example 36

Synthesis of Compounds Useful for Preparing Compounds of Formula I

Scheme 29 depicts a synthetic route for compounds useful for preparing compounds of formula I.

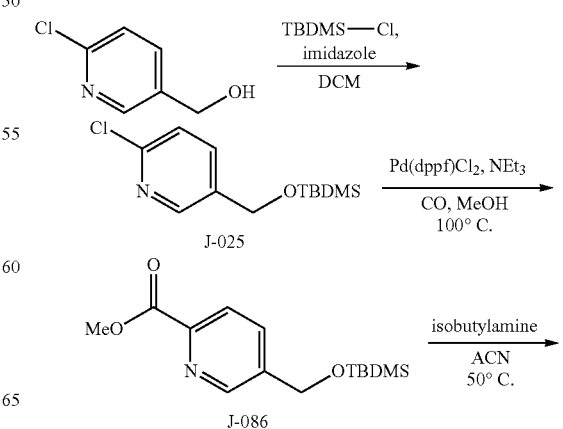

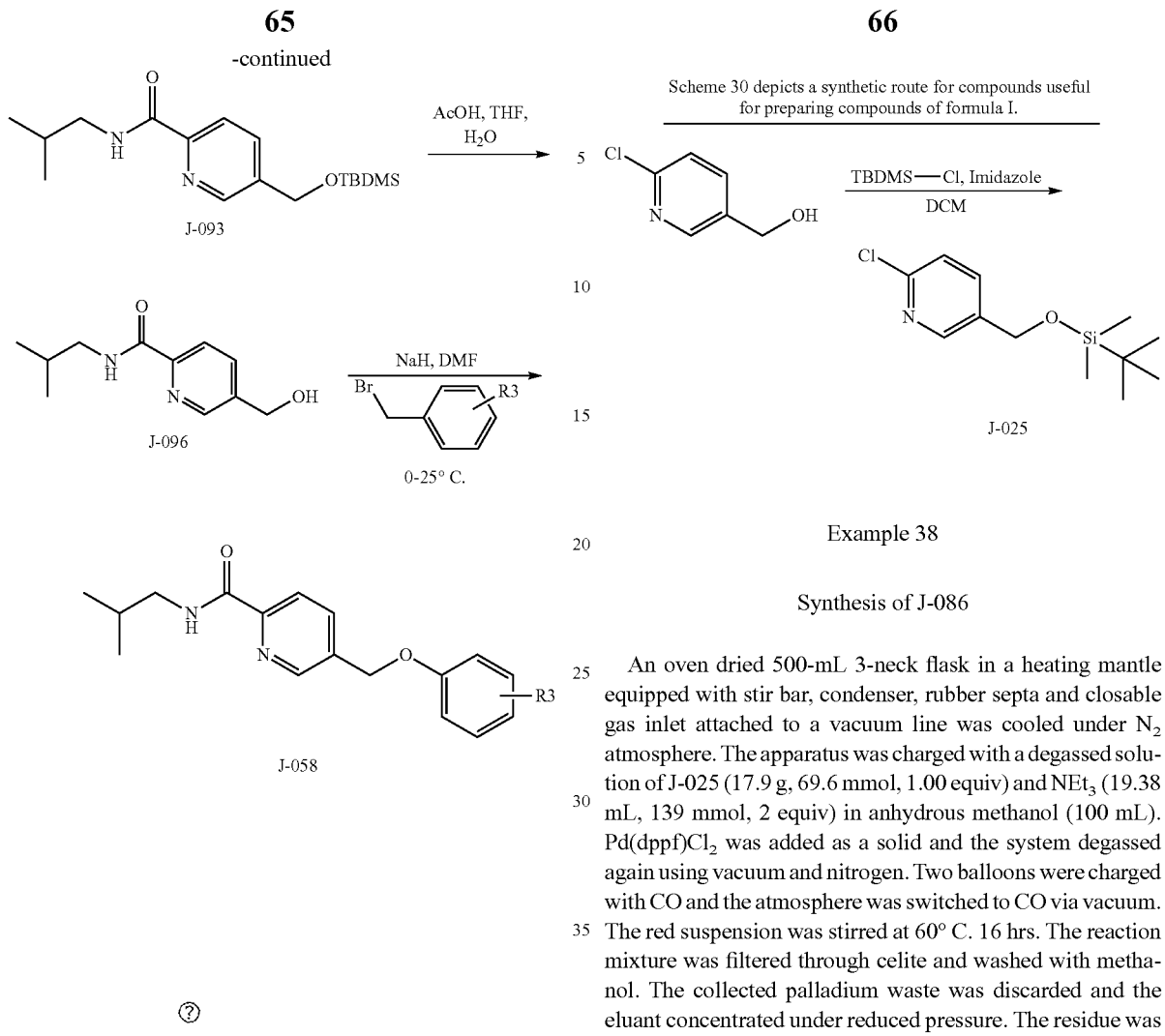

Example 37

Synthesis of J-025

In a 200 mL round-bottom flask, was placed a solution of 2-chloro-5-hydroxymethylpyridine (10 g, 69.6 mmol, 1.00 equiv) in anhydrous dimethylformamide (70 mL). Imidazole (11.85 g, 174 mmol, 2.5 equiv) was added all at once as a solid. Once dissolved a dropping funnel was added and a solution of tert-butyldimethylsilyl chloride (15.75 g, 104 mmol, 1.5 equiv) in anhydrous dimethylformamide (30 mL) was added over a 5 minute period. The solution was stirred 16 hr at ambient temperature. The resulting mixture was poured into water (250 mL), stirred 5 minutes and extracted into ethyl acetate (3×200 mL). The organic layers were combined, washed with brine (100 mL), dried (Na$_2$SO$_4$), filtered and concentrated to a clear oil. The oil was dried under reduced pressure to yield the desired product (J-025, 17.9 g, quantitative).

LC-MS-J-025: (ES, m/z): 257 [M+H]$^+$

1H-NMR-J-025: (400 MHz, CDCl$_3$, ppm): δ 8.23 (s, 1H), 7.53-7.51 (m, 1H), 7.20-7.18 (m, 1H), 4.62 (s, 2H), 0.83 (s, 9H), 0.00 (s, 6H)

Example 38

Synthesis of J-086

An oven dried 500-mL 3-neck flask in a heating mantle equipped with stir bar, condenser, rubber septa and closable gas inlet attached to a vacuum line was cooled under N$_2$ atmosphere. The apparatus was charged with a degassed solution of J-025 (17.9 g, 69.6 mmol, 1.00 equiv) and NEt$_3$ (19.38 mL, 139 mmol, 2 equiv) in anhydrous methanol (100 mL). Pd(dppf)Cl$_2$ was added as a solid and the system degassed again using vacuum and nitrogen. Two balloons were charged with CO and the atmosphere was switched to CO via vacuum. The red suspension was stirred at 60° C. 16 hrs. The reaction mixture was filtered through celite and washed with methanol. The collected palladium waste was discarded and the eluant concentrated under reduced pressure. The residue was slurried in warm toluene (15 mL) and loaded onto a large (350 g) silica plug in a glass fritted funnel inserted into an erlenmeyer flask attached to vaccuum. The desired product was purified by collecting 500 mL fractions from the following sequence passing over the plug using vacuum (500 mL heptanes, 1 L×10% EtOAc-Heptanes, 2 L×15% EtOAc-Heptanes, 1 L×20% EtOAc-Heptanes, 1 L×20% EtOAc-Heptanes). After concentrating the oil was dried under reduced pressure to yield the desired product (J-086, 16.4 g, 84%).

LC-MS-J-086: (ES, m/z): 283 [M+H]$^+$

1H-NMR-J-086: (400 MHz, CDCl$_3$, ppm): δ 8.75 (s, 1H), 8.01-7.99 (m, 1H), 7.70-7.69 (m, 1H), 4.72 (s, 2H), 3.89 (s, 3H), 0.83 (s, 9H), 0.00 (s, 6H)

Scheme 31 depicts a synthetic route for compound J-086, a useful compound for preparing compounds of formula I.

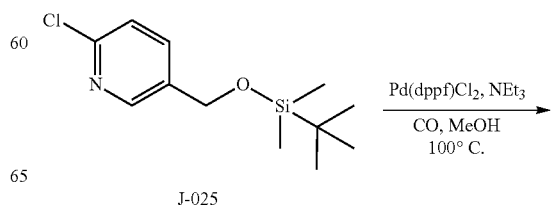

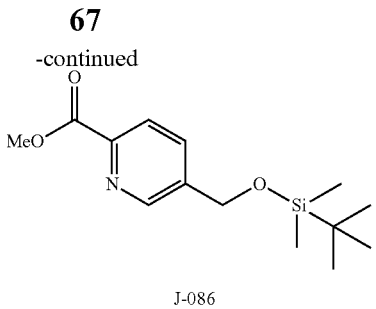

J-086

Example 39

Synthesis of J-093

In a 200 mL round-bottom flask, was placed a solution of J-086 (16.4 g, 58.2 mmol, 1.00 equiv) in acetonitrile (40 mL). Isobutylamine (25 mL, 251 mmol, 4 equiv) was added and the solution heated at 50° C. 48 hrs. The solution was concentrated to a yellow oil under reduced pressure, diluted with toluene (10 mL) and loaded onto a silica column (120 g, 0.5-20% EtOAc-heptanes gradient over 26 minutes). The desired fractions were combined, concentrated and the oil was dried under reduced pressure to yield the desired product as a white low melting solid (J-093, 15.92 g, 85%).

LC-MS-J-093: (ES, m/z): 323 [M+H]$^+$

1H-NMR-J-093: (400 MHz, CDCl$_3$, ppm): δ 8.38 (s, 1H), 8.06-8.04 (m, 1H), 7.99 (b, 1H), 7.67-7.65 (m, 1H), 4.69 (s, 2H), 3.18 (m, 3H), 1.81 (m, 1H), 0.87-0.83 (m, 15H), 0.00 (s, 6H)

Scheme 32 depicts a synthetic route for compound J-086, a useful compound for preparing compounds of formula I.

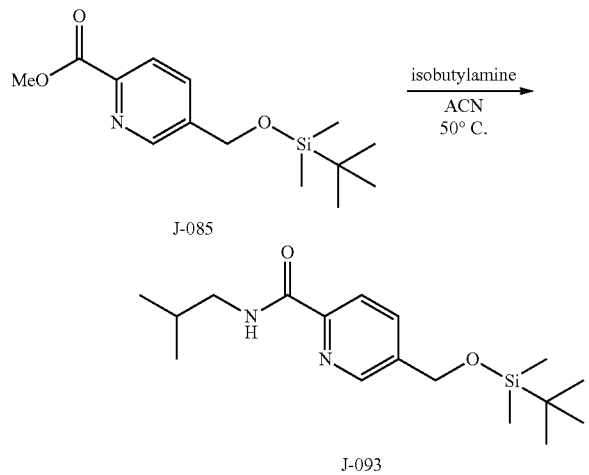

Example 40

Synthesis of J-096

In a 200-mL round-bottom flask, was placed a solution of J-096 (15.92 g, 49.44 mmol, 1.00 equiv) in tetrahydrofuran (20 mL). Acetic acid (40 mL) and water (20 mL) were added and the solution stirred at ambient temperature 16 hrs. The solution was concentrated to a yellow oil under reduced pressure. Then azeotroped 6× with toluene/methanol (100 mL (1:1)) and placed on a high vacuum pump to yield the desired product as an oil (J-096, 10.2 g, quantitative).

LC-MS-J-093: (ES, m/z): 209 [M+H]$^+$

1H-NMR-J-093: (400 MHz, CDCl$_3$, ppm): δ 8.50 (s, 1H), 8.10-8.08 (m, 2H), 7.80-7.78 (m, 1H), 4.77 (s, 2H), 3.27 (t, J=6.5×2, 2H), 1.89 (m, 1H), 0.96 (d, J=6.6, 6H)

Scheme 33 depicts a synthetic route for compound J-096, a useful compound for preparing compounds of formula I.

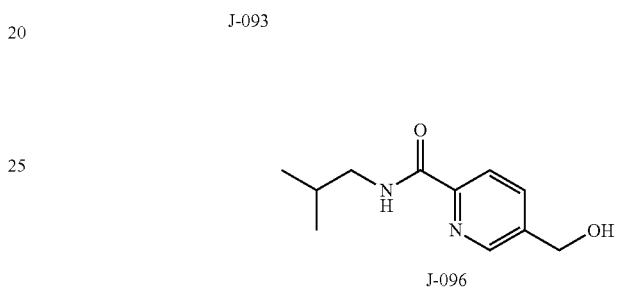

Example 41

Synthesis of Compound 227

Anhydrous dimethylformamide (1 mL) was placed in a 40 mL vial with stir bar and cooled in a metal reaction block in the refrigerator. A solution of J-096 (80 mg, 0.38 mmol, 1.00 equiv) in anhydrous dimethylformamide (2 mL) was placed in a vial and cooled in the refrigerator. (4-Chloro-3-trifluoromethoxy)benzylbromide (143 mg, 0.50 mmol, 1.3 equiv) was dissolved in anhydrous dimethylformamide (1 mL) and cooled in the refrigerator. NaH (12 mg, 0.50 mmol, 1.3 equiv) was added to the cold 40 mL vial via a glass pipette. The contents were swirled and the alcohol solution was added via pipette. The suspension was swirled again and the reaction block returned to the refrigerator. After 30 minutes, the block was removed, the bromide solution added via pipette and the reaction block placed at ambient temperature on a stir plate 16 hrs. Water was added (4 mL) to quench the reaction. The product was extracted into EtOAc and concentrated under reduced pressure. Heptanes (1 mL) and acetonitrile/methanol (3 mL (1:1)) were added and shook and the methanolic layer removed and shot onto the chromeleon HPLC (UV detector, MeOH/H$_2$O, method: 607-28). Concentration of the desired peaks resulted in the desired product (compound 227, 47 mg, 30%).

LC-MS-227: (ES, m/z): 414 [M+H]$^+$

1H-NMR-227: (400 MHz, CDCl$_3$, ppm): δ 8.49 (m, 1H), 8.17 (dd, J=8 and 0.6, 1H), 8.08 (b, 1H), 7.80 (dd, J=8 and 2.1, 1H), 7.43 (d, J=8.2, 1H), 7.31 (s, 1H), 7.21 (m, 1H), 4.61 (s, 2H), 4.55 (s, 2H), 3.28 (t, J=6.5×2, 2H), 1.89 (m, 1H), 0.96 (d, J=6.6, 6H).

Scheme 34 depicts a synthetic route for compound 227.

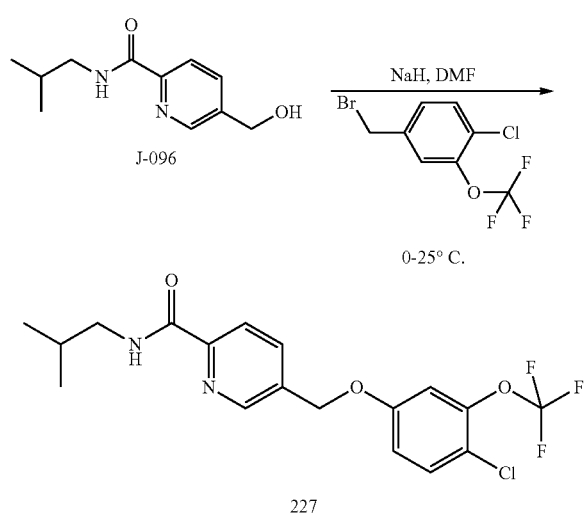

These specific compounds of formula I, as well as other compounds of formula I, were prepared using the chemistry described above: 227, 228, 229, 232, 234, 216, 228, 256, 257, 258, 259, 260, 263, 264, 266, 268 and 270.

It will be appreciated by persons skilled in the art that, within aspect of the processes described above; the order of the synthetic steps employed may be varied and will depend inter alia on factors such as the nature of other functional groups present in a particular substrate, the availability of key intermediates, and the protecting group strategy (if any) to be adopted (see e.g. "Protective Groups in Organic Synthesis (Fourth Edition)", eds. Peter G. M. Wuts and Theodora W. Greene, Wiley-Interscience Publishers, (2007)). Clearly, such factors will also influence the choice of reagents for use in the said synthetic steps.

The invention further contemplates separating the enantioners in whole or in part of the present invention or synthesizing enantiomerically enriched compounds of the invention. The composition may be prepared by separating the enantioners in whole or in part by standard methods, for example by chemical resolution using optically active acid or by use of column chromatography or reverse-phase column chromatography using a substantially optically active (or "chiral") stationary phase as known to those skilled in the art. The formation and/or isolation of specific enantiomers of a compound is not routine, and there are no general methods that may be used to obtain specific enantiomers of all compounds. The methods and conditions used to obtain specific enantiomers of a compound must be determined for each specific compound.

Table 1 below shows specific compounds of formula I.

TABLE 1

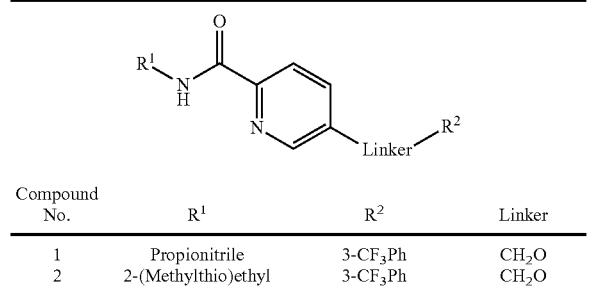

| Compound No. | $R^1$ | $R^2$ | Linker |
|---|---|---|---|
| 1 | Propionitrile | 3-$CF_3$Ph | $CH_2O$ |
| 2 | 2-(Methylthio)ethyl | 3-$CF_3$Ph | $CH_2O$ |

TABLE 1-continued

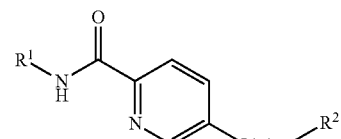

| Compound No. | $R^1$ | $R^2$ | Linker |
|---|---|---|---|
| 3 | MeS$(CH_2)_3$ | 3-$CF_3$Ph | $CH_2O$ |
| 4 | Cyclopropanemethyl | 3-$CF_3$Ph | $CH_2O$ |
| 5 | i-Bu | 3-$CF_3$Ph | $CH_2O$ |
| 6 | n-Bu | 3-$CF_3$Ph | $CH_2O$ |
| 7 | Propionitrile | 3-$CF_3$Ph | $CH(CH3)O$ |
| 8 | 1-naphthalenemethyl | 3-$CF_3$Ph | $CH_2O$ |
| 9 | i-Bu | 3-$C_3$OPh | $CH_2O$ |
| 10 | i-Bu | 4-$C_3$OPh | $CH_2O$ |
| 11 | iBu | 2-$C_3$OPh | $CH_2O$ |
| 12 | i-Bu | 3-$C_3$OPh | CH2CH2O |
| 13 | i-Bu | 4-$C_3$OPh | CH2CH2O |
| 14 | CH2THP | 4-$C_3$OPh | CH2CH2O |
| 15 | CH2THP | 3-$C_3$OPh | CH2CH2O |
| 16 | iBu | 2-MePh | $CH_2O$ |
| 17 | CH2CH2OCH3 | 4-$CF_3$OPh | $CH_2O$ |
| 18 | CH2CH2CH2OCH3 | 4-$CF_3$OPh | $CH_2O$ |
| 19 | Dimethylacetal | 4-$CF_3$OPh | $CH_2O$ |
| 20 | Me | 4-$CF_3$OPh | $CH_2O$ |
| 21 | CH2CH2OEt | 4-CF3OPh | $CH_2O$ |
| 22 | CH2CH2CH2OEt | 4-CF3OPh | $CH_2O$ |
| 23 | Et | 4-CF3OPh | $CH_2O$ |
| 24 | CH2THP | 4-CF3OPh | $CH_2O$ |
| 25 | 3-methylenepyridine | 4-CF3OPh | $CH_2O$ |
| 26 | 4-Methylenepyridine | 4-CF3OPh | $CH_2O$ |
| 27 | Cyclopropyl | 4-CF3OPh | $CH_2O$ |
| 28 | 2-(Methylthio)ethyl | 4-CF3OPh | $CH_2O$ |
| 29 | 2-methylenepyridine | 4-CF3OPh | $CH_2O$ |
| 30 | CH2CH2SMe | 4-CF3OPh | $CH_2O$ |
| 31 | i-Pr | 4-CF3OPh | $CH_2O$ |
| 32 | CH2furan | 4-CF3OPh | $CH_2O$ |
| 33 | Cyclopropanemethyl | 4-CF3OPh | $CH_2O$ |
| 34 | n-Pr | 4-CF3OPh | $CH_2O$ |
| 35 | Cyclobutyl | 4-CF3OPh | $CH_2O$ |
| 36 | 3-dimethylamino-2,2-dimethyl-propyl | 4-CF3OPh | $CH_2O$ |
| 37 | 3-dimethylamino-2,2-dimethyl-propyl | 4-CF3OPh | $CH_2O$ |
| 38 | 2-methylallyl | 4-CF3OPh | $CH_2O$ |
| 39 | 2-fluoropyridine | 4-CF3OPh | $CH_2O$ |
| 40 | n-Bu | 4-CF3OPh | $CH_2O$ |
| 41 | 2-Methylbutyl | 4-CF3OPh | $CH_2O$ |
| 42 | 2-trifluoromethylbenzyl | 4-CF3OPh | $CH_2O$ |
| 43 | 4-phenyl-1-butyl | 4-CF3OPh | $CH_2O$ |
| 44 | Dimethlyacetal | 3-CF3OPh | $CH_2O$ |
| 45 | proprionitrile | 3-CF3OPh | $CH_2O$ |
| 46 | Et | 3-CF3OPh | $CH_2O$ |
| 47 | CH2THP | 3-CF3OPh | $CH_2O$ |
| 48 | CH2THP | 3-CF3OPh | $CH_2O$ |
| 49 | 2-(Methylthio)ethyl | 3-CF3OPh | $CH_2O$ |
| 50 | i-Pr | 3-CF3OPh | $CH_2O$ |
| 51 | 4-Ethylenepyridine | 3-CF3OPh | $CH_2O$ |
| 52 | Cyclopropanemethyl | 3-CF3OPh | $CH_2O$ |
| 53 | 2-methylallyl | 3-CF3OPh | $CH_2O$ |
| 54 | i-Bu | 3-CF3OPh | $CH_2O$ |
| 55 | n-Bu | 3-CF3OPh | $CH_2O$ |
| 56 | 2-Methylbutyl | 3-CF3OPh | $CH_2O$ |
| 57 | 2-Methylbutyl | 3-CF3OPh | $CH_2O$ |
| 58 | proprionitrile | 3-MePh | CH2O |
| 59 | 2-(Methylthio)ethyl | 3-MePh | CH2O |
| 60 | Methylfuran | 3-MePh | CH2O |
| 61 | Cyclopropanemethyl | 3-MePh | CH2O |
| 62 | 2-methylallyl | 3-MePh | CH2O |
| 63 | i-Bu | 3-MePh | CH2O |
| 64 | 2(methylthio)phenyl | 3-MePh | CH2O |
| 65 | Dimethlyacetal | 3-EtPh | CH2O |
| 66 | 2-ethoxyethyl | 3-EtPh | CH2O |
| 67 | CH2THP | 3-EtPh | CH2O |
| 68 | CH2THP | 3-EtPh | CH2O |
| 69 | 3-methylenepyridine | 3-EtPh | CH2O |

TABLE 1-continued

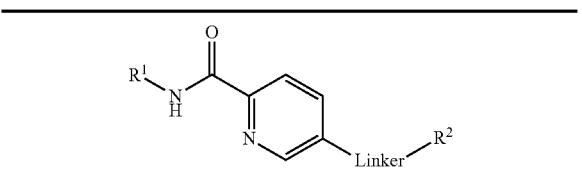

| Compound No. | R¹ | R² | Linker |
|---|---|---|---|
| 70 | 2-(Methylthio)ethyl | 3-EtPh | CH2O |
| 71 | 2-(Methylthio)propyl | 3-EtPh | CH2O |
| 72 | Methylfuran | 3-EtPh | CH2O |
| 73 | Cyclopropanemethyl | 3-EtPh | CH2O |
| 74 | n-Pr | 3-EtPh | CH2O |
| 75 | Cyclobutyl | 3-EtPh | CH2O |
| 76 | 2-Methylallyl | 3-EtPh | CH2O |
| 77 | i-Bu | 3-EtPh | CH2O |
| 78 | 2-Methylbutyl | 3-EtPh | CH2O |
| 79 | 2-Methylbutyl | 3-CF3OPh | CH2O |
| 80 | N,N,2,2-Tetramethyl-1,3-propane | 2-CF3Ph | CH2O |
| 81 | CH2CH2OCH3 | 4-CF3Ph | CH2O |
| 82 | proprionitrile | 4-CF3Ph | CH2O |
| 83 | Me | 4-CF3Ph | CH2O |
| 84 | 2-ethoxyethyl | 4-CF3Ph | CH2O |
| 85 | 2-Methoxyisopropyl | 4-CF3Ph | CH2O |
| 86 | 3-Ethoxypropyl | 4-CF3Ph | CH2O |
| 87 | Et | 4-CF3Ph | CH2O |
| 88 | CH2THP | 4-CF3Ph | CH2O |
| 89 | 4-CH2pyridyl | 4-CF3Ph | CH2O |
| 90 | Cyclopropyl | 4-CF3Ph | CH2O |
| 91 | 2-(Methylthio)ethyl | 4-CF3Ph | CH2O |
| 92 | 3-Isopropoxypropyl | 4-CF3Ph | CH2O |
| 93 | 2-(Methylthio)propyl | 4-CF3Ph | CH2O |
| 94 | i-Pr | 4-CF3Ph | CH2O |
| 95 | Cyclopropanemethyl | 4-CF3Ph | CH2O |
| 96 | CH2CF3 | 4-CF3Ph | CH2O |
| 97 | 2-methylallyl | 4-CF3Ph | CH2O |
| 98 | 2-fluoropyridine | 4-CF3Ph | CH2O |
| 99 | iBu | 4-CF3Ph | CH2O |
| 100 | Propargyl | 4-CF3Ph | CH2O |
| 101 | n-Bu | 4-CF3Ph | CH2O |
| 102 | i-Am | 4-CF3Ph | CH2O |
| 103 | 4-Fluorophenyl | 4-CF3Ph | CH2O |
| 104 | n-Bu | 2-OCF3Ph | CH2O |
| 105 | CH2CH2OCH3 | 3-Br-5-FPh | CH2O |
| 106 | 3-Methoxypropyl | 3-Br-5-FPh | CH2O |
| 107 | Dimethlyacetal | 3-Br-5-FPh | CH2O |
| 108 | Propionitrile | 3-Br-5-FPh | CH2O |
| 109 | 2-Methoxyisopropyl | 3-Br-5-FPh | CH2O |
| 110 | 3-Ethoxypropyl | 3-Br-5-FPh | CH2O |
| 111 | Et | 3-Br-5-FPh | CH2O |
| 112 | CH2THP | 3-Br-5-FPh | CH2O |
| 113 | 3-Methylenepyridine | 3-Br-5-FPh | CH2O |
| 114 | 4-Methylenepyridine | 3-Br-5-FPh | CH2O |
| 115 | 2-(Methylthio)ethyl | 3-Br-5-FPh | CH2O |
| 116 | 3-Isopropoxypropyl | 3-Br-5-FPh | CH2O |
| 117 | 2-(Methylthio)propyl | 3-Br-5-FPh | CH2O |
| 118 | 4-CH2CH2pyridyl | 3-Br-5-FPh | CH2O |
| 119 | Cyclopropanemethyl | 3-Br-5-FPh | CH2O |
| 120 | n-Pr | 3-Br-5-FPh | CH2O |
| 121 | 2-CH2CH2pyridyl | 3-Br-5-FPh | CH2O |
| 122 | Cyclobutyl | 3-Br-5-FPh | CH2O |
| 123 | CH2CF3 | 3-Br-5-FPh | CH2O |
| 124 | 3-dimethylamino-2,2-dimethyl-propyl | 3-Br-5-FPh | CH2O |
| 125 | i-Bu | 3-Br-5-FPh | CH2O |
| 126 | Propargyl | 3-Br-5-FPh | CH2O |
| 127 | n-Bu | 3-Br-5-FPh | CH2O |
| 128 | neo-pentyl | 3-Br-5-FPh | CH2O |
| 129 | i-Am | 3-Br-5-FPh | CH2O |
| 130 | 2-Methylbutyl | 3-Br-5-FPh | CH2O |
| 131 | 4-CF3O-phenyl | 3-Br-5-FPh | CH2O |
| 132 | i-Bu | 3-CF3OBn | CH2O |
| 133 | i-Bu | 4-CF3OBn | CH2O |
| 134 | i-Bu | 4-CF3Bn | CH2O |
| 135 | i-Bu | 3-CF3Bn | CH2O |
| 136 | i-Bu | 4-CF3OPh | OCH2 |
| 137 | CH2THP | 3-CF3OBn | CH2O |
| 138 | CH2THP | 4-CF3OBn | CH2O |
| 139 | CH2THP | 3-CF3Bn | CH2O |
| 140 | CH2THP | 4-CF3Bn | CH2O |
| 141 | Cyclopropanemethyl | 3-CF3Ph | OCH2CH2 |
| 142 | Cyclopropanemethyl | 4-CF3OPh | OCH2CH2 |
| 143 | i-Bu | 4-CF3OPh | OCH2CH2 |
| 144 | i-Bu | 3-CF3Ph | OCH2 |
| 145 | Cyclopropanemethyl | 3-CF3Ph | OCH2 |
| 146 | 2-Methylallyl | 3-CF3OPh | CH2O |
| 147 | 4-CF3O-phenyl | 3-CF3OPh | CH2O |
| 148 | 4-((CF3)2FCPhenyl | 3-CF3OPh | CH2O |
| 149 | Cyclopropanemethyl | 3-OCH3Ph | CH2O |
| 150 | 2-Methylallyl | 3-OCH3Ph | CH2O |
| 151 | i-Bu | 3-OCH3Ph | CH2O |
| 152 | 2-Methylbutyl | 3-CH3OPh | CH2O |
| 153 | CH2THP | 3,4-FPh | CH2O |
| 154 | 2-(Methylthio)ethyl | 3,4-FPh | CH2O |
| 155 | i-Bu | 3,4FPh | CH2O |
| 156 | 3-CF3-Benzyl | 3,4-FPh | CH2O |
| 157 | Acetaldehyde dimethyl acetal | 3-PrPh | CH2O |
| 158 | CH2THP | 3-PrPh | CH2O |
| 159 | CH2-4-pyridyl | 3-PrPh | CH2O |
| 160 | 2-(Methylthio)ethyl | 3-PrPh | CH2O |
| 161 | (CH2)2-4-pyridyl | 3-PrPh | CH2O |
| 162 | N,N,2,2-Tetramethyl-1,3-propane | 3-PrPh | CH2O |
| 163 | 2-Methylallyl | 3-PrPh | CH2O |
| 164 | 3-(1H-imidazol-1-yl)-1-propane | 3-(3-FPh)Ph | CH2O |
| 165 | CH2CH2OCH3 | 3-(3-FPh)Ph | CH2O |
| 166 | 3-methoxypropyl | 3-(3-FPh)Ph | CH2O |
| 167 | Dimethlyacetal | 3-(3-FPh)Ph | CH2O |
| 168 | Proprionitrile | 3-(3-FPh)Ph | CH2O |
| 169 | Me | 3-(3-FPh)Ph | CH2O |
| 170 | Et | 3-(3-FPh)Ph | CH2O |
| 171 | CH2THP | 3-(3-FPh)Ph | CH2O |
| 172 | 3-methylenepyridine | 3-(3-FPh)Ph | CH2O |
| 173 | CH2-4-pyridyl | 3-(3-FPh)Ph | CH2O |
| 174 | 2-(Methylthio)ethyl | 3-(3-FPh)Ph | CH2O |
| 175 | (CH2)2-4-pyridyl | 3-(3-FPh)Ph | CH2O |
| 176 | Cyclopropanemethyl | 3-(3-FPh)Ph | CH2O |
| 177 | n-Pr | 3-(3-FPh)Ph | CH2O |
| 178 | N,N,2,2-Tetramethyl-1,3-propane | 3-(3-FPh)Ph | CH2O |
| 179 | 2-Methylallyl | 3-(3-FPh)Ph | CH2O |
| 180 | i-Bu | 3-(3-FPh)Ph | CH2O |
| 181 | 2-Methylbutyl | 3-(3-FPh)Ph | CH2O |
| 182 | 2-CF3Phenyl | 3-(3-FPh)Ph | CH2O |
| 183 | CH2CH2OCH3 | 3-(Ph)Ph | CH2O |
| 184 | CH2CH2CH2OCH3 | 3-(Ph)Ph | CH2O |
| 185 | Dimethlyacetal | 3-(Ph)Ph | CH2O |
| 186 | Proprionitrile | 3-(Ph)Ph | CH2O |
| 187 | Me | 3-(Ph)Ph | CH2O |
| 188 | Et | 3-(Ph)Ph | CH2O |
| 189 | CH2THP | 3-(Ph)Ph | CH2O |
| 190 | 3-methylenepyridine | 3-(Ph)Ph | CH2O |
| 191 | CH2-4-pyridyl | 3-(Ph)Ph | CH2O |
| 192 | 2-(Methylthio)ethyl | 3-(Ph)Ph | CH2O |
| 193 | (CH2)2-4-pyridyl | 3-(Ph)Ph | CH2O |
| 194 | Cyclopropanemethyl | 3-(Ph)Ph | CH2O |
| 195 | 2-CH2CH2pyridyl | 3-(Ph)Ph | CH2O |
| 196 | N,N,2,2-Tetramethyl-1,3-propane | 3-(Ph)Ph | CH2O |
| 197 | 2-Methylallyl | 3-(Ph)Ph | CH2O |
| 198 | i-Bu | 3-(Ph)Ph | CH2O |
| 199 | i-Bu | 3-EtOPh | CH2O |
| 200 | 4-CF3O-phenyl | 3-EtOPh | CH2O |

TABLE 1-continued

![Structure: R¹-NH-C(=O)-pyridine-Linker-R²]

| Compound No. | R¹ | R² | Linker |
|---|---|---|---|
| 201 | 4-SMe-phenyl | 3,3-Dimethylbutane | CH2O |
| 202 | 4-CF3-phenyl | 3,3-Dimethylbutane | CH2O |
| 203 | Proprionitrile | Indane | CH2O |
| 204 | Cyclopropanemethyl | Indane | CH2O |
| 205 | CH2THP | 3-CF3Ph-CH2CH2 | O |
| 206 | i-Bu | 4-CF3Ph | CH2CH2O |
| 207 | Cyclopropanemethyl | 4-CF3Ph | CH2CH2O |
| 208 | Cyclopropanemethyl | 3-CF3Ph | CH2CH2O |
| 209 | i-Bu | 3-CF3Ph | CH2CH2O |
| 210 | Neopentyl | 2-F-4-CF3Bn | CH2O |
| 211 | Neopentyl | 4-Cl-5-CF3OBn | CH2O |
| 212 | Neopentyl | 4-F-5-OCF3Bn | CH2O |
| 213 | Neopentyl | 3-F-5-CF3Bn | CH2O |
| 214 | Neopentyl | 2-MeO-4-CF3OBn | CH2O |
| 215 | Neopentyl | 3-ClBn | CH2O |
| 216 | Neopentyl | 4-ClBn | CH2O |
| 217 | Neopentyl | 3-MeBn | CH2O |
| 218 | CH2THP | 4-CF3Ph | CH2CH2O |
| 219 | 2-Methylbutyl | 4-CF3Ph | CH2CH2O |
| 220 | CH2THP | 3-CF3Ph | CH2CH2O |
| 221 | 2-Methylbutyl | 3-CF3Ph | CH2CH2O |
| 222 | i-Bu | 3-OCF3-4F-Ph | CH2CH2O |
| 223 | i-Bu | 3-CF3O-4-ClPH | CH2CH2O |
| 224 | i-Bu | 3,4-FPh | CH2CH2O |
| 225 | i-Bu | 3,5-ClPh | CH2CH2O |
| 226 | i-Bu | 3-Br-5-FPh | CH2CH2O |
| 227 | i-Bu | 3-CF3O-4-ClBn | CH2O |
| 228 | i-Bu | 3-CF3O-4-FBn | CH2O |
| 229 | i-Bu | 3-CF3-5-FBn | CH2O |
| 230 | i-Bu | 2-MeO-4-CF3OBn | CH2O |
| 231 | i-Bu | 2-Br-4-CF3Bn | CH2O |
| 232 | i-Bu | 2-F-4-CF3Bn | CH2O |
| 233 | i-Bu | 3-ClBn | CH2O |
| 234 | i-Bu | 4-ClBn | CH2O |
| 235 | i-Bu | 3-MeOBn | CH2O |
| 236 | i-Bu | 3-MeBn | CH2O |
| 237 | i-Bu | 3-CF3O-4-BrPh | CH2CH2O |
| 238 | i-Bu | 3-acetylenePh | CH2CH2O |
| 239 | i-Pr | 3-CF3OPh | CH2CH2O |
| 240 | i-Am | 3-CF3OPh | CH2CH2O |
| 241 | s-Bu | 3-CF3OPh | CH2CH2O |
| 242 | 2-Methylbutyl | 3-CF3OPh | CH2CH2O |
| 243 | Cyclopropanemethyl | 3-CF3OPh | CH2CH2O |
| 244 | CH(Me)THP | 3-CF3OPh | CH2CH2O |
| 245 | 3-dimethylamino-2,2-dimethyl-propyl | 3-CF3OPh | CH2CH2O |
| 246 | (S)-(−)-3,3-dimethyl 2-aminobutane | 3-CF3OPh | CH2CH2O |
| 247 | (S)-(−)-3,3-dimethyl 2-aminobutane | 3-CF3OPh | CH2CH2O |
| 248 | (1R,2R,4S)-2-amino-bicyclo[2.2.1]heptane | 3-CF3OPh | CH2CH2O |
| 249 | i-Bu | 3-Br-5-FPh | C(CH3)2O |
| 250 | CH2THP | 3-Br-5-FPh | C(CH3)2CH2O |
| 251 | i-Bu | 3-CF3OPh | CH(CH3)CH2O |
| 252 | CH2THP | 3-CF3OPh | CH(CH3)CH2O |
| 253 | CH2THP | 3-CF3O-4-ClBn | CH2O |
| 254 | CH2THP | 2-F-5-CF3Bn | CH2O |
| 255 | CH2THP | 2-MeO-4-CF3Bn | CH2O |
| 256 | CH2THP | 2-Br-4-CF3Ph | CH2O |
| 257 | CH2THP | 2-F-4-CF3Ph | CH2O |
| 258 | CH2THP | 3-ClBn | CH2O |
| 259 | CH2THP | 4-ClBn | CH2O |
| 260 | CH2THP | 2-ClBn | CH2O |
| 261 | CH2THP | 3-MeOBn | CH2O |
| 262 | CH2THP | 3-MeBn | CH2O |
| 263 | CH2THP | 4-MeBn | CH2O |
| 264 | CH2THP | 2-MeBn | CH2O |
| 265 | CH2THP | 3-IBn | CH2O |
| 266 | CH2THP | 2-CF3Bn | CH2O |
| 267 | CH2THP | 2-FBn | CH2O |
| 268 | CH2THP | 3-FBn | CH2O |
| 269 | CH2THP | 4-FBn | CH2O |
| 270 | CH2THP | 3,4-FBn | CH2O |
| 271 | i-Bu | 3-Br-5-FPh | CH(CH3)CH2O |
| 272 | CH2THP | 3-Br-5-FPh | C(CH3)2CH2O |
| 273 | i-Bu | 3-CF3Ph | C(CH3)2CH2O |
| 274 | Cyclopropanemethyl | 3-CF3OPh | C(CH3)2CH2O |
| 275 | i-Bu | 3,5-CF3Ph | CH2CH2O |
| 276 | 2-Methylbutyl | 3,5-CF3Ph | CH2CH2O |
| 277 | CH2THP | 3,5-CF3Ph | CH2CH2O |
| 278 | i-Bu | 3-F-5-CF3Ph | CH2CH2O |
| 279 | 2-Methylbutyl | 3-F-5-CF3Ph | CH2CH2O |
| 280 | N,N-dimethylethylenediamine | 3-CF3OPh | CH2CH2O |
| 281 | i-Bu | 3-CF3-4-FPh | CH2CH2O |
| 282 | 3-dimethylamino-2,2-dimethyl-propyl | 3-CF3-4-FPh | CH2CH2O |
| 283 | i-Bu | 3F-4-CF3Bn | CH2O |
| 284 | i-Bu | 3Cl-4-CF3Bn | CH2O |
| 285 | i-Bu | 2-BrBn | CH2O |
| 286 | i-Bu | 3-BrBn | CH2O |
| 287 | i-Bu | 3,5-BrBn | CH2O |
| 288 | i-Bu | 3-Br-5-FBn | CH2O |
| 289 | i-Bu | 3-Br-4-FBn | CH2O |
| 290 | i-Bu | 2,3-FBn | CH2O |

B. Biological Assays

Example 42

Screening Method to Test Contact Activity of Compounds Against Ticks

A solution of the test compound was used to coat the inner wall of glass vials and to treat two filter papers. Once dried, one filter paper was placed in the cap of the vial and the other in the bottom of the vial. Each treated vial was infested with 10 adult *Rhipicephalus sanguineus* (Brown Dog Tick). Contact of the ticks with residues was induced by holding the vials in a controlled environment (24° C., 90-95% relative humidity) and assessment was performed at 24, 48 hours after application in comparison with untreated controls.

Example 43

Screening Method to Test Activity of Compounds Against Fleas Following Ingestion A cylindrical test container was filled with 10 adult *Ctenocephalides felis*. A cylindrical well was closed on one end with a self-sealing flexible film and placed on top of the test container in such a position that the fleas could pierce the film and feed on the contents of the cylinder. The test compound solution was then pipetted into bovine blood and added to the well. The container part with the *Ctenocephalides felis* was held at 20-22° C. and 40-60% relative humidity while the well part containing the treated blood was held at 37° C. and 40-60% relative humidity. Assessment was performed at 72 hours after application in comparison with untreated controls.

Example 44

Screening Method to Test Contact Activity of Compounds Against Flies

A solution of the test compound was used to treat a filter paper contained within a Petri dish and the filter paper was allowed to evaporate to dryness. A small piece of absorbent cotton moistened with 10% sucrose and ten adult flies (*Haematobia irritans* or *Stomoxys calcitrans*) were added to each dish. Dishes were capped and held at room temperature. Assessments were performed at 4 and 24 hours after infestation in comparison with untreated controls.

Example 45

Screening Method to Test Activity of Compounds Against Mosquito

Ten neonate *Aedes aegypti* larvae were added to wells of a microtitre plate containing a nutrient medium and the test compound in DMSO. The microtitre plate was then held at 22° C. where the L1 larvae were allowed to develop. An analysis was conducted at 2 days to determine the inhibition of motility of the treated larvae relative to control larvae.

Example 46

Screening Method to Test Activity of Compounds Against *H. Contortus*

Twenty L1 *Haemonchus contortus* larvae were added to wells of a microtitre plate containing a nutrient medium and the test compound in DMSO. The microtitre plate was then held at 27° C. where the L1 larvae were allowed to develop. An analysis was conducted at 3 days to determine successful development to the L3 stage. Larvae exposed to DMSO and no test compound served as controls

Example 47

Screening Method to Test Activity of Compounds Against *D. Immitis* Microfilaria Four hundred to six hundred microfilaria of *Dirofilaria immitis* were added to wells of a microtitre plate containing RPMI media and the test compound in DMSO. The microtitre plate was then held at 37° C. in an environment containing 5% $CO_2$. An assessment was conducted at 5 days to determine survival of the microfilaria. Microfilaria exposed to DMSO and no test compound served as controls.

Mosquito

| Compound No. | Assay: AHHTSC5 Organism: *A. aegypti* Test Param: $EC_{50}$ Timepoint: 2 day |
|---|---|
| 243 | 0.098 |
| 229 | 0.297 |
| 221 | 0.467 |
| 168 | 0.5125 |
| 155 | 0.6 |
| 178 | 0.6335 |

-continued

| Compound No. | Assay: AHHTSC5 Organism: *A. aegypti* Test Param: $EC_{50}$ Timepoint: 2 day |
|---|---|
| 108 | 0.6 |
| 227 | 0.696 |
| 135 | 0.7 |
| 240 | 0.716 |
| 232 | 0.721 |
| 228 | 0.746 |
| 151 | 0.8 |
| 173 | 0.8615 |
| 222 | 0.939 |
| 225 | 0.981 |
| 120 | 0.9985 |
| 223 | 1.068 |
| 28 | 1.1 |
| 186 | 1.214 |
| 209 | 1.25 |
| 38 | 1.263 |
| 206 | 1.274 |
| 219 | 1.319 |
| 220 | 1.358 |
| 278 | 1.36 |
| 119 | 1.4595 |
| 134 | 1.5 |
| 191 | 1.4955 |
| 35 | 1.5 |
| 236 | 1.58 |
| 114 | 1.6 |
| 284 | 1.6645 |
| 175 | 1.7035 |
| 181 | 1.709 |
| 20 | 1.769 |
| 281 | 1.7855 |
| 179 | 1.792 |
| 190 | 1.794 |
| 193 | 1.868 |
| 122 | 2.0 |
| 196 | 2.012 |
| 30 | 2.02 |
| 12 | 2.1 |
| 49 | 2.2 |
| 98 | 2.156 |
| 183 | 2.2465 |
| 283 | 2.265 |
| 24 | 2.3 |
| 275 | 2.299 |
| 194 | 2.3015 |
| 10 | 2.3 |
| 185 | 2.326 |
| 165 | 2.3355 |
| 208 | 2.3375 |
| 166 | 2.4 |
| 18 | 2.3975 |
| 26 | 2.404 |
| 126 | 2.408 |
| 172 | 2.447 |
| 216 | 2.463 |
| 76 | 2.5 |
| 112 | 2.5375 |
| 63 | 2.5 |
| 2 | 2.545 |
| 189 | 2.5955 |
| 197 | 2.626 |
| 177 | 2.66 |
| 256 | 2.727 |
| 117 | 2.741 |
| 238 | 2.872 |
| 91 | 2.9335 |
| 34 | 2.9595 |
| 40 | 3.077 |
| 53 | 3.179 |
| 230 | 3.181 |
| 23 | 3.2 |
| 97 | 3.2915 |
| 237 | 3.313 |
| 198 | 3.335 |

77
-continued

| Compound No. | Assay: AHHTSC5<br>Organism: *A. aegypti*<br>Test Param: $EC_{50}$<br>Timepoint: 2 day |
|---|---|
| 283 | 3.387 |
| 121 | 3.3925 |
| 242 | 3.42 |
| 5 | 3.5 |
| 167 | 3.5 |
| 192 | 3.476 |
| 21 | 3.492 |
| 234 | 3.642 |
| 169 | 3.648 |
| 253 | 3.834 |
| 231 | 3.834 |
| 187 | 3.862 |
| 277 | 3.867 |
| 150 | 3.9 |
| 9 | 3.9 |
| 171 | 4.0 |
| 205 | 4.171 |
| 124 | 4.3 |
| 44 | 4.3 |
| 188 | 4.3275 |
| 118 | 4.336 |
| 163 | 4.508 |
| 127 | 4.5 |
| 272 | 4.5555 |
| 270 | 4.636 |
| 4 | 5.0 |
| 77 | 5.0 |
| 93 | 5.002 |
| 176 | 5.1 |
| 148 | 5.3165 |
| 184 | 5.5175 |
| 120 | 5.6 |
| 207 | 6 |
| 70 | 6.0 |
| 83 | 6.041 |
| 170 | 6.1015 |
| 95 | 6.126 |
| 199 | 6.17 |
| 143 | 6.1985 |
| 17 | 6.218 |
| 113 | 6.2905 |
| 102 | 6.293 |
| 41 | 6.4 |
| 123 | 6.5315 |
| 147 | 6.5405 |
| 101 | 6.5955 |
| 103 | 6.6565 |
| 160 | 6.7815 |
| 218 | 6.817 |
| 65 | 7.0 |
| 174 | 7.1 |
| 19 | 7.3045 |
| 128 | 7.342 |
| 89 | 7.3435 |
| 7 | 7.448 |
| 87 | 7.453 |
| 92 | 7.4715 |

78
-continued

| Compound No. | Assay: AHHTSC5<br>Organism: *A. aegypti*<br>Test Param: $EC_{50}$<br>Timepoint: 2 day |
|---|---|
| 51 | 7.477 |
| 3 | 7.535 |
| 99 | 7.57 |
| 100 | 7.5845 |
| 195 | 7.5885 |
| 274 | 7.6085 |
| 42 | 7.624 |
| 140 | 7.7 |
| 154 | 7.704 |
| 144 | 7.754 |
| 290 | 7.808 |
| 61 | 7.834 |
| 23 | 7.899 |
| 136 | 7.94 |
| 146 | 7.9575 |
| 13 | 8.0 |
| 90 | 8.06 |
| 251 | 8.13 |
| 273 | 8.1315 |
| 203 | 8.177 |
| 131 | 8.192 |
| 224 | 8.224 |
| 250 | 8.6205 |
| 25 | 8.634 |
| 22 | 8.6405 |
| 15 | 8.8 |
| 52 | 8.784 |
| 59 | 8.7905 |
| 141 | 8.7915 |
| 285 | 8.88 |
| 116 | 8.992 |
| 252 | 9.08825 |
| 164 | 9.28 |
| 288 | 9.2895 |
| 233 | 9.353 |
| 162 | 9.397 |
| 149 | 9.4 |
| 86 | 9.434 |
| 35 | 9.4345 |
| 64 | 9.493 |
| 182 | 9.509 |
| 1 | 9.539 |
| 157 | 9.5735 |
| 259 | 9.668 |
| 105 | 9.6945 |
| 282 | 9.705 |
| 239 | 9.709 |
| 286 | 9.774 |
| 50 | 9.808 |
| 145 | 9.863 |
| 204 | 9.911 |
| 39 | 9.9195 |
| 159 | 9.948 |
| 265 | 9.9755 |
| 210 | 9.987 |

| | Tick Contact $EC_{50}$ DMSO<br>*Rhipicephalus sanguineus*<br>Paramater: $EC_{50}$<br>Timepoint: (below in hrs.) | | | Fly Contact $EC_{50}$<br>Paramater: $EC_{50}$<br>Timepoint:<br>(below in hrs.) | | Stable<br>Fly | Tick Contact $EC_{50}$<br>DMSO<br>*Rhipicephalus sanguineus*<br>Paramater: $EC_{50}$<br>Timepoint:<br>(below in hrs.) | |
|---|---|---|---|---|---|---|---|---|
| | | | | Horn Fly | | | | |
| Cmpd No. | 4 hr | 24 hr | 48 hr | 4 hr | 24 hr | 24 hr | 24 hr | 48 hr |
| 4 | | >200.0 | 197.8 | >5 | >5 | | | |
| 5 | | 52.4 | 46.3 | >5 | ~2.8 | ~1.4 | | |
| 9 | | 200.0 | 181.7 | | | | | |

-continued

| Cmpd No. | Tick Contact EC$_{50}$ DMSO *Rhipicephalus sanguineus* Paramater: EC$_{50}$ Timepoint: (below in hrs.) | | | Fly Contact EC$_{50}$ Paramater: EC$_{50}$ Timepoint: (below in hrs.) | | | Tick Contact EC$_{50}$ DMSO *Rhipicephalus sanguineus* Paramater: EC$_{50}$ Timepoint: (below in hrs.) | |
|---|---|---|---|---|---|---|---|---|
| | | | | Horn Fly | | Stable Fly | | |
| | 4 hr | 24 hr | 48 hr | 4 hr | 24 hr | 24 hr | 24 hr | 48 hr |
| 10 | | ~50.0 | ~20.9 | 1.25 | 1.25 | >5.0 | 190.5 | 46.9 |
| 12 | | 31.5 | 15.8 | 1.1 | 1.2 | ~4.6 | 117.0 | 92.2 |
| 13 | | >200.0 | 79.1 | 1.2 | 1.2 | | | |
| 14 | | >200.0 | 92.2 | 1.4 | 1.4 | | | |
| 15 | 126.0 | 14.7 | 12.5 | | | | >200 | 92.6 |
| 24 | | 63.4 | ~46.3 | 0.5 | 1.4 | | >200 | ~169.1 |
| 28 | | >200.0 | ~195.4 | | | | | |
| 33 | | ~50.0 | 36.8 | 0.5 | 0.73 | 1.8 | 72.8 | ~52.4 |
| 37 | | ~200.0 | 100.0 | | | | | |
| 41 | | 117.0 | ~100.0 | 4.8 | 2.5 | | | |
| 44 | | 51.8 | 39.3 | 4.8 | 2.9 | | | |
| 47 | | 197.8 | 177.4 | | | | | |
| 49 | | ~184.9 | 117.0 | 4.6 | 4.6 | | | |
| 54 | | ~188.2 | 51.8 | 2.1 | 0.93 | | | |
| 57 | | >200.0 | ~171.5 | >5 | 2.93 | | | |
| 63 | | 72.8 | 72.8 | 4.6 | 4.6 | 1.3 | | |
| 65 | | ~47.0 | ~42.9 | | | 1.4 | | |
| 67 | | ~190.5 | ~54.0 | | | | | |
| 70 | | ~55.0 | ~55.0 | | | | | |
| 73 | | ~188.2 | ~90.4 | 1.4 | 1.31 | | | |
| 76 | | 79.1 | 62.3 | 2.1 | 1.35 | | | |
| 77 | | ~54.0 | ~50.0 | 1.4 | 1.3 | 1.4 | 100.9 | ~50.5 |
| 78 | | ~193.1 | 108.1 | | | | | |
| 124 | | 126.0 | ~56.2 | 1.4 | 1.4 | | | |
| 125 | | ~13.5 | 12.4 | 0.4 | 0.33 | 0.1 | 38.1 | 36.3 |
| 127 | | ~181.7 | ~53.2 | 1.4 | 1.3 | | | |
| 129 | | ~197.8 | ~51.2 | | | | | |
| 130 | | 72.8 | 50.4 | 4.8 | 1.35 | | | |
| 132 | | 58.2 | 34.3 | ~5 | 1.84 | | 197.8 | 100.0 |
| 133 | | >200.0 | 181.7 | 4.6 | 1.4 | | | |
| 134 | | 40.5 | 25.0 | 2.1 | 2.5 | | >200.0 | 197.8 |
| 135 | | 197.8 | 100.2 | 4.8 | 1.2 | | | |
| 138 | | >200.0 | 193.1 | | | | | |
| 140 | | >200.0 | 190.5 | 1.4 | 2.5 | | | |
| 205 | | >200.0 | 184.9 | 4.8 | 2.9 | | | |
| 206 | | 56.7 | ~14.6 | | | | | |
| 209 | | 44.1 | ~48.9 | | | | | |
| 216 | | >200.0 | ~190.5 | | | | | |
| 219 | | ~184.9 | ~110.6 | | | | | |
| 220 | | ~197.8 | ~195.4 | | | | | |
| 221 | | ~184.9 | 85.5 | | | | | |
| 222 | | 44.1 | ~47.6 | | | | | |
| 225 | | ~100.0 | ~54.0 | | | | | |
| 227 | | ~53.2 | ~48.3 | | | | | |
| 228 | | ~100.0 | ~55.0 | | | | | |
| 229 | | ~188.2 | ~188.2 | | | | | |
| 232 | | ~100.0 | ~51.2 | | | | | |
| 234 | | ~171.5 | ~55.0 | | | | | |

| Cmpd No. | Assay: AHHTSC5 *A. aegypti* Paramater: EC$_{50}$ Timepoint: (below in days) 2 days |
|---|---|
| 4 | 5.0 |
| 5 | 3.5 |
| 9 | 3.9 |
| 10 | 2.3 |
| 12 | 2.1 |
| 13 | 8.0 |
| 14 | >10.0 |
| 15 | 8.8 |
| 24 | 2.3 |
| 28 | 1.1 |
| 33 | 1.5 |
| 37 | |
| 41 | 6.4 |
| 44 | 4.3 |
| 47 | 10.0 |
| 49 | 2.2 |
| 54 | >10.0 |
| 57 | |
| 63 | 2.5 |

| Cmpd No. | Assay: AHHTSC5<br>A. aegypti<br>Paramater: EC$_{50}$<br>Timepoint: (below in days)<br>2 days |
|---|---|
| 65 | 7.0 |
| 67 | |
| 70 | 6.0 |
| 73 | 3.2 |
| 76 | 2.5 |
| 77 | 5.0 |
| 78 | |
| 124 | 10.0 |
| 125 | 0.6 |
| 127 | 1.6 |
| 129 | 5.6 |
| 130 | 2.0 |
| 132 | 4.3 |
| 133 | >10.0 |
| 134 | 4.5 |
| 135 | >10.0 |
| 138 | >10.0 |
| 140 | >10.0 |
| 205 | >10.0 |
| 206 | 1.5 |
| 209 | 0.7 |
| 216 | >10.0 |
| 219 | 7.7 |
| 220 | 9.4 |
| 221 | 3.9 |
| 222 | 0.8 |
| 225 | 0.6 |
| 227 | 2.4 |
| 228 | 3.5 |
| 229 | 4.0 |
| 232 | 7.1 |
| 234 | 5.1 |

| Compound No. | Contact SP<br>Stable Fly<br>PCT Mortality<br>5 µg/cm²<br>Timepoint: (below in hrs) | | Contact EC$_{50}$<br>Stable Fly<br>EC$_{50}$<br>Timepoint: (below in hrs) |
|---|---|---|---|
| | 4 | 24 | 24 |
| 108 | 0% | 0% | 0.1 |
| 119 | 60% | 70% | 0.24 |
| 63 | 80% | 80% | 1.3 |
| 77 | 60% | 80% | 1.4 |
| 65 | 50% | 60% | 1.4 |
| 5 | 70% | 90% | ~1.4 |
| 52 | 60% | 80% | 1.4041 |
| 33 | 80% | 80% | 1.8 |
| 12 | 50% | 90% | ~4.6 |

| Compound No. | LDA SP<br>H. cont.<br>PCT Mot M<br>5 ppm<br>Timepoint:<br>4 days | LDA DR<br>H. cont.<br>MIC 90<br>Timepoint:<br>4 days | Mf sp<br>D. immitis<br>PCT Motili<br>5 ppm<br>Timepoint:<br>5 days | Mf sp<br>D. immitis<br>EC$_{50}$<br>5 ppm<br>Timepoint:<br>5 days |
|---|---|---|---|---|
| 206 | 100% | 1.3 | | |
| 219 | 90% | 2.7 | | |
| 13 | 95% | 3.1 | | |
| 224 | 98% | 3.125 | | |
| 223 | 91% | 5 | | |
| 207 | 100% | 5 | | |
| 136 | 89.2655 | 5 | | |
| 14 | 100% | 5 | 88% | 4.3 |
| 43 | | 5 | | |

| Compound No. | Assay: MiniInge<br>Organism: C. felis<br>Test Parameter: PCT Mortal<br>Dose: 200 ppm<br>Timepoint: 72 hr | Assay: MiniInge<br>Organism: C. felis<br>Test Parameter: EC$_{50}$<br>Timepoint: 72 hr |
|---|---|---|
| 177 | 40% | 115 |
| 107 | 90% | 116 |
| 162 | 80% | 116 |
| 185 | 90% | 185 |
| 198 | 90% | 185 |
| 176 | 70% | 185 |
| 197 | 90% | 185 |
| 179 | 70% | 191 |
| 243 | 80% | 191 |
| 24 | 0% | 195 |

"Horn Fly"

| Compound No. | Contact SP<br>Horn Fly<br>PCT Mortality (%)<br>5 µg/cm²<br>Timepoint: (below in hrs) | | Fly Contact EC$_{50}$<br>Horn Fly<br>EC$_{50}$<br>Timepoint: (below in hrs) | |
|---|---|---|---|---|
| | 4 | 24 | 4 | 24 |
| 108 | 100 | 100 | 0.38 | 0.33 |
| 119 | 80 | 100 | 0.6248 | 0.5027 |
| 208 | 100 | 100 | | 0.7181 |
| 33 | 100 | 100 | 0.53 | 0.73 |
| 181 | | | 4.62 | 0.73 |
| 54 | 100 | 100 | 2.14 | 0.93 |
| 12 | 80 | 100 | 1.1 | 1.2 |
| 13 | 60 | 70 | 1.2 | 1.2 |
| 129 | 40 | 40 | 4.8 | 1.2 |
| 185 | | | 1.84 | 1.22 |
| 207 | 80 | 80 | | 1.2217 |
| 61 | 90 | 90 | 5 | 1.2217 |
| 10 | 90 | 90 | 1.25 | 1.25 |
| 115 | 0 | 60 | 4.7654 | 1.25 |
| 77 | 100 | 100 | 1.4 | 1.3 |
| 114 | | | 1.4 | 1.3 |
| 73 | 100 | 100 | 1.4 | 1.31 |
| 38 | 50 | 80 | 1.3523 | 1.3122 |
| 122 | 0 | 0 | 4.8 | 1.35 |
| 76 | 0 | 0 | 2.14 | 1.35 |
| 95 | 50 | 70 | 5 | 1.3523 |
| 24 | 50 | 70 | 0.53 | 1.4 |
| 107 | 0 | 0 | 1.4 | 1.4 |
| 179 | | | 2.14 | 1.4 |
| 14 | 80 | 100 | 1.4 | 1.4 |
| 125 | 100 | 100 | 4.6 | 1.4 |
| 53 | 20 | 20 | 2.9253 | 1.5892 |
| 124 | 100 | 100 | ~5 | 1.84 |
| 40 | 0 | 40 | 4.7654 | 2.1372 |
| 127 | 70 | 70 | 2.14 | 2.5 |
| 41 | 60 | 60 | 4.8 | 2.5 |
| 132 | 100 | 100 | 1.35 | 2.5 |
| 5 | 100 | 100 | >5 | ~2.8 |
| 52 | 80 | 80 | 2.8805 | 2.8805 |
| 44 | 80 | 80 | 4.8 | 2.9 |
| 133 | 80 | 80 | 4.76 | 2.9 |

| | Contact SP Horn Fly PCT Mortality (%) 5 μg/cm² Timepoint: (below in hrs) | | Fly Contact EC$_{50}$ Horn Fly EC$_{50}$ Timepoint: (below in hrs) | |
|---|---|---|---|---|
| Compound No. | 4 | 24 | 4 | 24 |
| 57 | 70 | 80 | >5 | 2.9253 |
| 18 | 0 | 40 | 2.8805 | 2.9253 |
| 57 | 70 | 80 | >5 | 2.93 |
| 251 | 80 | 100 | ~4.8843 | 4.4449 |
| 50 | 70 | 80 | 4.8843 | 4.4449 |
| 63 | 100 | 100 | 4.6 | 4.6 |
| 49 | 60 | 0 | 4.6 | 4.6 |
| 34 | 60 | 80 | 2.1371 | 4.6252 |
| 121 | 80 | 80 | 5 | 4.8843 |

"Tick"

| | Contact SP *Rhicicep* PCT Mortality (%) 200 ppm Timepoint: (below in hrs) | | Tick Contact EC$_{50}$ DMSO *Rhipicephalus sanguineus* EC$_{50}$ Timepoint: (below in hrs) | | |
|---|---|---|---|---|---|
| Compound No. | 4 | 24 | 4 | 24 | 48 |
| 240 | 90 | 90 | | 48.861 | 11.0217 |
| 228 | 90 | 90 | | 18.3654 | 11.7142 |
| 221 | 90 | 100 | | 19.9406 | 12.1746 |
| 108 | 70 | 70 | | ~13.5 | 12.4 |
| 15 | | | 126.0 | 14.7 | 12.5 |
| 229 | 80 | 80 | | 19.4837 | 12.5929 |
| 134 | | | | 56.7 | ~14.6 |
| 12 | | | | 31.5 | 15.8 |
| 222 | 90 | 100 | | 27.1261 | 19.4753 |
| 10 | 0 | 100 | | ~50.0 | ~20.9 |
| 206 | 100 | 100 | | 47.6205 | 21.4036 |
| 225 | 90 | 100 | | 27.1261 | 22.6041 |
| 127 | 90 | 100 | | 40.5 | 25.0 |
| 177 | 80 | 90 | | 45.4585 | 25 |
| 243 | 100 | 100 | | 58.8325 | 25 |
| 237 | 90 | 100 | | 49.4465 | 27.6499 |
| 220 | 100 | 100 | | 59.5661 | 33.876 |
| 124 | 70 | 70 | | 58.2 | 34.3 |
| 219 | 80 | 90 | | 44.0869 | 36.3885 |
| 33 | 100 | 100 | | ~50.0 | 36.8 |
| 44 | 100 | 100 | | 51.8 | 39.3 |
| 65 | 80 | 100 | | ~47.0 | ~42.9 |
| 260 | 90 | 100 | | 58.1848 | 42.8922 |
| 234 | 90 | 90 | | 46.9949 | 46.2591 |
| 5 | 50 | 80 | | 52.4 | 46.3 |
| 256 | 90 | 100 | | 52.4342 | 46.2591 |
| 24 | 0 | 0 | | 63.4 | ~46.3 |
| 242 | 70 | 90 | | 171.5279 | 46.2591 |
| 151 | 0 | 80 | | 44.1 | ~47.6 |
| 166 | 40 | 80 | | ~53.2 | ~48.3 |
| 135 | | | | 44.1 | ~48.9 |
| 278 | 70 | 100 | | 53.9616 | 49.4465 |
| 77 | 100 | 100 | | ~54.0 | ~50.0 |
| 241 | 50 | 90 | | 181.6667 | 50 |
| 122 | 0 | 80 | | 72.8 | 50.4 |
| 284 | 90 | 100 | | 51.7921 | 50.5463 |
| 259 | 80 | 90 | | 115.6016 | 50.5463 |
| 198 | 100 | 100 | | 54.9508 | 51.186 |
| 174 | 90 | 100 | | ~100.0 | ~51.2 |
| 120 | 60 | 70 | | ~197.8 | ~51.2 |
| 232 | 100 | 100 | | 115.6016 | 51.7921 |
| 216 | 0 | 60 | | 117.013 | 51.7921 |
| 266 | 70 | 90 | | 67.8106 | 51.8142 |
| 54 | 0 | 100 | | ~188.2 | 51.8 |
| 227 | 100 | 100 | | | 52.4342 |
| 114 | 40 | 60 | | ~181.7 | ~53.2 |
| 155 | 60 | 100 | | ~100.0 | ~54.0 |
| 68 | 50 | 90 | | ~190.5 | ~54.0 |
| 68 | 50 | 90 | | 190.5 | 53.9616 |

| | Contact SP *Rhicicep* PCT Mortality (%) 200 ppm Timepoint: (below in hrs) | | Tick Contact EC$_{50}$ DMSO *Rhipicephalus sanguineus* EC$_{50}$ Timepoint: (below in hrs) | | |
|---|---|---|---|---|---|
| Compound No. | 4 | 24 | 4 | 24 | 48 |
| 283 | 100 | 100 | | 54.4434 | 54.4434 |
| 70 | 80 | 100 | | ~55.0 | ~55.0 |
| 167 | 100 | 100 | | ~100.0 | ~55.0 |
| 176 | 90 | 100 | | ~171.5 | ~55.0 |
| 107 | 0 | 70 | | 126.0 | ~56.2 |
| 76 | 80 | 100 | | 79.1 | 62.3 |
| 181 | 70 | 90 | | 92.6304 | 62.2528 |
| 179 | 100 | 100 | | 83.5861 | 63.3747 |
| 63 | 100 | 100 | | 72.8 | 72.8 |
| 199 | 100 | 100 | | 193.0702 | 77.9043 |
| 13 | | | | >200.0 | 79.1 |
| 257 | 80 | 90 | | 171.5279 | 83.5861 |
| 209 | 90 | 100 | | | 83.5861 |
| 150 | 70 | 70 | | ~184.9 | 85.5 |
| 223 | 0 | 0 | | 110.5989 | 90.417 |
| 23 | 80 | 90 | | ~188.2 | ~90.4 |
| 14 | | | | >200.0 | 92.2 |
| 290 | 80 | 80 | | 100.2134 | 92.7385 |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of Formula I

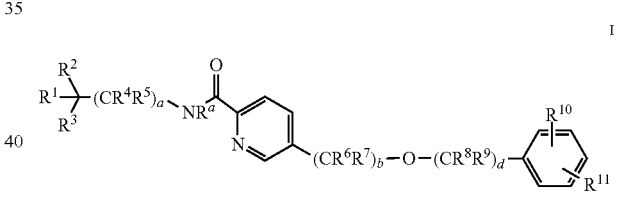

wherein, $R^a$ is selected from the group consisting of hydrogen, alkyl, alkoxyalkyl, alkylcarbonyl, haloalkylcarbonyl, alkoxycarbonyl, haloalkoxycarbonyl, alkylthiocarbonyl, haloalkyl, alkylthio, haloalkylthio, alkoxy, haloalkoxyalkyl, alkoxycarbonyl and haloalkoxycarbonyl;

$R^1$ is hydrogen or alkyl;

$R^2$ and $R^3$ are each independently selected from the group consisting of hydrogen, hydroxy, amino, alkyl, haloalkyl, alkoxyalkyl, alkenyl, alkynyl, alkylthio, alkylamino, dialkylamino, aminoalkyl, alkylaminoalkyl, dialkylaminoalkyl, and cyano, or $R^2$ and $R^3$ taken together with the carbon to which both are bound form a substituted or unsubstituted 3- to 7-member cyclic, heterocyclic or heteroaromatic ring, wherein the substituents may each be independent of one another cyano, nitro, halogen, alkyl, haloalkyl, alkylthio, haloalkylthio, alkoxy, haloalkoxy, amino, alkylamino, and dialkylamino;

a is an integer from zero to four, b is an integer from zero to four, d is an integer from zero to four, $R^4$, $R^5$, $R^6$, $R^7$, $R^8$ and $R^9$ are each independently hydrogen, halogen, alkyl, alkenyl, hydroxyalkyl, alkylthioalkyl, haloalkyl, alkyloxyalkyl, alkylsulfinylalkyl, alkylsulfonylalkyl, alkylsulfonyloxyalkyl, nitro, alkylthio, haloalkylthio, alkoxy, haloalkoxy, amino, alkylamino, and diamino;

$R^{10}$ and $R^{11}$ are each independently selected from the group consisting of hydrogen, hydroxy, amino, cyano, nitro, halogen, thiol, alkylamino, dialkylamino, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, formyl, alkylcarbonyl, alkoxycarbonyl, sulfonyl, sulfinyl, and unsubstituted or substituted phenyl, unsubstituted or substituted benzyl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, alkoxy, haloalkoxy, amino, alkylamino, dialkylamino, alkylaminoalkoxy, dialkylaminoalkoxy, and alkylaminoalkyl, provided that,
at least one of b and d is other than zero, and
at least one of $R^{10}$ and $R^{11}$ is other than hydrogen.

2. The compound of claim 1, wherein
b is one and d is zero,
b is two and d is zero,
b is one and d is one,
b is zero and d is one, or
b is zero and d is two.

3. The compound of claim 2, wherein a is one or two.

4. The compound of claim 1, wherein
a is zero,
provided that when $R^{10}$ and $R^{11}$ are both selected from the group consisting of chloro and methyl, then:
  iii) d is other than zero, or
  iv) $R^a$ is other than $C_{1-6}$ alkyl, or
  iii) $R^2$ and $R^3$ when taken together with the carbon to which both are bound form a ring other than cyclopentyl or cyclohexyl.

5. The compound of claim 1, wherein
$R^{10}$ and $R^{11}$ are each independently selected from the group consisting of hydrogen, halogen, branched or straight-chain $C_{1-6}$ alkyl, $C_{1-6}$ alkenyl, $C_{1-6}$ alkynyl, hydroxy($C_{1-6}$)alkyl, halo($C_{1-6}$)alkyl, $C_{1-6}$ alkoxy, halo($C_{1-6}$)alkoxy and unsubstituted or substituted phenyl, wherein the substituents, independent of one another, may be one or more of halogen, $C_{1-6}$ alkyl, halo($C_{1-6}$)alkyl, $C_{1-6}$ alkoxy, or halo($C_{1-6}$)alkoxy.

6. The compound of claim 5, wherein
$R^{10}$ and $R^{11}$ are each independently selected from the group consisting of hydrogen, bromo, chloro, fluoro, methyl, ethyl, trifluoromethyl and trifluoromethoxy.

7. The compound of claim 1, wherein
a is one,
$R^4$ and $R^5$ are both hydrogen,
b is zero, one or two, and
d is zero, one or two.

8. The compound of claim 7, wherein
b is one or two,
d is zero, and
$R^6$ and $R^7$ in each instance are both hydrogen.

9. The compound of claim 7, wherein
d is one or two,
b is zero, and
$R^8$ and $R^9$ in each instance are both hydrogen.

10. The compound of claim 7, wherein
b is one or two,
$R^6$ and $R^7$ in each instance are both hydrogen,
d is one or two, and
$R^8$ and $R^9$ in each instance are both hydrogen.

11. The compound of claim 1, wherein
$R^1$ is hydrogen or methyl,
$R^2$ and $R^3$ are each independently selected from the group consisting of hydrogen, $C_{1-6}$ alkenyl, cyano, $C_{1-6}$ alkyl, $C_{1-6}$ alkoxy, amino, $C_{1-6}$ alkylamino, di($C_{1-6}$ alkyl) amino and $C_{1-6}$ alkylthio,
or $R^2$ and $R^3$ taken together with the carbon to which both are bound form a substituted or unsubstituted 3- to 7-member cyclic, heterocyclic or heteroaromatic ring.

12. The compound of claim 11, wherein
$R^2$ and $R^3$ taken together with the carbon to which both are bound form a substituted or unsubstituted 3- to 7-member cyclic, heterocyclic or pyridine.

13. The compound of claim 12, wherein
$R^2$ and $R^3$ taken together with the carbon to which both are bound form a substituted or unsubstituted pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, 2-pyrrolinyl, 3-pyrrolinyl, 2H-pyranyl, 4H-pyranyl, dioxanyl, 1,3-dioxolanyl, dithianyl, dithiolanyl and dihydrothienyl.

14. The compound of claim 13, wherein
$R^2$ and $R^3$ taken together with the carbon to which both are bound form a substituted or unsubstituted cyclopropyl or 4-morpholinyl.

15. The compound of claim 11, wherein
$R^2$ and $R^3$ are each independently selected from the group consisting of hydrogen, $C_{1-6}$ alkenyl, $C_{1-6}$ alkyl and $C_{1-6}$ alkylthio.

16. The compound of claim 1, wherein $R^a$ is hydrogen.

17. The compound of claim 1, wherein a is one or two.

18. The compound of claim 1, having one of the following structures:

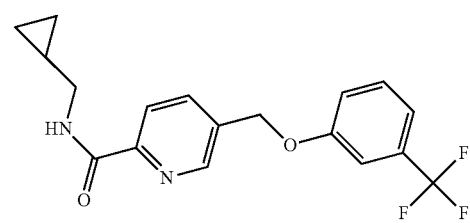

4

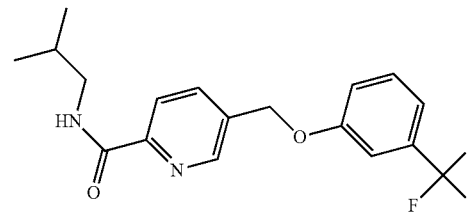

5

9
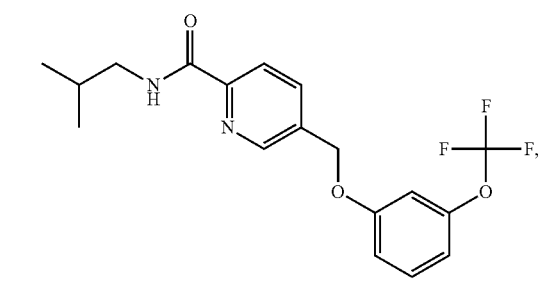
28
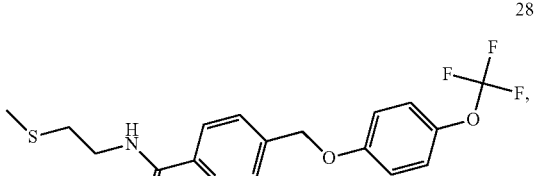
10
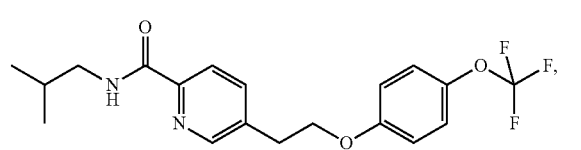
33
12
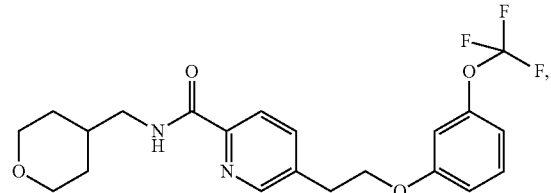
37
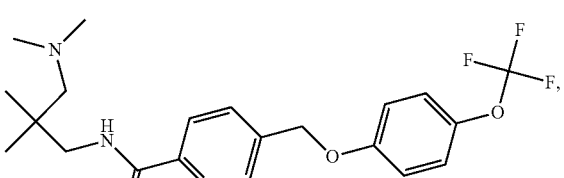
13
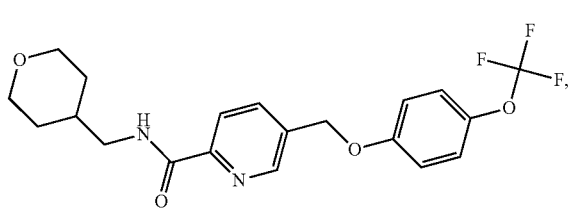
41
14
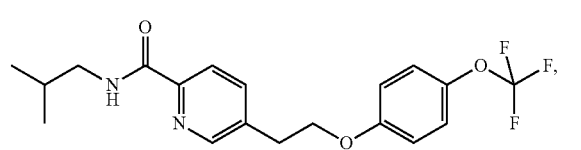
44
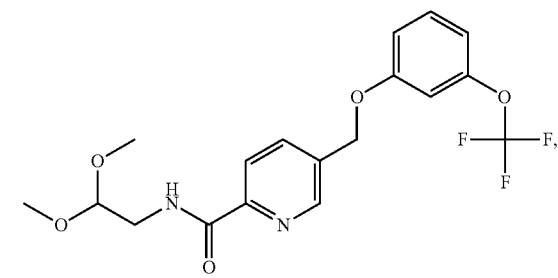
15
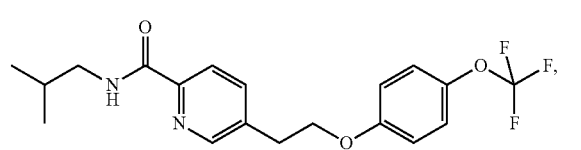
47
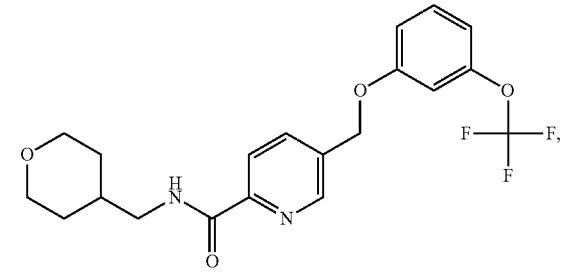
24
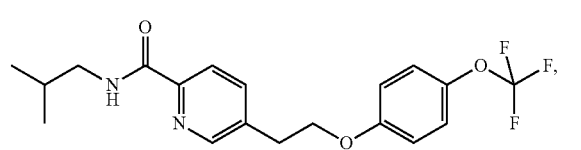

49
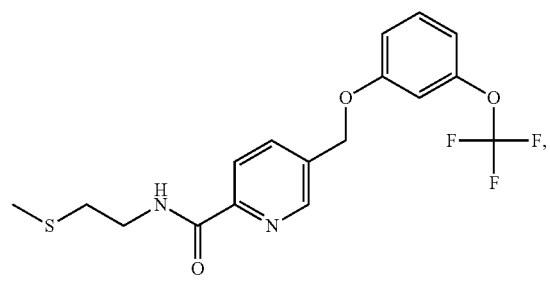
54
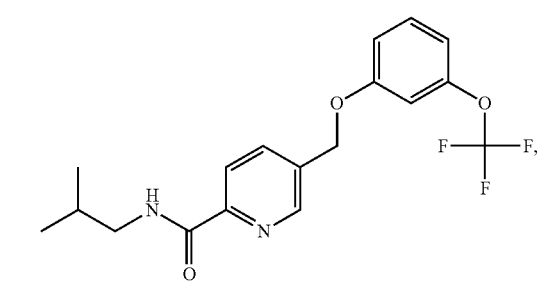
56
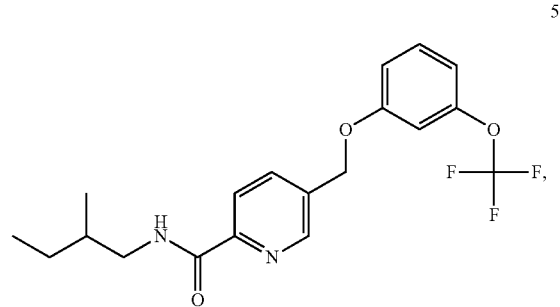
63
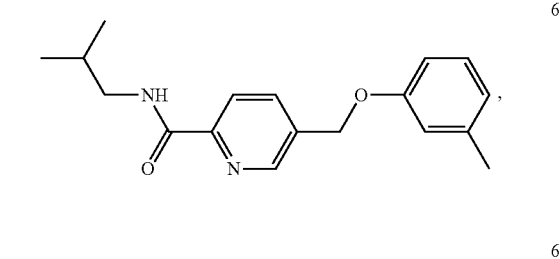
65
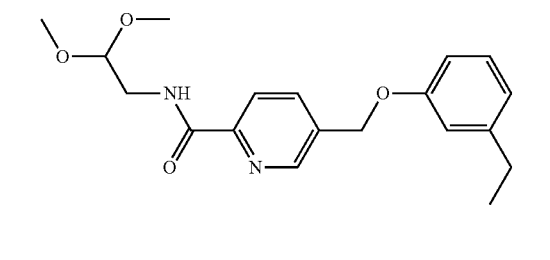
68
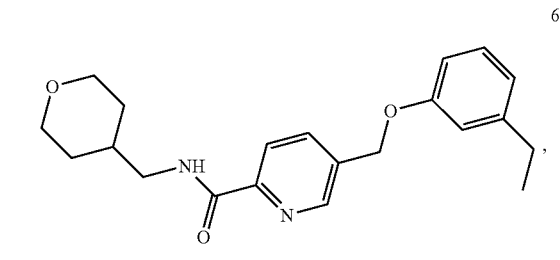
70
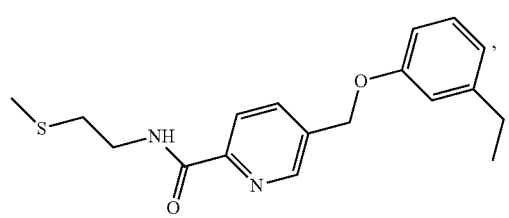
73
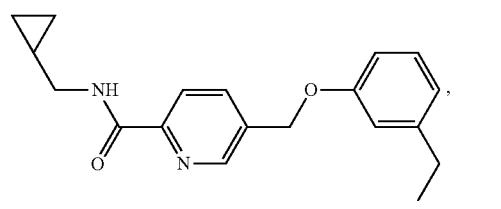
76
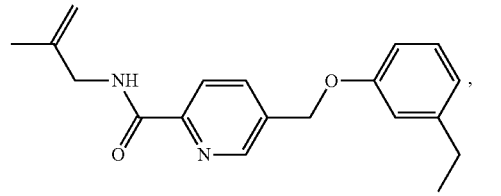
77
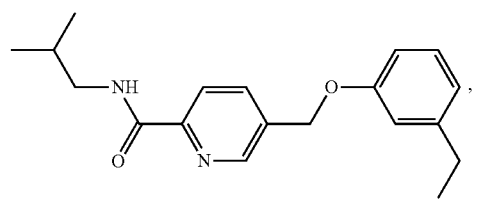
78
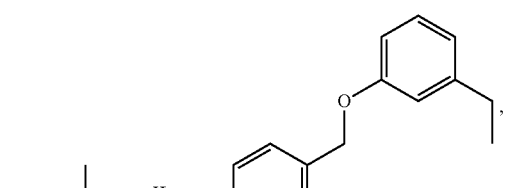
107
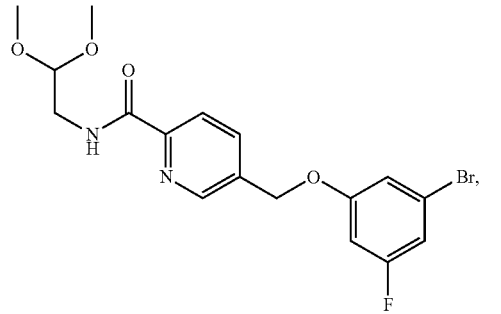

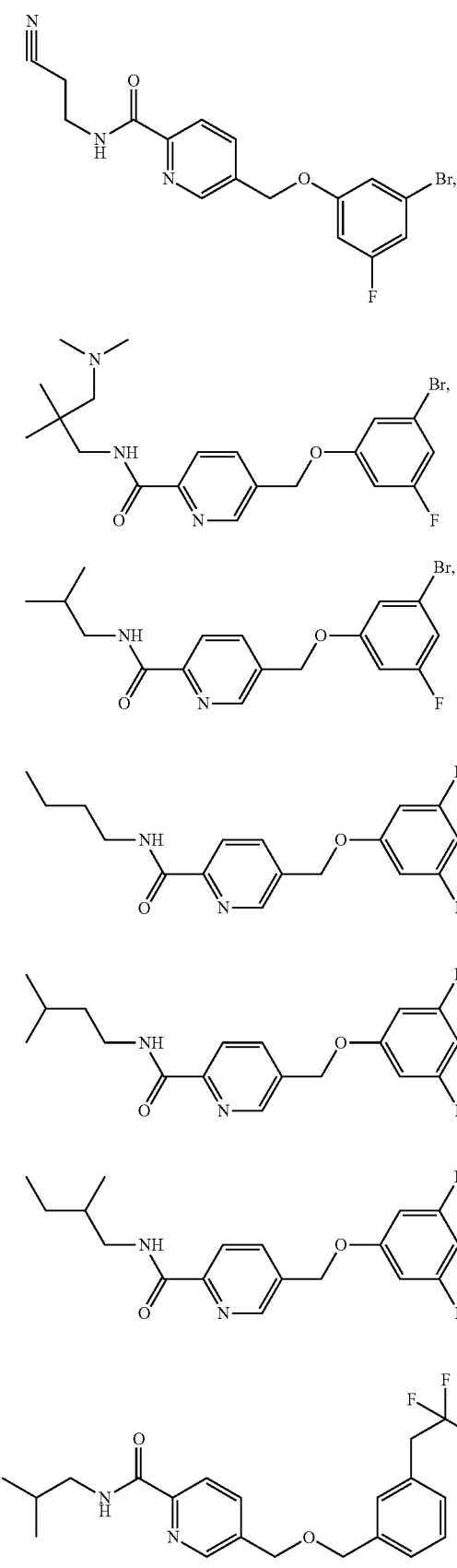
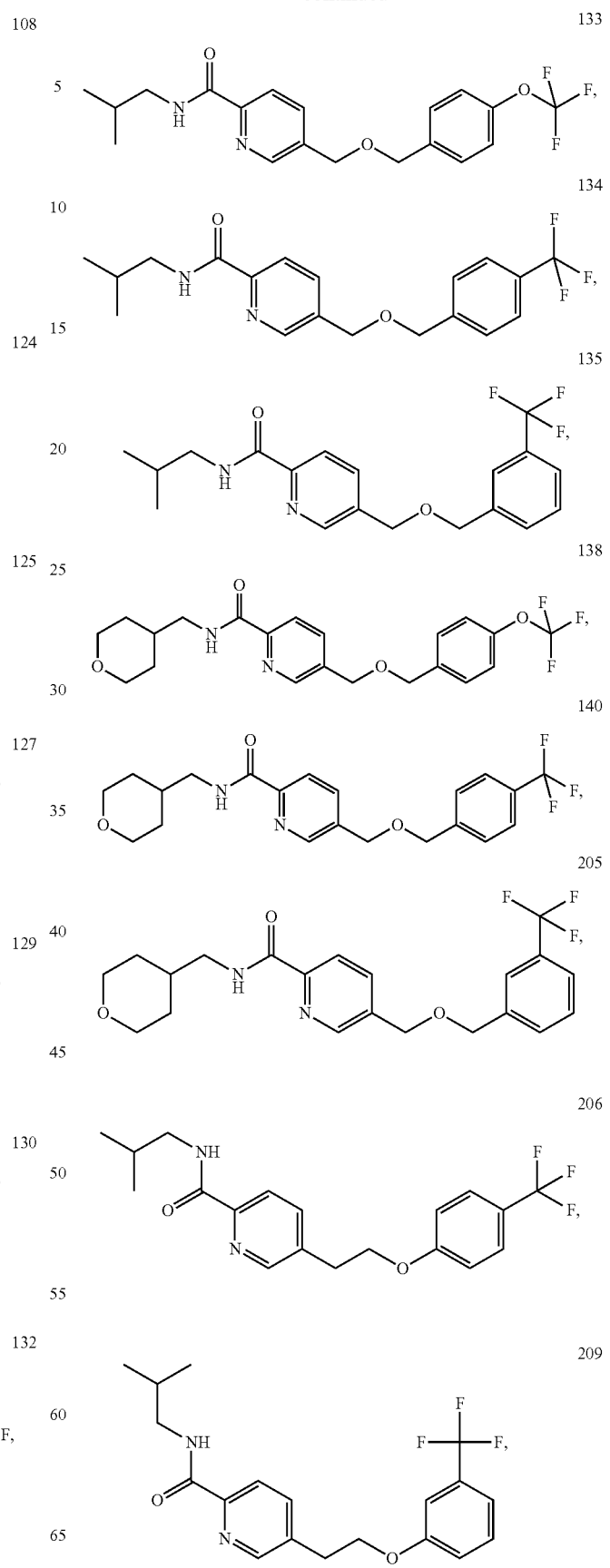

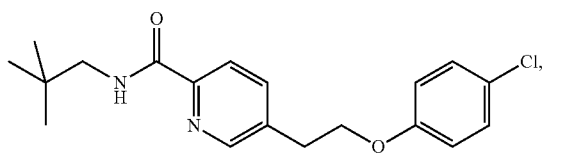
216
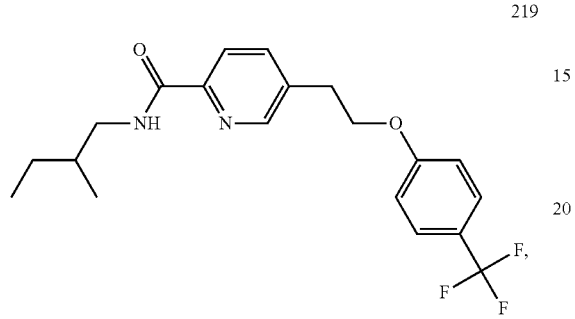
219
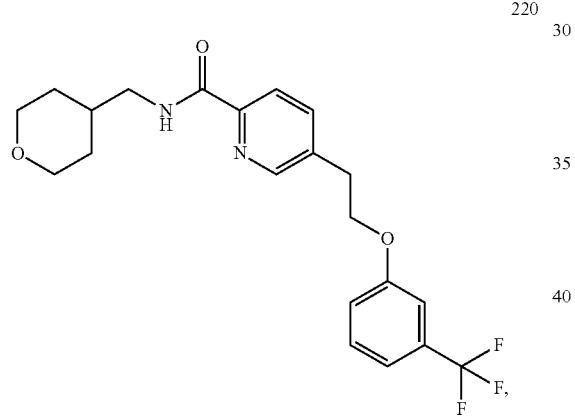
220
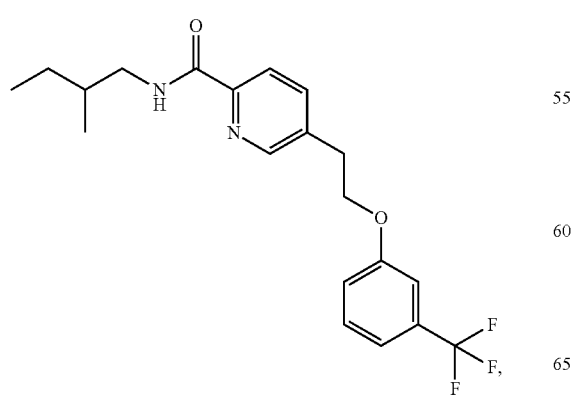
221
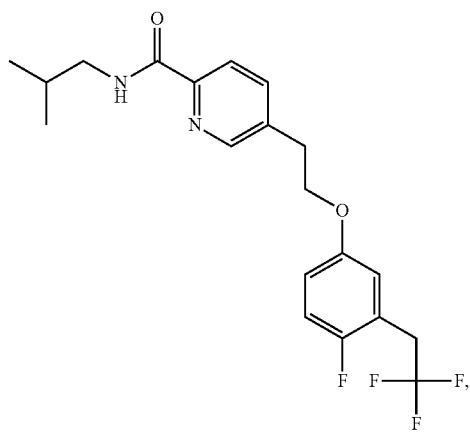
222
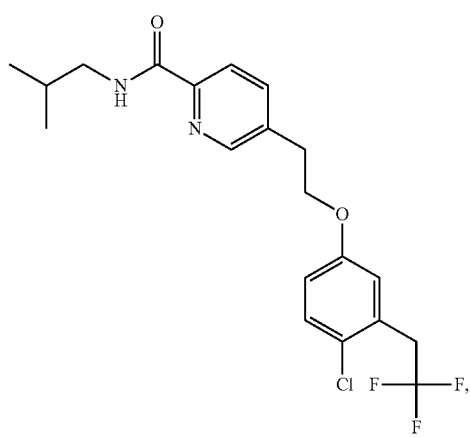
223
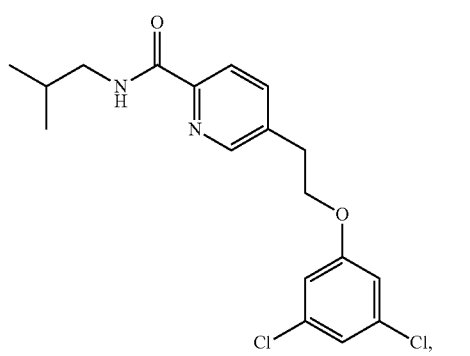
225
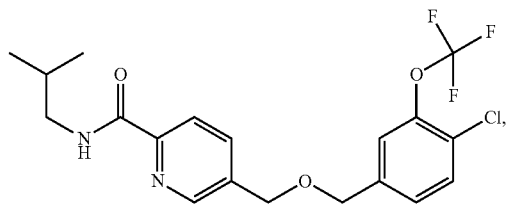
227

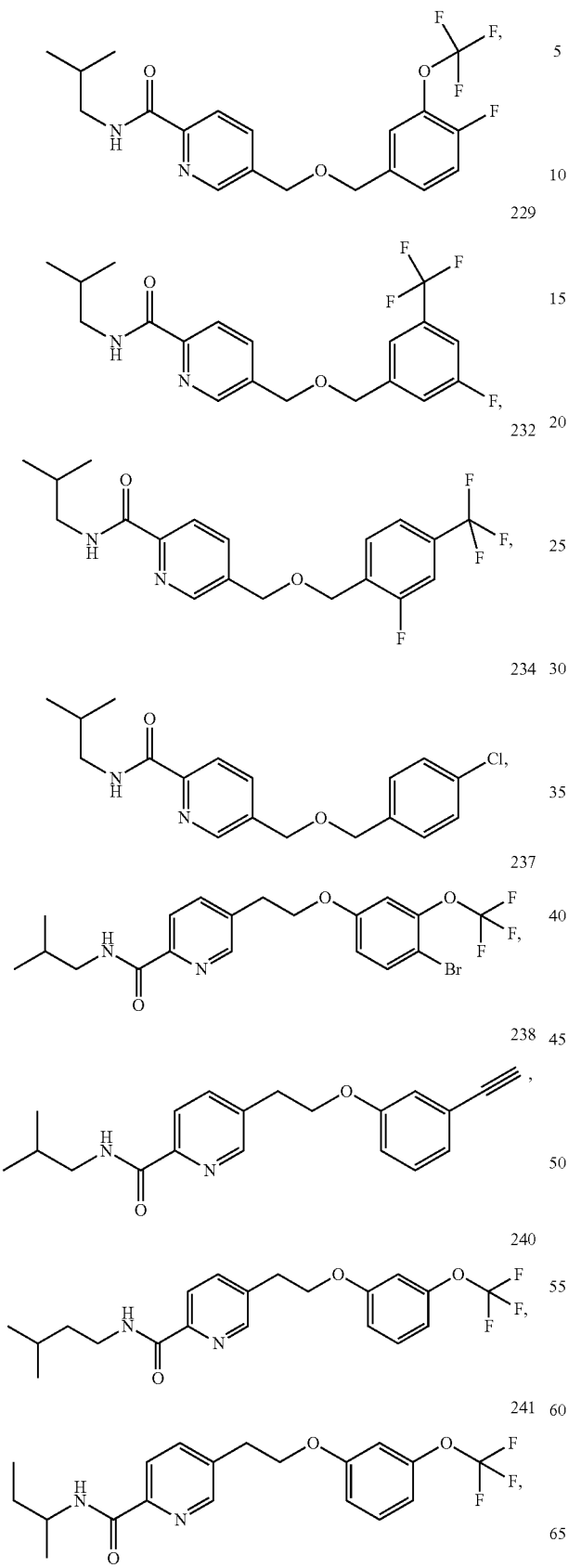
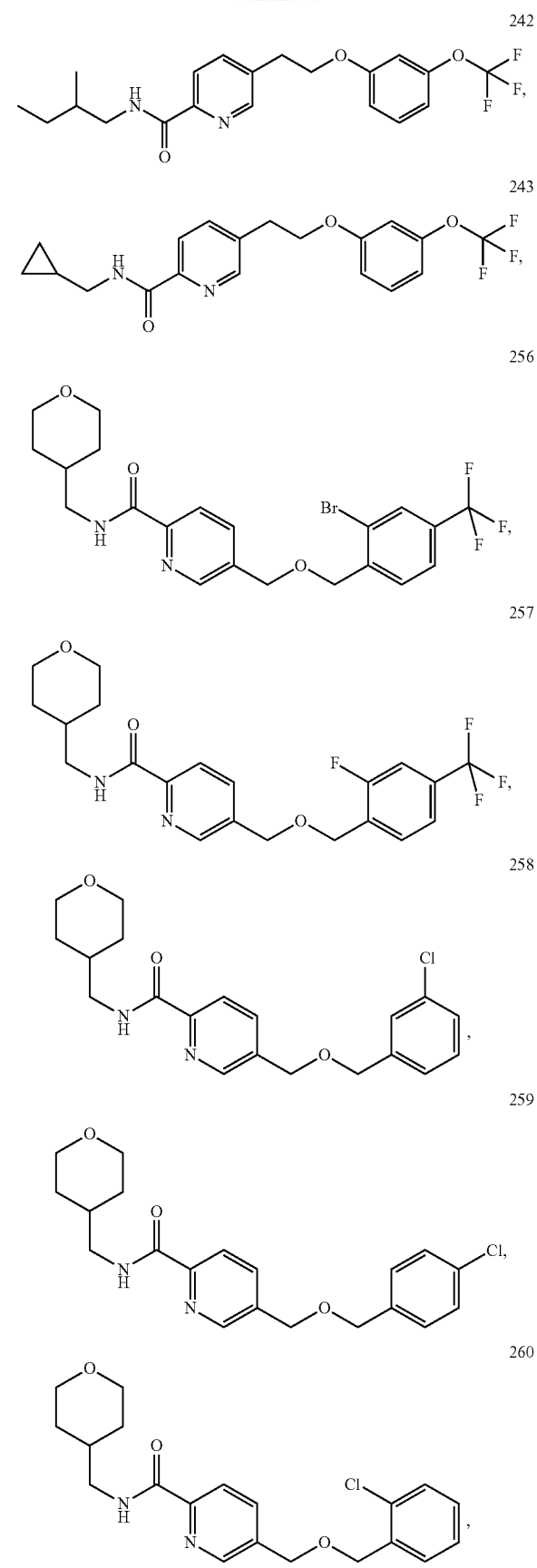

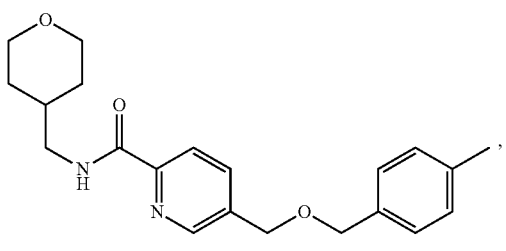

263

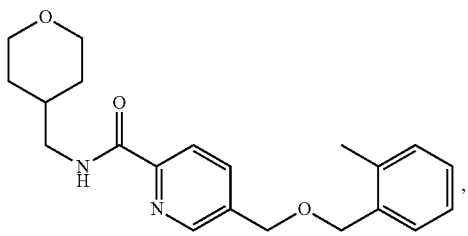

264

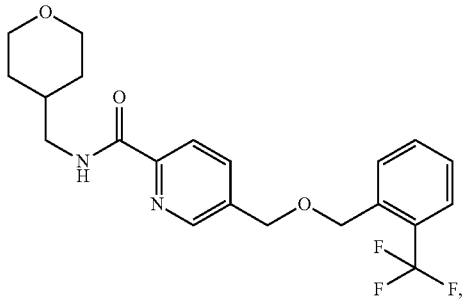

266

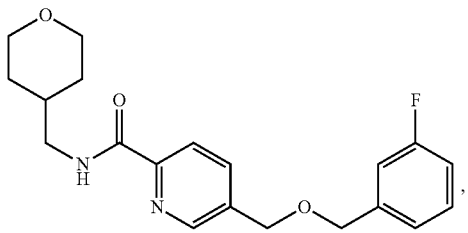

268

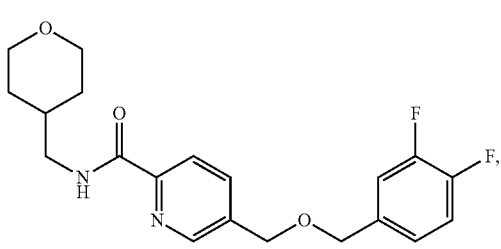

270

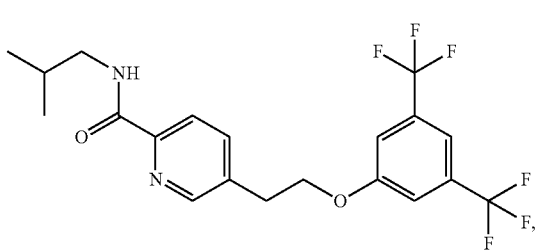

275

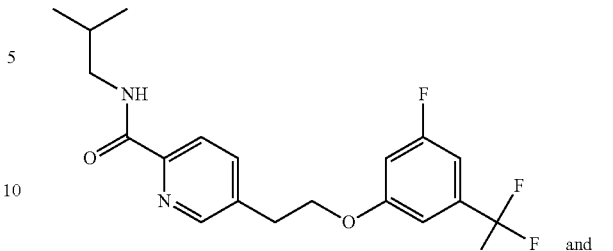

278 and

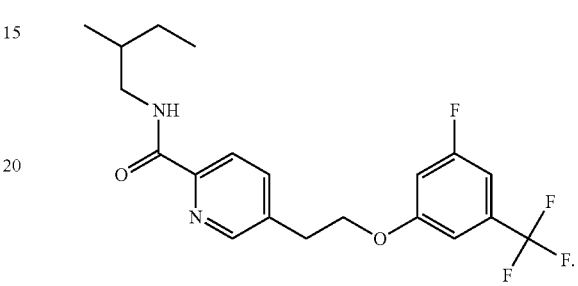

279

19. A paraciticidal composition comprising a compound of claim 1 and a carrier.

20. The composition of claim 19, further comprising one or more additional active agents.

21. A method of treating or preventing infection or infestation of an animal by one or more parasites, said method comprising administering an effective amount of a compound of claim 1.

22. The method of claim 21, wherein said one or more parasites is selected from the group consisting of fleas, ticks, mites, mosquitoes, flies, fly larvae and lice and combinations thereof.

23. The method of claim 21, wherein said one or more parasites is selected from the group consisting of fleas and ticks and combinations thereof.

24. The method of claim 21, wherein said one or more parasites is an ectoparasite or an endoparasite or a combination thereof.

25. The method of claim 24, wherein said ectoparasite is an arthropod.

26. The method of claim 25, wherein said arthropod is selected from the group consisting of houseflies (*Musca domestica*), *Musca hervei*, *Musca bezzi*, *Haematobia irritans*, *Simulium iwatens*, *Culicoides oxystoma*, *Tabanus chrysurus*, common mosquito (*Culex pipiens*), *Aedes albopictus*; lice pests (Anoplura), cattle lice (*Haematopinus eurysternus*), sheep lice (*Damalinia ovis*); tick pests (Acarina), *Haemaphysalis longiconis*, *Boophilus microplus*; fleas (Siphonaptera), cat fleas (*Ctenocephalides felis*), dog fleas (*Ctenocephalides canis*) and oriental rat flea (*Xenopsylla cheopis*).

27. The method of claim 24, wherein said endoparasite is a helminth.

28. The method of claim 24, wherein said endoparasite is selected from the group consisting of *Anaplocephala* (*Anoplocephala*), *Ancylostoma*, *Anecator*, *Ascaris*, *Brugia*, *Bunostomum*, *Capillaria*, *Chabertia*, *Cooperia*, *Cyathostomum*, *Cylicocyclus*, *Cylicodontophorus*, *Cylicostephanus*, *Craterostomum*, *Dictyocaulus*, *Dipetalonema*, *Dipylidium*, *Dirofilaria*, *Dracunculus*, *Echinococcus*, *Enterobius*, *Fasciola*, *Filaroides*, *Habronema*, *Haemonchus*, *Metastrongy-*

*lus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria, Haemonchus contortus, Ostertagia circumcincta, Trichostrongylus axei, Trichostrongylus colubriformis, Cooperia curticei, Nematodirus battus* and combinations thereof.

\* \* \* \* \*